United States Patent
Tomalia et al.

(10) Patent No.: US 10,968,176 B2
(45) Date of Patent: *Apr. 6, 2021

(54) PYRROLIDONE DERIVATIVES, OLIGOMERS AND POLYMERS

(71) Applicant: NanoSynthons LLC, Mt. Pleasant, MI (US)

(72) Inventors: Donald A Tomalia, Midland, MI (US); David M Hedstrand, Midland, MI (US); Linda S Nixon, Mt. Pleasant, MI (US)

(73) Assignee: NanoSynthons LLC, Mt. Pleasant, MI (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/510,620

(22) Filed: Jul. 12, 2019

(65) Prior Publication Data

US 2019/0352258 A1 Nov. 21, 2019

Related U.S. Application Data

(63) Continuation-in-part of application No. 15/510,862, filed as application No. PCT/US2015/050062 on Sep. 14, 2015, now Pat. No. 10,420,849.

(60) Provisional application No. 62/050,164, filed on Sep. 14, 2014.

(51) Int. Cl.

| | | |
|---|---|---|
| *C07D 207/28* | (2006.01) | |
| *C08G 73/06* | (2006.01) | |
| *C08G 81/00* | (2006.01) | |
| *C08G 83/00* | (2006.01) | |
| *A61K 47/59* | (2017.01) | |
| *C09K 11/06* | (2006.01) | |

(52) U.S. Cl.
CPC .......... *C07D 207/28* (2013.01); *A61K 47/595* (2017.08); *C08G 73/0611* (2013.01); *C08G 81/00* (2013.01); *C08G 83/003* (2013.01); *C09K 11/06* (2013.01); *C09K 2211/1018* (2013.01); *C09K 2211/1466* (2013.01)

(58) Field of Classification Search
CPC ....... C07D 277/28; A61K 49/00; A61K 47/59
See application file for complete search history.

(56) References Cited

U.S. PATENT DOCUMENTS

| | | | |
|---|---|---|---|
| 4,179,337 A | 12/1979 | Davis et al. | |
| 2006/0160988 A1* | 7/2006 | Tomalia | C08G 83/003 528/310 |
| 2007/0298006 A1 | 12/2007 | Tomalia et al. | |
| 2014/0303123 A1 | 10/2014 | Baker et al. | |

FOREIGN PATENT DOCUMENTS

| | | |
|---|---|---|
| WO | 2001/44230 | 6/2001 |
| WO | 2003/059905 | 7/2003 |
| WO | 2004/069878 | 8/2004 |
| WO | 2005/014540 | 2/2005 |
| WO | 2006/065266 | 6/2006 |
| WO | 2006/115547 | 11/2006 |

OTHER PUBLICATIONS

Michal Ciolkowski et al., Surface modification of PAMAM dendrimer improves its biocompatibility, Nanomedicine: Nanotechnology, Biology and Medicine, 8, 815-817. (Year: 2012).*
M.Y. Berezin, S. Achilefu, Chem. Rev., 110, 2641-2684, 2010.
The Molecular Probes Handbook, A Guide to Fluorescent Probes and Labeling Technologies, 11th Ed., 2010.
C.-C. Chi, S.H. Wang, T.-T. Kuo, J. Cutan. Pathol., 33, 454-457, 2006.
K. Knop, R. Hoogenboom, D. Fischer, U.S. Schubert, Angew. Chem. Int. Ed., 49, 6288-6308, 2010.
A. Janaszewska, M. Ciolkowski, D. Wrobel, J.F. Petersen, M. Ficker, J.B. Christensen, M. Bryszewska, B. Klajnert, Nanomedicine (Elsevier), 9, 461-464, 2013.
N. Spyropoulos-Antonakakis, E. Sarantopoulou, P.N. Trohopoulos, A.L. Stefi, Z. Kollia, V.E. Gavrill, A. Bourkoula, P.S. Petrou, S. Kakabakos, V.V. Semashko, A.S. Nizamutdinov, A.-C. Cefalas, Nanoscale Research Letters, 10, 210, 1-19, 2015.
Ciolkowski et al., Nanomedicine: Nanotechnology, Biology and Medicine 8(6), 815-817, 2012.
Kim et al., Biophisical J., 104(7), 1566-1575, 2013.

* cited by examiner

*Primary Examiner* — Michael G. Hartley
*Assistant Examiner* — Jagadishwar R Samala
(74) *Attorney, Agent, or Firm* — Technology Law PLLC; Karen L Kimble

(57) ABSTRACT

Simple organic structures, organic/inorganic polymers, and other substrates have been made, all of which have at least one pyrrolidone moiety present, and found to exhibit low toxicity, low complement activation features and may be used to reduce protein interactions with drug conjugates while enhancing in vivo residency times for these conjugates when used as an injectable composition; thus these compounds can be used as substitutes for PEG in PEGylation. Surprisingly, these compounds also exhibit unique intrinsic fluorescence (IF) or non-traditional fluorescence (NTF) properties that currently cannot be explained by traditional photochemistry and fluorescence paradigms are described. These compounds have a variety of applications such as in cellular imaging, gene transfection, bio-diagnostics, biosensing, fluorescence directed surgical resections, drug delivery, forensics, environmental diagnostics, mineral/gemstone characterization, counterfeit goods detection, tracer studies related to liquid/water flow, oil field enhancements and diagnostics, prevention of photo-bleaching, and LED display enhancements and others.

21 Claims, 15 Drawing Sheets

(A)  (B)

(C)  (D)

mHippoE-18 (blue rhombus), BRL-3A (red circles) and B-14 (green triangles) cells mHippoE-18 (blue rhombus), BRL-3A (red circles) and B-14 (green triangles) cells (A)

(B)

Scheme 2

PYRROLIDONE DERIVATIVES, OLIGOMERS AND POLYMERS

BACKGROUND OF THE INVENTION

Field of the Invention

This invention generally concerns the use of derivatives/analogues of poly(vinylpyrrolidone) (PVP), namely poly(pyrrolidone) macrocyclics, oligomers and low molecular weight polymers as masking agents for biological materials in a manner analogous to those obtained using poly(ethyleneglycol) (PEG). Additionally, the small molecule pyrrolidone intermediates (i.e., the monomeric precursors) as well the new poly(pyrrolidone) oligomers/polymers obtained from these derivatives exhibit unique intrinsic fluorescence (IF) or non-traditional fluorescence (NTF) properties that cannot be explained by traditional photochemistry and fluorescence paradigms. These compounds, oligomers and polymers have a variety of applications such as in masking drugs for biological applications, cellular imaging, gene transfection, biosensing, fluorescence directed surgical resections, drug delivery, forensics, mineral/gemstone characterization, oil field enhancement and diagnostics, counterfeit goods detection, tracer studies related to liquid/water flow, fluorescent whitening agents and LED display enhancements and others.

Description of Related Art

PEGylation

The general concept of PEGylation was first introduced and patented in the 1970's by F. Davis et al., (U.S. Pat. No. 4,179,337 (1979)) as a strategy to reduce toxicity, immunogenicity and proteolytic degradation of therapeutic drugs/proteins, while enhancing blood circulation times, drug solubility and PK/PD's of the therapy. The strategy involves the covalent conjugation of poly(ethylene glycol) oligomers (i.e., DP=4-50) to the desired therapeutic drug or substrate. This PEGylation strategy has provided the basis for launching over a dozen important drugs that include: for cancer treatment such as Doxil/Caelyx® by Ortho/Schering-Plough (2001), multiple sclerosis, such as Plegridy® by Biogen (2014), cancer related drug Movantik® by AstraZeneca (2014), anemia such as Peginesatide® by Affmax Takeda Pharma, (2012), to mention a few. This strategy involves the covalent conjugation of low molecular weight PEG oligomers (i.e., <50-70 KDa) using so-called, "activated PEG reagents" as described below:

$$X\text{---}(OCH_2CH_2)\text{---}Y_n$$

where: X and Y can be independently reactive or non-reactive with functionality possessed by the desired protein, polynucleotide or therapeutic drug to be modified; n is from 4-50.

POXylation

Due to a number of shortcomings related to PEG oligomer chemical properties (i.e., oxidative, enzymatic stability or immunogentic problems with chronic use and due to higher MW fractions), (G. T. Hermanson, Chapter 18 in *Bioconjugate Techniques*, Second Ed., (2008) 707-742), there has been an active quest for alternative polymer types and compositions. This has led to an early report by Zalipsky et al. (see S. Zalipsky, et al., *J. Pharm. Sci.*, (1996), 85, 133-137) describing the usefulness and potential advantages of poly(oxazolines) as a replacement for PEG's. Very recently, work has focused on the use of poly(oxazolines) (F. M. Veronese, et al., *Bioconjugate Chem.*, (2011), 22, 976-986) and POXylation conjugates of rotigotine (i.e., dopamine agonist) for the treatment of Parkinson's disease by Serina Therapeutics (www.serinatherapeutics.com). As such, these POXylation protocols involve the use of "activated POX reagents" for attachment to these therapeutic drugs/proteins as described below:

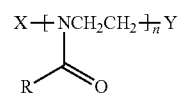

where: X and Y can be independently reactive or non-reactive with functionality possessed by the desired protein, polynucleotide or therapeutic drug to be modified; n is from 4-50.

Historical Use of Poly(Vinylpyrrolidone) (PVP) as an Injectable Synthetic Polymer in Humans Historically, the most extensively studied/documented synthetic polymer composition utilized for internal injection in humans has been poly(vinylpyrrolidone) (PVP). For over 75 years, since its discovery in the late 1930's, this polymer has been injected in over 500,000 human patients with virtually no adverse toxicity, immunogenicity or other negative effects for use as a very successful blood substitute/extender (Sultana, et al., *J. Pakistan Med. Association*, (1978), 28 (10), 147-153). More extensive and contemporary human use of this synthetic polymer composition as an injectable has been hampered solely by concerns that higher molecular weight polymer fractions (i.e., >70 KDa) may not be adequately excreted through the kidney and be accumulated in vivo with multiple injections and over extended time. This hypothesis appears to have been confirmed by several well documented medical studies (Wang et al., *J. Cutan Pathol.*, 2006, 33, 454-457). The specific medical condition created is referred to as; PVP accumulation disease or Dupont-Lachapelle Disease. This medical condition is widely recognized to be due to non-excretable, higher molecular weight PVP fractions present in currently available poly(pyrrolidone) products. Although this medical condition is not fatal, it is considered to be a negative feature for PVP since higher molecular weight PVP fractions have been proven difficult if not impossible to remove (Pfirrmann et al., U.S. Pat. No. 6,080,397, 2000) and will require a significant scientific solution or alternative for future use.

Currently, PVP polymers are produced commercially in large quantities by various manufacturers such as BASF. PVP production involves the free radical polymerization of N-vinyl pyrrolidone monomer (N-VP). The N-VP monomer is obtained by the original Reppe process involving the combination of acetylene, formaldehyde and ammonia under high pressure (see Scheme 1 below).

Scheme 1

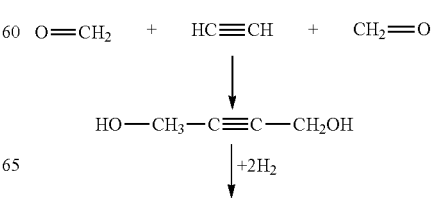

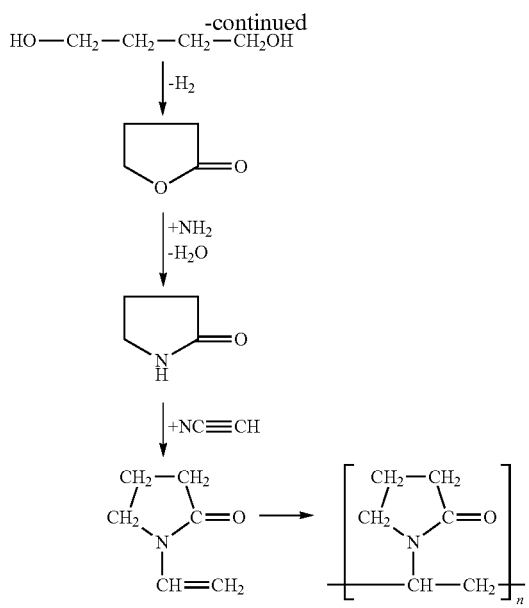

The (N-VP) monomer has been successfully polymerized only with free radical catalysts (i.e., peroxides, persulfates) in bulk, solution or in suspension, to give linear-PVP with weight-average molar masses ranging from 2500-1,000,000 Da (see Haaf et al. *Polymer Journal*, 1985, 17(1), 143-152). These linear-PVP polymers are generally obtained as highly poly-dispersed products and were characterized by measuring their viscosities in solution according to a "Fikentscher K-value molecular weight relationship" developed by Kern and Cherdron (Kern et al., *Houben Weyl, Methoden der Organische Chemie*, Vol. 14, 4$^{th}$ ed., Georg Thieme Verlag, Stuttgart, 1961, p.1106), using the relationship between $M_w$, $M_n$ and K; wherein: $M_w=15K^{2/3}$ and $M_n=24K^2$. The letter K together with an appropriate number is used to relate the molecular weight for the various PVP molecular weight fractions. For example a K-12 has an average molecular weight of ~20,000 Da and K-90 has a molecular weight of ~1M Da. Therefore, PVP with a specified K-value and average molecular weight consists of a range of molecular sizes. Based on these viscosity characterization protocols it is clearly apparent that well-defined molecular weight ranges let alone well defined, controllable molecular weights for PVP do not currently exist. Controlling PVP polymer molecular weights, which is related to nanoscale sizes, is a critical issue for many nanomedicine applications, wherein, nanoscale size is known to determine excretion modes, bio-distributions, toxicology and complement activation properties (see for example Kannan et al., *J. Intern. Med.* 2014, 276, 579-617).

The pyrrolidone moiety as found in PVP (i.e., Povidone, trademark of BASF) enjoys an excellent record and universal recognition as a versatile non-toxic, biocompatible, physiologically inert material for a wide variety of medical applications (see Haaf et al., *Polymer Journal*, 1985,17(1), 143-152). Foremost has been the extensive in vivo use of PVP as a blood plasma extender (e.g., Sultana, et al., *J. Pakistan Med. Association*, 1978, 28, (10), 147-153); wherein, it has undoubtedly saved countless lives. During World War II, (i.e., initiated by I. G. Farben; now Providone by BASF) and in subsequent years (Korean War) [http://hcvets.com/data/military/korea.htm; page 44], referred to in Sweden as Periston; it is documented that PVP has been used internally via injection in over 500,000 human recipients as a blood extender (Sultana, et al., *J. Pakistan Med. Association*, 1978, 28, (10), 147-153) without any significant evidence of deleterious effects (Ravin et al., *New England J. of Med.*, 1952, 247, 921-929). Radioactive studies showed that 95-100% of injected PVP (i.e., Periston) was excreted via the urine within 72 hours; 40% was excreted within 20 minutes; and within 6 hours, virtually all circulating PVP had disappeared from the plasma. Subsequent research has shown that the (PVP) composition exhibits virtually no antigenic properties (Maurer et al., *J. Immunology*, 1956, 77(2) 105-110) compared to other synthetic (i.e., polyesters/polyalcohols) or biological polymers (i.e., poly(dextrans) or poly(saccharides)).

Currently, (PVP) is being used as an adjuvant for immobilizing spermatozoa for in vitro fertilization protocols (www.coopersurgical.com). Other examples include the use of PVP in applications ranging from cosmetics (e.g., hair sprays) to eye drops and oral pill binding formulations. More recent confirmation of the low cytotoxicity and minimal interaction of the poly(pyrrolidone) moiety with proteins, when presented on the surface of poly(amidoamine) (PA-MAM) dendrimers has been reported (Ciolkowski et al., *Nanomedicine, NBM*, 2012, 8, 815-817; and Janaszewska et al., *Nanomedicine, NBM*, 2013, 9, 461-464).

As such, there is a critical need to synthesize/control the PVP molecular weight in a range of 3-14 KD (Pfirrmann et al., U.S. Pat. No. 6,080,397, 2000). This is necessary to avoid in vivo accumulation of higher MW PVP fractions and be acceptable as an injectable product for in vivo applications. Unfortunately, all known polymerization mechanisms (i.e., free radical, anionic, cationic types) for propagating N-vinyl pyrrolidone to produce PVP polymers lead to substantial amounts of uncontrolled, higher molecular weight (i.e., >14 KDa). PVP products, as well as polymerization side products that make these materials unacceptable for in vivo or injectable product applications. More specifically, when PVP containing higher molecular weight fractions (i.e., >14 KDa) are administered intravenously, an in vivo accumulation of the polymer may occur which is referred to as "PVP storage disease" or also known as the Dupont-Lachapelle Disease (Wang et al., *J. Cutan Pathol.*, 2006, 33, 454-457). This disease is characterized by symptoms that include dermatosis, rheumatic joint pain, and pulmonary respiratory insufficiency. On the other hand, low molecular weight PVP with a molecular weight of <14 KDa and a K-value less than 17 has been found to be non-allergenic and is quickly removed unchanged by excretion from the blood stream via the kidneys. However, all attempts at producing low MW PVP exclusively by free radical polymerization and subsequent ultra-filtration have been unsuccessful (Pfirrmann et al., U.S. Pat. No. 6,080,397, 2000; www.rloginconsulting.com/pyrrolidone%20backbone%20polymers.pdf).

Fluorescence Discussion

Fluorescence occurs when an orbital electron of an atom, molecule, polymer or nanostructure in the ground state ($S_0$) is excited to a higher quantum state ($S_1$) by the absorption of some form of energy (i.e., usually a photon; $h\nu_{ex}$) and then relaxes back to the ground state (see FIG. 1). This two-step process is described as:

1. Excitation: $(S_0)+h\nu_{ex}\rightarrow(S_1)$
2. Fluorescence (emission): $(S_1)\rightarrow(S_0)+h\nu_{em}+$heat This relaxation or return [i.e., (S1)→(S0)] to the ground state is accompanied by the emission of lower energy photons of light ($h\nu_{em}$), which is referred to as fluorescence (see FIG. 1). (*The Molecular Probes Handbook—A Guide to Fluorescent Probes and Labeling Technologies*, 2010, 11$^{th}$ Ed.)

A fluorophore in the ($S_1$) state may return to the ground state ($S_0$) via relaxation pathways involving either radiative emission (i.e., fluorescence), non-radiative events (i.e., heat) or internal intersystem conversion (IC) (i.e., intersystem crossover, (ISC)) to a non-fluorescent triplet excited state ($T_1$) with time scales on the order of $10^{-10}$ to $10^{-9}$ seconds.

These ($T_1$) species are very sensitive to molecular oxygen and may undergo redox reactions leading to highly reactive superoxide radicals (ROS) and irreversible fluorophore damage referred to as "photobleaching" (Q. Zheng, et al., *Chem. Soc. Rev.*, 2014, 43, 1044-1056). These highly reactive oxygen species (ROS) may cause fluorophore degradation or cause phototoxicity by reacting with nearby biomolecules and are in fact pivotal to so-called photodynamic therapies employed in nanomedicine.

Due to vibrational relaxations following excitation, the photon energy emitted from ($S_1$) will generally be lower than the excitation photon. This results in an increase in the fluorescence emission wavelength which may range from 5-50 nm higher than the excitation wavelength. The difference between the excitation wavelength and the emission wavelength is referred to as the Stokes shift (N. J. Turro et al., *Modern Molecular Photochemistry of Organic Molecules*, 2010 University Science Books, *The Molecular Probes Handbook—A Guide to Fluorescent Probes and Labeling Technologies*, 2010, 11$^{th\ Ed.}$).

Fluorescence imaging techniques have broad applications in life sciences and clinical research. However, these techniques critically rely on bright and photostable fluorescent probes. Currently available fluorescent probes for biological imaging mainly include organic fluorophores (Terai and Nagano, *Pflugers Archiv. European J. Physiology*, 2013, 465, 347-359) and quantum dots (Chen et al., *Trends Analytical Chemistry*, 2014, 58, 120-129). Small organic dyes suffer from several unwanted properties such as poor solubility, problems with targeting desired cell compartments, rapid irreversible photobleaching, and cell leakage. Inorganic nanoconjugates such as quantum dots are exceptionally bright, photostable, and characterized by narrow emission spectra, but they possess important drawbacks. First of all, they are toxic and that can limit their applications in vivo. Moreover, their intracellular delivery raises problems that make it difficult to follow some biological processes (Jamieson et al., *Biomaterials*, 2007; 28, 4717-4732).

Fluorescence in the field of biology and nanomedicine has become a major research focus due to their broad applications in cellular imaging, biosensing, fluorescence directed surgical resections (R. Tsien et al., *Proc. of the National Acad. of Sci.*, 2010, 107, 4317-4322) and drug delivery (i.e., theranostics) (S. Lo, et al., *Mol. Pharmaceutics*, 2013, 10, 793-812; R. Tsien et al., *Proc. of the National Acad. of Sci.* 2010, 107, 4311-4316).

Applications of fluorescence outside of biology/medicine uses include, but are not limited to: forensics (M. Y. Berezin et al., *Chem. Reviews*, 2010, 110, 2641-2684); oil field enhancement and diagnostics (M Amanullah, 2013, SPE164162); counterfeit goods detection (U.S. Pat. No. 8,735,852, issued May 27, 2014; Y. Zhang et al., *Dyes Pigm.*, 2008, 77, 545); tracer studies related to liquid/water flow (WO 2011/030313, A method for detecting an analyte, *Indian Inst. of Science*, Mar. 17, 2011); fluorescent whitening agents; and LED display enhancements (US Pat. Appl. 20140035960, Apple Inc.) and others.

Traditional standard fluorescing agents are usually described as being members of three major categories:

Category I are organic aromatic conjugated polyenes that include small molecules with low molecular weight (<1000 da) and are derived from these conjugated organic aromatics structures.

Category II consists of fluorescent proteins that usually contain one or more of the three key aromatic moieties such as tryptophan, tyrosine and/or phenylalanines.

Category III consists of inorganic nanoparticles derived from cadmium or lead chalcogenides such as heavy metal sulfides or selenides that must have sizes smaller than a Bohr exciton or radius (2-50 nm). Their fluorescence is determined by their size, but do not exhibit the weakness of photobleaching.

The weaknesses of each traditional fluorophore category are as follows: Category I—lack robustness in the presence of oxygen which leads to rapid fluorophore degradation referred to as photobleaching, as well as photo-toxicity resulting from the generation of the reactive oxygen species (ROS) which may cause cellular damage and potential carcinogenicity; Category II: proteins that may denature, lack robustness in the presence of oxygen which leads to rapid degradation referred to as photobleaching, exhibit immunogenicity; Category III: quantum dots exhibit heavy metal toxicity, blinking fluorescence, lack of solubility for in vivo applications, size must be nanometric and precise (2-50 nm).

The pyrrolidone moiety on the other hand which is a critical component of this invention has an excellent record and international recognition as a versatile non-toxic, biocompatible material for a wide variety of medical applications. Foremost has been the extensive use of poly(vinylpyrrolidone) (PVP) as an in vivo blood plasma extender (Polyvinyl Pyrrolidone as a Plasma Expander—Studies on Its Excretion, Distribution and Metabolism, Herbert A. Ravin, Arnold M. Seligman, M. D., and Jacob Fine, M. D.). Since the World War II, it has been used in over 500,000 human recipients without any evidence of deleterious effects (H. A. Ravin, *N. Engl. J. Med.*, 1952, 247, 921-929).

In another feature, dendritic polymers are known in the art and are discussed extensively in DENDRIMERS, DENDRONS, AND DENDRITIC POLYMERS, Tomalia, D. A., Christensen, J. B. and Boas, U. (2012) Cambridge University Press, New York, N.Y. Dendritic polymers have become recognized as the fourth and most recently reported major class of polymeric architecture (*J. Polym. Science, Part A: Polym. Chem.* 2002, 40, 2719-2728).

Three major architecture components of dendrimers, namely the cores, interior compositions as well as their surface chemistries can be readily modified. At the present, dozens of diverse cores, nearly 100 different interior compositions and over 1000 different surface moieties have been reported for dendrimers [e.g., DENDRIMERS, DENDRONS, AND DENDRITIC POLYMERS, Tomalia, D. A., Christensen, J. B. and Boas, U. (2012) Cambridge University Press, New York, N.Y.]. In many cases dendrimer surface modifications have been performed to alter, enhance or obtain new emerging properties such as: to modify/reduce dendrimer toxicity, gain enhanced solubilities, reduce dendrimer-protein interactions/immunogenicity (i.e., dendrimer stealthness), for the attachment of drugs, targeting or imaging agents including traditional fluorophores such as fluoroscein, Rhodamine red or cyanine dyes. Many of these surface chemistry enhanced dendrimer properties have been shown to be invaluable in a variety of life sciences and nanomedicine applications (e.g., U.S. Pat. No. 5,527,524).

As early as 2001, poly(amidoamine) (PAMAM) dendrimers were reported by Tucker et al., (S. Tucker et al., *Applied Spectroscopy*, 2001, 55, 679-683) to exhibit intrinsic fluorescence properties that could not be explained mechanistically by any known traditional fluorescence paradigm. This new non-traditional fluorescence (NTF), observed in dendrimers, generally required excitation radiation between 250-400 nm, followed by relaxation to the ground state to produce characteristic emission bands that ranged from the visible to near infrared region (i.e., 400-750 nm).

Since this early report, the NTF phenomena has been observed in a wide range of different dendrimer families (i.e., interior compositions) all of which appear to have one thing in common, namely they possess multiples of tertiary amines ($3°$-amines) and/or amides in their interior backbone compositions. It is notable that dendrimer terminal/surface functionality did not appear to significantly influence (NTF); however, dendrimer generation level (G. Jayamurugan et al., *Org. Lett.*, 2008, 10, 9-12), degree of dendrimer aggregation (P. K. Antharjanam et al., *J. Photochemistry & Photobiology A: Chem.*, 2009, 203, 50-55), solvent viscosities (P. K. Antharjanam et al., *J. Photochemistry & Photobiology A: Chem.*, 2009, 203, 50-55), low pH's (T. Imae et al., *J. Am. Chem. Soc.*, 2004, 126, 13204-13205; L. Pastor-Perez et al., *Macromol Rapid Commun.*, 2007, 28, 1404-1409; Y. Wang et al., *J. Nanosci. Nanotechnol.*, 2010, 10, 4227-4233; Y. Shen et al., *Chem. Eur. J.*, 2011, 17, 5319-5326), aging (D. Wang et al., *J. Colloid & Interface Science*, 2007, 306, 222-227), exposure to air or oxidizing reagents (A. J. Bard et al., *J. Am. Chem. Soc.*, 2004, 126, 8358-8359; T. Imae et al., *Colloids & Surfaces B: Biointerfaces*, 2011, 83, 58-60), and even a few others, did cause enhancements in fluorescence intensities. In addition to the early more ordered, monodispersed dendrimer examples, the (NTF) phenomena was subsequently observed in several other major macromolecular architectures including: (a) random hyper-branched (Y. Chen et al., *Bioconjugate Chem.*, 2011, 22, 1162-1170), (b) linear (L. Pastor-Perez et al., *Macromol Rapid Commun.*, 2007, 28, 1404-1409) and (c) certain simple branched (S.-W. Kuo et al., *J. of Nanomaterials*, 2012, 749732, 10 Pages) polymer structures. In spite of many attempts to utilize these unique dendrimer (NTF) properties for imaging biological cells or labeling, the low (NTF) fluorescence emission intensities generally precluded their practical use, except in the presence of certain oxidizing reagents/environment or at low pH's (i.e., 2-3) in order to obtain an adequate emission intensity for certain applications such as gene transfection (Y. Chen et al., *Bioconjugate Chem.*, 2011, 22, 1162-1170).

Applying dendrimers—versatile, globular, monodisperse polymers with many surface functional groups—seems to be a solution that may help to overcome limitations of both single organic fluorophores and inorganic nanoprobes. The size of dendrimers places them on the same scale as fluorescent proteins: they are larger than organic dyes and smaller than quantum dots.

Dendrimers have been used as scaffolds for fluorophores. G2 PAMAM dendrimers with PEG chains have been functionalized with two types of fluorophores: carboxy-fluorescein and tetramethyl-rhodamine and tested in Chinese hamster ovary cells (Albertazzi et al., *PloS ONE*, 2011, 6, e28450. doi:10.1371/journal.pone.0028450). Higher generations G5 and G6 PAMAM dendrimers have been conjugated with multiple cyanine dyes (Kim et al., *Biophys. J.*, 2013, 104, 1566-1575). In many cases covalent attachment of fluorescent labels on the surface of the dendrimer is necessary to evaluate its biological functions in vitro or in vivo. However, such a modification creates a risk of decreased dendrimer biocompatibility, and affects its biodistribution properties. That is why seeking intrinsically fluorescent dendrimers are of paramount importance.

Clearly, having biocompatible compounds that display fluorescence in the desired wavelength and intensity, with low toxicity, for the intended use has commercial application.

BRIEF SUMMARY OF THE INVENTION

The present invention provides fluorescent cyclic amides, cyclic urea, cyclic urethanes and cyclic amino amide or amino urea compounds of the formula

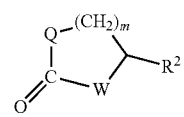

Formula (I)

wherein:
Q is any entity that has a primary amine that reacts to introduce a nitrogen in the ring as shown;
W is N, O, S or $(CH_2)_n$ where n is 0 or 1;
$R^2$ is —C(O)OH; —C(O)O($C_1$-$C_4$ alkyl); —C(O)—NHR$^5$ wherein R$^5$ is $C_1$-$C_4$ alkyl or an amido group that can be a moiety on a polymer; and
m is 1-4;
with the proviso that the compound of Formula (I) fluoresces at least 10× the value of its base compound which is QH$_2$ not having such cyclic amides, urea, urethanes or cyclic amino amide entities present.

The compound of Formula (I) has its emissions are in the visible-near infrared region of 400-850 nm and is non-immunogenic to cells.

Preferred compounds of Formula (I) are those wherein $R^2$ is —C(O)O($C_1$-$C_4$ alkyl) or —C(O)OH, especially wherein the alkyl is methyl; wherein W is $(CH_2)_n$ where n is 1; and m is 1, especially preferred wherein Q is an amine terminated dendritic polymer or an amine terminated dendron. Some amines of Q are ($C_1$-$C_{20}$ alkyl) amine, ($C_1$-$C_{20}$ hydroxylalkyl) amine, ($C_1$-$C_{20}$ alkyl ether) amines, $C_6$-$C_{14}$ aryl or ($C_6$-$C_{14}$ aryl $C_1$-$C_4$ alkyl) amines.

In Formula (I) and as used herein and for other formulae the terms "an amido group that can be a moiety on a polymer" mean various possible groups such as:
a) polyalkylenamines (linear, cyclic, and branched): ethylenamines, propylenamines, butylenamines, hexamethyleneamines, including mixed polyalkylenamines copolymers, e.g., ethylenamine/propylenamine or butylenamine/ethylenamine copolymers;
b) polyetheramines: analogs of alkylenamines with one or more ether linkages inserted in the hydrocarbon chain (diamino polyethylene oxide), Jeffamines;
c) polyamidoamines;
d) polythioamines: sulfur analogs of polyetheramines;
e) polyaminoacids: polylysine;
f) Corcat polymers;
g) polyvinyl amine; and
h) poly(vinyl benzyl amine).

These compounds of Formula (I) are used in a method of tracing moieties and fluids in various systems, tests, plants or animals and humans by fluorescence, and monitoring or detecting the location of the moiety by its fluorescence. Thus these compounds can serve as a tracer, biosenser, or imaging agent, prevents photo-bleaching or enhances LED display.

Additional fluorescent macrocyclic amides having from 4 to 14 components of the formula

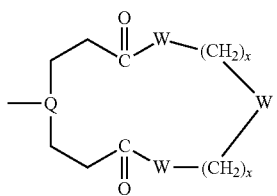

Formula (II)

wherein Q and W are defined as in Formula (I) above; and x is 2 or 3.

These compounds of Formula (II) can be used in a method of tracing moieties and fluids in various systems, tests, plants or animals and humans by fluorescence, and monitoring or detecting the location of the moiety by its fluorescence.

Similarly these compounds of Formula (II) can be used as a tracer, biosenser, labeling agent, abiotic sensor or imaging agent; prevent photo-bleaching or enhances LED display.

Some primary amines that are suitable Q moieties in Formula (I) are X—Z—N— where X is H, —OH, —NH$_2$, —SH, —CO$_2$H and Z is ($C_1$-$C_{18}$ alkyl), ($C_6$-$C_{12}$)aryl, ($C_6$-$C_{12}$)arylene, or ($C_6$-$C_{12}$)alkylarylene, such as ($C_1$-$C_{20}$ alkyl) amine; ($C_1$-$C_{20}$ hydroxylalkyl) amine; ($C_1$-$C_{20}$ alkyl) etheramines; benzylamine, or

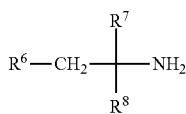

Formula (A)

where $R^6$ is —NH$_2$, —OH, or —C(O)OH, and $R^7$ and $R^8$ are independently —H or $C_1$-$C_4$ alkyl or —CH$_2$OH; a dendrimer, dendron or dendritic polymer having primary amines on its surface; a fatty/lipophilic entity with a primary amine, which when cyclized can form an amphiphilic surfactant that will lead to fluorescent micelles, a protein having a primary amine or any of the common amino acids such as lysine, glycine, tryptophan, tyrosine and/or phenylalanines.

The primary amines that are suitable Q moieties in Formula (1) entity may be presented by (1) small organic molecules, (2) oligomers and polymers which are derived from any of the four major polymer architecture types such as linear, cross-linked, branched and dendritic polymer types (DENDRIMERS, DENDRONS, AND DENDRITIC POLYMERS, Tomalia, D. A., Christensen, J. B. and Boas, U. (2012) Cambridge University Press, New York, N.Y.), including both organic and inorganic compositions (i.e., silicas, inorganic oxides, metal chalcogenides, fullerenes, etc. or (3) any of the defined Soft or Hard nano-elements (i.e., nanoparticles) as described in (Chapter 8, DENDRIMERS, DENDRONS, AND DENDRITIC POLYMERS, Tomalia, D. A., Christensen, J. B. and Boas, U. (2012) Cambridge University Press, New York, N.Y.).

Another compound of this invention, which is a subset of Formula (I), is a fluorescent compound of the formula

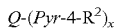

Formula (IV)

wherein:

Q is the residue of a compound having at least one primary amine that provides the nitrogen atom that becomes a part of a pyrrolidone moiety;

x is from 1 to the total number of primary nitrogens present in Q;

$R^2$ is —C(O)OH; —C(O)O($C_1$-$C_4$ alkyl); 2-oxazoline; —C(O)—NHR$^5$ wherein R$^5$ is H;

$C_1$-$C_4$ alkyl or an amido group that can be a moiety on a polymer; including pharmaceutically acceptable salts and esters of —CO$_2$H; and with the proviso that the total molecular weight is not greater than 100 KDa and the size of the compound is not greater than 15 nm.

Preferably, $R^2$ is —C(O)OH; —C(O)O($C_1$-$C_4$ alkyl); —C(O)—NHR$^5$ wherein R$^5$ is —$C_1$-$C_4$ alkyl or an amido group that can be a moiety on a polymer.

Examples of Q are ($C_1$-$C_{20}$ alkyl) amine, ($C_1$-$C_{20}$ hydroxylalkyl) amine, ($C_1$-$C_{20}$ alkyl ether) amines, $C_6$-$C_{14}$ aryl or ($C_6$-$C_{14}$ aryl $C_1$-$C_4$ alkyl) amines.

The compound of Formula (IV) is a MW controlled pyrrolidone moiety containing polymer composition that exhibits IF, low toxicity and low complement activation properties that are suitable for in vivo biological injection and imaging applications; as well as a substitute for PEG in PEGylation.

A process for preparing the compounds of Formula (IV) comprises reacting Q with a reagent of ITA, ITE or DMI, optionally in methanol, in the desired stoichiometry between the various primary amine moieties and the reagents where the resulting compound of Formula (IV) has the total molecular weight of not greater than 100 KDa, preferably not greater than 50 KDa, and the size of the compound of Formula (IV) is not greater than 15 nm, preferably 10 nm.

This invention also concerns activated PYRROLIDONylation reagents made having the Formula (III):

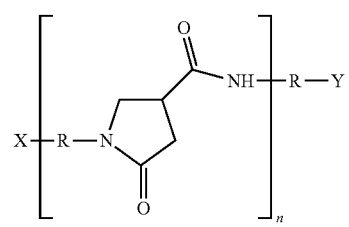

Formula (III)

wherein: R is $C_1$-$C_{18}$ alkyl, $C_6$-$C_{12}$ aryl, $C_6$-$C_{12}$ arylene, ($C_1$-$C_{12}$ alkyl) $C_6$-$C_{12}$ arylene; and X=Y is independently H, —OH, —NH$_2$, —SH, —CO$_2$H, alkyne, azido (i.e., click reagents) or any suitable reactive moiety/derivative, required for conjugating the PYRROLIDONylation reagents to desired/targeted substrates such as peptides, proteins, antibodies, enzymes, polynucleic acids, drugs, nanoparticles, microparticles, liposomes, micelles, dendrimers, dendrons, dendrimersomes, pharmaceutics, or other biological entities or fragments thereof.

Although not limited to this list, many of the demonstrated small molecule amines are illustrated in FIGS. 3A & B. Others that might be mentioned include; ($C_1$-$C_{20}$ alkyl) amines, ($C_1$-$C_{20}$ hydroxylalkyl) amine, ($C_1$-$C_{20}$ alkyl ether) amines, ($C_6$-$C_{18}$ aryl)amines or ($C_7$-$C_{21}$ arylalkyl)amines. It is desirable in all cases for these Q entities to possess appropriate conjugation and sequestering (i.e., chelation) functionality that will allow these non-traditional, intrinsic fluorophores (NTIF) structures to be chemically bonded, chelated, associated or adsorbed to a wide range of chemical surfaces, substrates, various macroscopic surfaces such as silica, metals, dental enamel, cotton, wood, food, clothing, glass, and others.

Some of these reactions can form macrocyclic fluorescent amides that are also a part of this invention. The size of the ring can have from 4 to 14 components and still provide the utility described for these compounds of Formula (I) as shown in Table 2. These macrocyclic compounds have the formula:

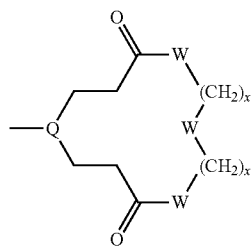

Formula (II)

wherein Q and W are defined as in Formula (I); and x is 2 or 3.

These rings are formed from a general process by reacting a compound of the formula

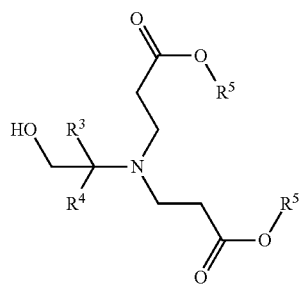

Formula (B)

where $R^5$ is $C_1$-$C_4$ alkyl; $R^3$ and $R^4$ are defined as above, with EDA, DETA, TETA, etc. The process provides 7-, 11-, 14-member amide rings. See FIG. 2. While not wishing to be bound by theory, it is believed that 14-member rings form during the process in Examples 18 and 23 having the possible formulas of

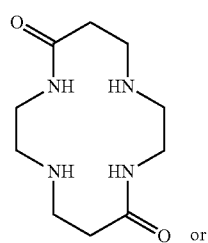

Formula (C)

or

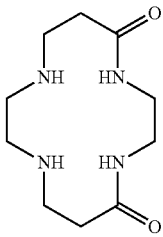

Formula (D)

and of the formula

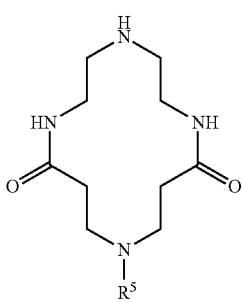

Formula (E)

for Examples 5, 15 and 29.

When EDA is reacted with 2 equivalents of dimethyl itaconate a dimer is formed that fluoresces. But when 1 equivalent of dimethyl itaconate is reacted with EDA, then a polymer that fluoresces is formed. Thus depending on the conditions, the size of the resulting fluorophore can be controlled.

Thus macrocyclic amides and polymers with amide groups in various rings can be made and used depending of the properties for use, the intensity of the fluorescence desired and the emission wave length from blue to near infared obtained.

Another aspect of this invention provides a compound of the formula

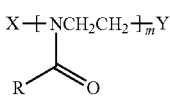

Formula (V)

wherein:
R is a pyrrolidone functionalized moiety;
X is selected from click moieties; such as propargyl, azide, allyl or any moiety which may be selectively reacted with Z or W of Formula (VI) as defined below to produce a mono functional copolymeric adduct suitable for conjugating to drugs, proteins or clinically relevant substrates;
Y is selected from click moieties; such as propargyl, azide, allyl, or any moiety (i.e., thiol, maleimide, amine, ester, activated ester, respectively, or in a protected form) which may be selectively reacted with or Z or W of Formula (VI) as defined below to produce a mono functional adduct suitable for conjugating to drugs, proteins or clinically relevant substrates; and $m$=1–150.

Another aspect of this invention provides a compound of the formula

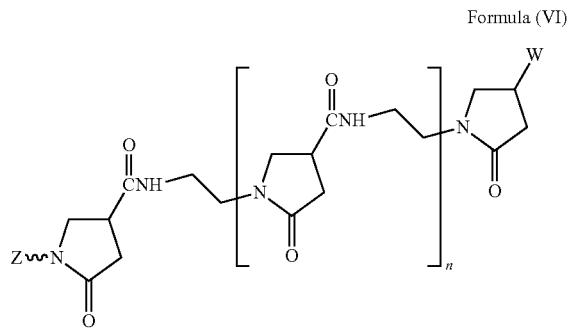

Formula (VI)

wherein:

Z is selected from click moieties; such as propargyl, azide, allyl or any moiety (i.e., thiol, maleimide, amino, ester, activated ester, respectively, or in a protected form) which may be selectively reacted with X or Y from Formula (V) as defined above to produce a mono-functional copolymeric adduct suitable for conjugating to drugs, proteins or clinically relevant substrates;

W is thiol, maleimide, amino, ester, azide, allyl, respectively, or in a protected form, derived in each case from the ester moiety (—$CO_2Me$), which may be selectively reacted with X or Y from Formula (V) as defined above to produce a mono-functional adduct suitable for conjugating to drugs, proteins or clinically relevant substrates; and n is 1-150.

These compounds of Formula (I)-(VI) are fluorescent after excitation and used as tracers in medicine for cellular imaging, biosensing, fluorescence directed surgical resections and drug delivery. Applications of fluorescence outside of biology/medicine uses include, but are not limited to: forensics; mineral/gemstone characterization; oil field enhancement and diagnostics, counterfeit goods detection; tracer studies related to liquid/water flow; prevention of photo-bleaching; and LED display enhancements. Thus this invention provides a method of tracing moieties and fluids, and monitoring location in systems for such detection by fluorescence using a compound of Formula (I).

BRIEF DESCRIPTION OF THE DRAWINGS

The patent or application file contains at least one drawing executed in color. Copies of this patent or patent application publication with color drawing(s) will be provided by the Office upon request and payment of the necessary fee.

DETAILED DESCRIPTION OF THE INVENTION

Figure 1:
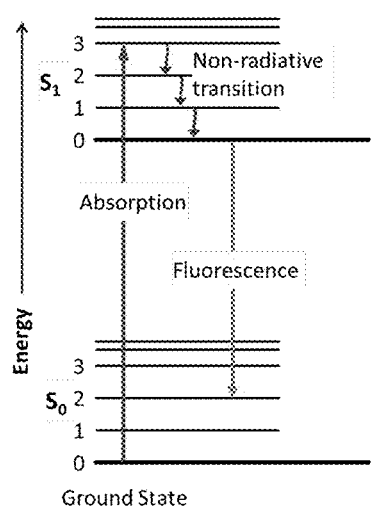
FIG. 1 illustrates the excitation of a compound in its ground state with energy to an elevated state and relaxes by fluorescence emission back to the ground state.

It is understood that the terminology used herein is for the purpose of describing particular embodiments only and is not intended to be limiting. As used in this specification, the singular forms "a", "an", and "the" include plural referents unless the content clearly indicates otherwise. The following terms in the Glossary as used in this application are to be defined as stated below and for these terms, the singular includes the plural.

Various headings are present to aid the reader, but are not the exclusive location of all aspects of that referenced subject matter and are not to be construed as limiting the location of such discussion.

Also, certain US patents and PCT published applications have been incorporated by reference. However, the text of such patents is only incorporated by reference to the extent that no conflict exists between such text and other statements set forth herein. In the event of such conflict, then any such conflicting text in such incorporated by reference US patent or PCT application is specifically not so incorporated in this patent.

Glossary

The following terms as used in this application are to be defined as stated below and for these terms, the singular includes the plural. The bold font is not required to meet this definition but to more easily find the term's meaning in this listing.

AEEA means N-(2-hydroxyethyl)ethylenediamine
AEP means 1-(2-aminoethyl)piperazine
Alkyl means straight and branched chain moieties unless otherwise indicated
BOC means tert-butoxycarbonyl
BSA means bovine serum albumin
4-CP-PAMAM means 4-carbomethoxy pyrrolidone terminated PAMAM dendrimers
Da means Daltons
DAB means 1,4-diaminobutane
DABCO means 1,4 diazabicyclol [2.2.2]octane
DBA means dibenzylamine
DBI means dibutyl itaconate DEA means diethanolamine
Dendritic polymers means the dendritic polymer class of random hyperbranched, dendrigraft, dendron or dendrimer polymers, including core-shell tecto-dendrimers
DETA means diethylenetriamine
DMDTB means dimethyldithiobutyrate
DMEM means Dulbecco's Modified Eagle Medium
DMI means dimethyl itaconate
DNA or RNA or Nucleic Acids means synthetic or natural, single or double stranded DNA or RNA or PNA (phosphorous nucleic acid) or combinations thereof or aptamers, preferably from 4 to 9000 base pairs or from 500 D to 150 kD
DP means degree of polymerization
EA means ethanolamine
EDA means ethylenediamine
EEM means excitation-emission matrix
equiv. means equivalent(s)
FBS means fetal bovine serum
FT-IR means Fourier Transform Infrared Spectroscopy
FWA means fluorescent whitening agents
G means dendrimer generation, which is indicated by the number of concentric branch cell shells surrounding the core (usually counted sequentially from the core)
g means gram(s)
h means hour(s)
halo means fluoro, chloro, bromo, or iodo atom, ion or radical
Soft or Hard nano-elements mean nanoparticles as defined in "A Systematic Framework and Nanoperiodic Concept for Unifying Nanoscience: Hard/Soft Nanoelements, Superatoms, Meta-Atoms, New Emerging Properties, Periodic Property Patterns, and Predictive Mendeleev-like Nanoperiodic Tables, D. A. Tomalia, S. N. Khanna, Chem. Rev., 16, 2016, 2705-2774
HB-PEI means hyperbranched-polyethyleneimine
HEDA means (2-hydroxyethyl)ethylenediamine
HMDA means hexamethylenediamine
IA or ITA means itaconic acid
IF means intrinsic fluorescence
IR means infrared spectroscopy
ITE means itaconic ester
L means liter(s)
L-PEI means linear-poly(ethyleneimine)
MeOH means methanol
mg means milligram(s)
min means minutes(s)
mL means milliliter(s)
MW means molecular weight
μm means micrometer(s)
nm means nanometer(s)
NTF means non-traditional fluorescence
NTIF means non-traditional, intrinsic fluorescent
N-VP means N-vinyl pyrrolidone monomer
PAMAM means poly(amidoamine), including linear and branched polymers or dendrimers with primary amine terminal groups; Starburst™ (trademark of Dendritic Nanotechnologies, Inc.)
PBS means phosphate buffered saline
PEG means poly(ethyleneglycol)
Percent or % means by weight unless stated otherwise
PETIM means poly(propyl ether imine)
PIPZ means piperazine or diethylenediamine
PPI means poly(propyleneimine) dendrimers
PVP means poly(vinylpyrrolidone)
Pyr or Pyrr means pyrrolidone or pyrrolidinone
PyrAM means pyrrolidone amines
rpm means rotation per minute, the frequency of agitation in a shaking water bath
RBF means round bottomed flask
RT means ambient temperature or room temperature, about 20-25° C.
Stealth means non-immunogenic to cells
TETA means triethylenetetramine
TMS means tetramethylsilane
Tracer means a compound used to track the progress or history of a natural process or presence of a compound, such as a histochemical tracer for the study of the composition of cells and tissues; a flow tracer for any fluid property used to track fluid motion; a dye tracer; or any compound that can be located in the environment where it is used.
TREN means tris(2-aminoethyl)amine
TRIS means tris(hydroxymethyl)aminomethane
UV-vis means ultraviolet and visible spectroscopy
Discussion
PYRROLIDONylation In view of the extensive positive experience of using PVP as an injectable synthetic polymer in humans (i.e., >75 years in >500,000 human subjects) without any known physiological problems except with higher molecular weight fractions (i.e., >20 KDa; see below), this invention's use of these pyrrolidone compositions are as alternatives to either PEGylation or POxylaton. Both PEGylation and POxylaton have their own deficiencies and unarguably far less in vivo documentation in humans than PVP's. Furthermore, an added feature of these new pyrrolidone analogues of PVP over PEGylation and POXylation products is their unexpected intrinsic fluorescence properties. These fluorescence properties have been demonstrated to be invaluable for imaging biologic cells and monitoring in vivo transport and biodistribution. Consistent with historical terminology, these new protocols for modifying polynucleotides, peptides, proteins, drugs, and other entities are now referred to as PYRROLIDONylation. A general structural representation of these PYRROLIDONylation reagents is as illustrated below in Formula (III).

These PYRROLIDONylation repeat units may be effectively integrated into any of the four major polymeric architectures including: (a) Linear, (b) Cross-linked, (c) Branched or (d) Dendritic, wherein: the degree of polymerization (DP)=(n) is generally 4-100 and X or Y can be independently reactive or non-reactive with functionality possessed by the desired protein, polypeptide, polynucleotide or therapeutic drug to be modified.

This invention describes such a scientific solution that remediates this widely recognized dilemma by providing well defined, discrete, low molecular weight (i.e., <100 KDa, preferably <50 KDa or <20 KDa) oligomers/polymeric analogues of PVP that should be excretable by the kidney and suitable for a wide variety of injectable biomedical applications. As such, these discrete functionalized, low molecular poly(pyrrolidones) also become excellent and viable candidates for use as alternatives or replacements for PEG reagents based on their extensive and largely safe medical use over the past 75 years as injectable blood substitutes/extenders. Furthermore, it has been determined that many of these new small molecule and polymeric pyrrolidone compositions exhibit important unexpected fluorescent properties that are not explicable according to traditional photochemistry paradigm, however, this new fluorescence property has been documented to be very valuable and useful for imaging biological cells and monitoring in vivo transport and distribution within an organism.

This present invention now describes novel methods and strategies to produce well defined, low molecular weight poly(pyrrolidone) oligomers possessing highly desirable terminal end group "active drug conjugation functionality sites" that remediate all of the above concerns and shortcomings associated with the use of pyrrolidone compositions for in vivo drug delivery applications. In the spirit and context of terminology used for PEG's and POx's, these new protocols and reagents are termed PYRROLIDONylations. General examples of these activated PYRROLIDONylation reagent are as described below:

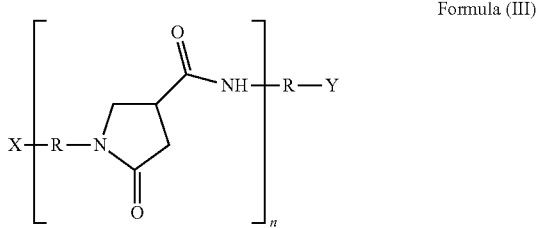

Formula (III)

wherein: R is $C_1$-$C_{18}$ alkyl, $C_6$-$C_{12}$ aryl, $C_6$-$C_{12}$ arylene, ($C_1$-$C_{12}$ alkyl) $C_6$-$C_{12}$ arylene; and X=Y is independently H, —OH, —$NH_2$, —SH, —$CO_2H$, alkyne, azido (i.e., click reagents) or any suitable reactive moiety/derivative, such as those described by G. T. Hermanson, Chapters 1-27 (pp 3-1039) in Bioconjugate Techniques, Second Ed., (2008), required for conjugating the PYRROLIDONylation reagents to desired/targeted substrates such as peptides, proteins, polynucleic acids, drugs, nanoparticles, liposomes, dendrimers, pharmaceutics, or other biological entites.

Pharmaceutically acceptable salts and esters of —$CO_2H$ are also included as a compound of Formula (III). These salts and esters are well-known to those persons skilled in drug development and available from the acceptable lists for approved drugs from the FDA for many drugs.

The present invention describes new pyrrolidone polymer compositions (i.e, linear, branched, cross-linked and dendritic architectures), including well defined small molecule pyrrolidone intermediates, with strategies/protocols for their syntheses that permit obtaining unique, well defined pyrrolidone polymer compositions that allow molecular weight (MW) control, especially as oligomers or low molecular weight polymeric compositions. This can be understood by FIG. 10.

Presently, such oligomeric/low MW polymeric pyrrolidone compositions are not available by any known polymerization protocols (Pfirrmann et al., U.S. Pat. No. 6,080, 397, 2000; www.rloginconsulting.com/ . . . pyrrolidone%20backbone%20polymers.pdf). The novel, controlled low MW pyrrolidone polymers that constitute the present invention provide dramatically enhanced alternatives to traditional PEGylation (i.e., poly(ethyleneglycol) polymers as discussed above. The PEG polymers possess certain negative property features (i.e., oxidative instability, immunogenic properties) among others. More recently, POXylation (i.e., poly(oxazoline) (J. Milton Harris et al., U.S. Pat. No. 8,088,884, (Jan. 3, 2012) protocols. These PEGylation and POxylation protocols involve covalent attachment or association of poly(ethyleneglycols) or poly-oxzaolines with various proteins, enzymes, drugs or imaging agents in a wide range of in vivo drug delivery and imaging applications. The conjugation of biopharmaceuticals to PEG by PEGylation protocols has led to clinical/marketing success of a number of significant, commercially important macromolecular drugs for the treatment of hepatitis C, neutropenia and anemia (F. M. Veronese, A. Mro, G. Pausut, (2009) "*Protein PEGylation, Basic Science and Biological Applications. PEGylated protein, drugs; basic science and clinical applications, milestones in drug therapy series*" F. M. Veronese, Ed., pp 11-31, Birkhauser Verlag, Berlin).

In the context and spirit of these earlier technologies, this new poly(pyrrolidone) based technology described by the present invention is named as (PYRROLIDONylation) (i.e., poly(pyrrolidone) protocols. These linear-poly(amidopyrrolidone) (PAMPyr) products are analogues to PEGs (Davis et al., *Adv. Drug Delivery Reviews*, 2002, 54(4), 457-458) and PEOx (Harris et al., U.S. Pat. No. 7,943,141, 2011) type polymers. As such they exhibit low toxicity, low complement activation features and may be used to reduce protein interactions with drug conjugates while enhancing in vivo residency times for these conjugates when used as injectables. These new poly(pyrrolidone) compositions were exhibited amazingly low toxicity [Ciolkowski et al., *Nanomedicine, NBM*, (2012), 8, 815-817; Janaszewska et al., *Nanomedicine, NBM*, (2013), 9, 461-464] and low complement activation (i.e., low immunogenic properties) with in vivo stealth properties [N. Spyropoulos-Antonakkakis et al., *Nanoscale Research Letters*, (2015); 10:210) exceeding those properties recognized for traditional PEGylation protocols. Unexpectedly, many of these new, small molecule pyrrolidone intermediates and their resulting poly(pyrrolidone) (PVP) compositions were found to exhibit new, non-traditional "intrinsically fluorescence" properties suitable for in vivo imaging of biological cells or tracking physiological movement and biodistributions in organisms and animal models.

Very recently it has been reported that pyrrolidone terminated PAMAM dendrimers are truly unique compared to all other nanoscale particles due to their very low toxicity (Ciolkowski et al., *Nanomedicine, NBM*, 2012, 8, 815-817; Janaszewska et al. *Nanomedicine, NBM*, 2013, 9, 461-464), negligible complement activation properties (N. Spyropoulos-Antonakkakis et al., *Nanoscale Research Letters*, (2015); 10:210) and quite remarkably the unprecedented ability to selectively target human atheromatous carotid tissue (i.e., cardiovascular plaque) (N. Spyropoulos-Antonakkakis et al., *Nanoscale Research Letters*, (2015); 10:210).

Process Discussion

Figure 11:
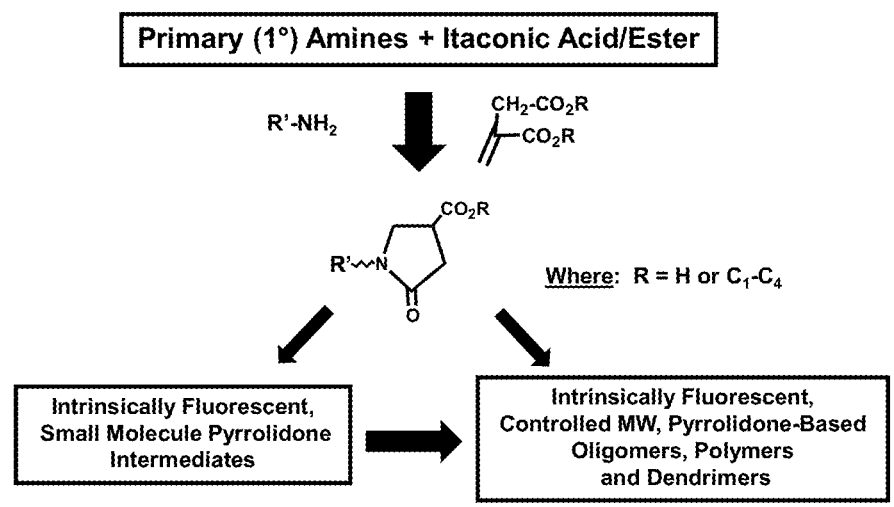
FIG. 11 illustrates a process for synthesizing intrinsically fluorescent, small molecule pyrrolidone intermediates as shown by Scheme 2.

Methods/Processes for Synthesizing Intrinsically Fluorescent, Small Molecule Pyrrolidone Intermediates, Oligomers and Polymers as Alternate Replacements for PEGylation Reagents These small pyrrolidone molecules are readily prepared by a simple process involving the reaction of primary amines with itaconic acid or its derivatives (i.e., esters, amides, anhydrides). This general primary amine+itaconic acid derivative reaction scheme may be used to control the MW of these pyrrolidone intermediates as well as the MW's of desired low molecular weight pyrrolidone polymers, all of which exhibit unexpected intrinsic fluorescence (IF) suitable for in vivo applications. These strategies are illustrated with the following flow diagram (in FIG. 11).

In this scheme, R is H or $C_1$-$C_4$ alkyl; R' is C1-C18 alkyl.

The synthetic strategies used to synthesize heterocyclic/ macrocyclic (i.e., pyrrolidone) rings for this invention generally involves the reaction of mono- and poly-1° amines with itaconic acid (ITA), itaconic esters (ITE) such as DMI, or itaconic anhydride. In all cases the stoichiometry between various 1° amine moieties and the itaconic acid reagents was very critical. These stoichiometries could be systematically adjusted to produce a wide diversity of 4-carboxylic acid/ester pyrrolidone categories. These categories included: (1) simple molecular structures, (2) bicyclic/oligomeric/macrocyclic structures or (3) polymeric pyrrolidone product types.

These high yield reactions between simple small molecule primary amines and itaconic acid derivatives were very readily extended to all polymeric architectures bearing primary amines, including dendrimers as well as linear polymers i.e., poly(vinylamines) and poly(allyamines).

The first reaction to form an IF small molecule pyrrolidone intermediate shown by (A) in Scheme 2 requires at least one primary amine such that a monoamine, diamine, triamine molecule can be R, then that amine is reacted with itaconic acid (ITA) or itaconic ester (ITE). Any primary monoamine can be used such as 2-aminoethanol, aminoethylethanolamine (AEEA), tris-hydroxylmethyl amine (TRIS), glucosamine, glycine, dodecylamine, or other desired monoamine. The stoichiometry is:

1° Amine Moiety: ITA/ITE

[1:1]→2-R(X) Substituted-4-Carboxy Pyrrolidones
[2:1]→2-R(X)-Substituted-4-Carboxyamido Pyrrolidones The resulting product has IF and is (A) in Scheme 2.

When a diamine, having 2 primary amines, reacts with ITA or ITE then two pyrrolidone rings can form per diamine Examples of these primary diamines are ethylene diamine (EDA), Cystamine (CYS), diethylene triamine (DETA), triethylene tetraamine (TETA), or other desired diamines. The stoichiometry may be:

1° Diamine Moiety: ITA/ITE

[1:1]→R(X) Substituted-4-Carboxy Pyrrolidone Backbone Macrocyclics, Oligomers, Polymers
[4:1]→2-R(X)-Substituted-4-Carboxyamido Pyrrolidones
[1:2]→2-[-R(X)-]-Substituted-4-Carboxyamido Di-Pyrrolidones In this latter case, one may perform this [1:2] reaction on cystamine to form the dipyrrolidone intermediate from which one can perform dipyrrolidone sequential iterations with excess EDA followed with DMI. This iterative sequencing yields important thiol protected linear-PAMPyr oligomers of desired lengths that are of high importance for PYRROLIDONylation of various biological substrates as illustrated below:

Linear-Poly(Amido Pyrrolidone) (L-PAMPyr)-Trimer

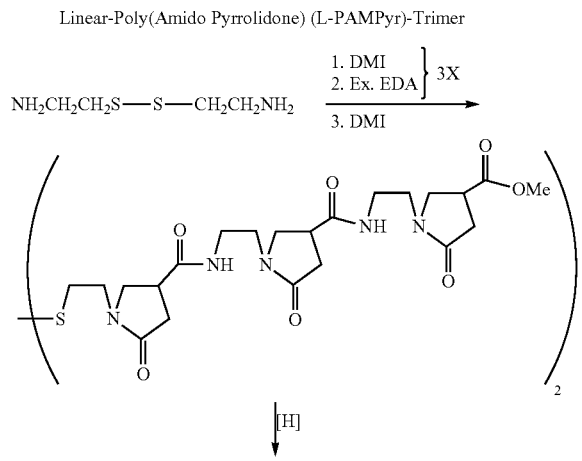

Alternatively one may perform iterative DMI+excess EDA sequencing on a BOC protected diamine, in which case the number of iterations would determine the length of the PYRROLIDONylation reagent. Of course traditional Merrifield like substrates may also be used for similar protection of such a diamine That withstanding, appropriate endgroup modifications, cleavage from the resin and or de-protection of the BOC group would provide selective functionalization of these PYRROLIDONylation reagents for suitable conjugation to all desired biological substrates or targets according to procedures described extensively by G. Hermanson (G. T. Hermanson, in *Bioconjugate Techniques*, Second Ed., (2008).)

Pyrrolidone Oligomers

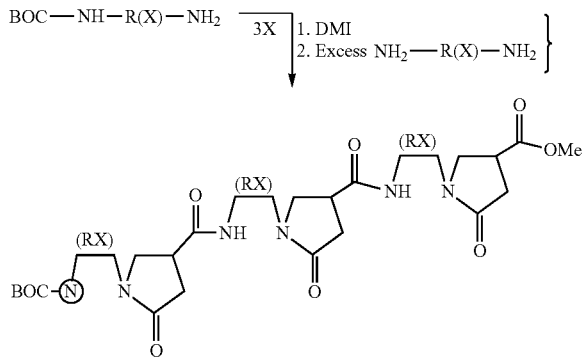

When a triamine, having 3 primary amines, reacts with ITA or ITE then three pyrrolidone rings may form per triamine. An example of these primary triamines is tris(2-aminoethyl) amine (TREN) or other desired triamines. The stoichiometry is:

1° Triamine Moiety: ITA/ITE

[1:1]→Tri-Substituted-[2-R(X), 4-Carboxylic acid/ester Pyrrolidones]

N—[(CH₂—CH₂—NH₂)]₃ (TREN)+3 DMI→N—[(CH₂—CH₂—N(4-carboxyl acid/ester) Pyrrolidone]₃

It should be noted that the first tri-pyrrolidone reaction product formed in this approach may be used as a reactive scaffolding for synthesizing, MW/structure controlled 3-arm branched, star type PYRROLIDONylation reagents. The iteration steps shown below produces the star branched, poly(pyrrolidone) oligomeric product containing nine pyrrolidone rings.

Pyrrolidone-Based Star Branched PAMAM Polymers
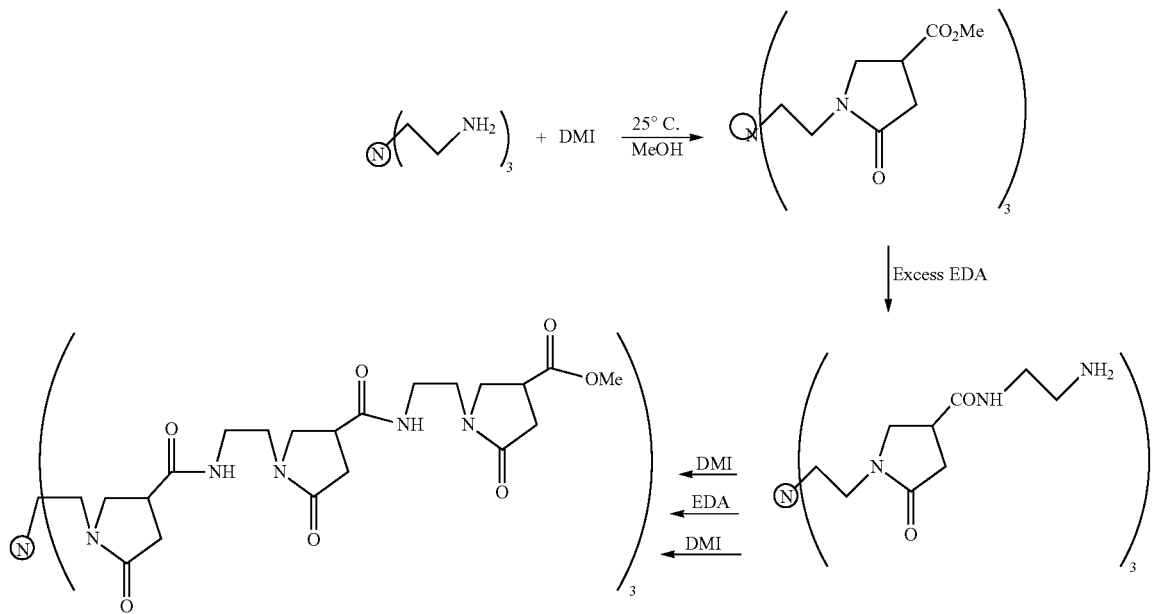
By extending this DMI+EDA iteration strategy to an amine terminated dendrimer series, one can make the corresponding dendrimer presenting NcNb$^G$ poly(linear) branches as a function of the generation level as illustrated below:

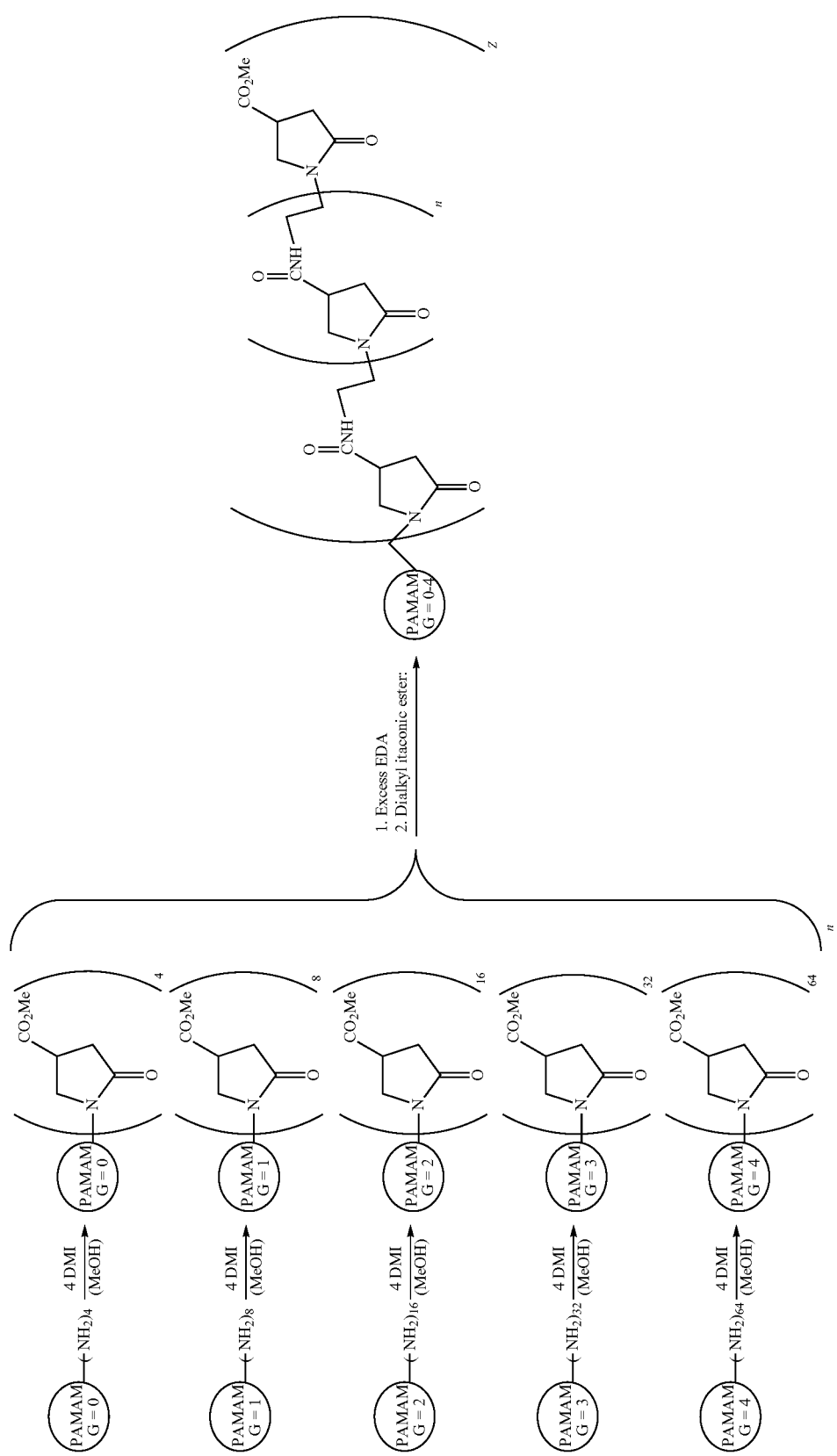

Similarly, one can produce an analogous well defined, tri-dendron type dendrimer structure by merely replacing ethylenediamine (EDA) with tri-(2-aminoethyl) amine (TREN). By using a similar iteration sequence with TREN as above with EDA produces three dendrons around the central N-core of TREN as shown below:

Dendritic-Poly(amido) Pyrrolidone Amines (PAMPyrAMs)

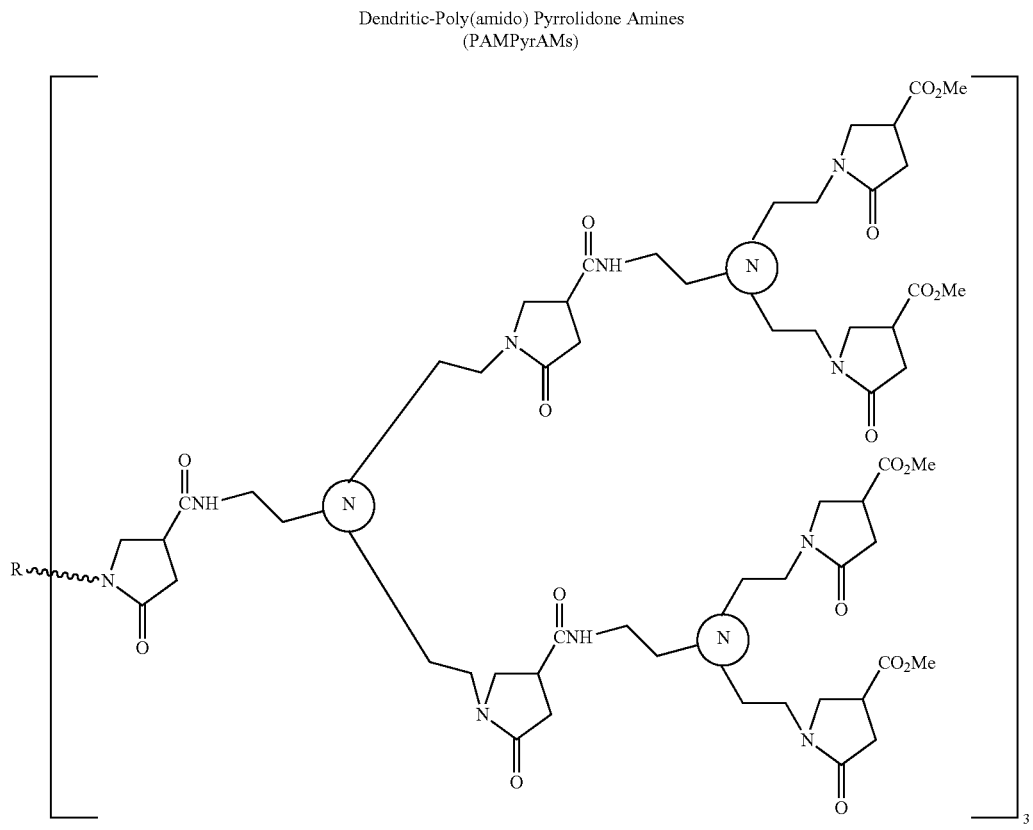

Where: R = TREN; $N_{c=3}$

This new unprecedented G=2; tri-dendron dendrimer structure contains exactly 21-pyrrolidone rings and is referred to as a representative member of the poly(amidopyrrolidone amine) (PAMPyrAM) family

[1:2]→Mono(NH$_2$)—R(X)-Substituted-Di-(4-Carboxyamido Pyrrolidones)→Hyperbranched-R(X)-Substituted-poly-(4-Carboxyamido Pyrrolidone N—[(CH$_2$—CH$_2$—NH$_2$)$_3$+2 DMI→N—[(CH$_2$—CH$_2$—NH$_2$) [(4-carboxylic acid/ester)pyrrolidone]$_2$→Hyperbranched-Pyrrolidones

[2:1]→Di-(NH$_2$)—R(X)-Substituted-Mono-(4-Carboxyamido Di-Pyrrolidones)→Hyperbranched-R(X)-Substituted-poly-(4-Carboxyamido Pyrrolidones)

N—[(CH$_2$—CH$_2$—NH$_2$)$_3$+1 DMI→N—[(CH$_2$—CH$_2$—NH$_2$)$_2$[(4-carboxylic acid/ester) pyrrolidone]→Hyperbranched Pyrrolidones In Scheme 2, when (B) polymers are formed, they have their MW controlled by this process and are pyrrolidone polymer compositions exhibiting IF, low toxicity and low complement activation properties suitable for in vivo biological injection and imaging applications. All polymer contain pyrrolidone moieties in their structure, namely as a surface group(s) or as a part of the structure of the amine that is reacted with ITA, ITC or DMI or both in the structure and on the surface or the polymer. These polymeric compositions can be produced in four different architectural forms, namely; (a) Linear Polymers, (b) Cross-linked Polymers, (c) Branched Polymers, and (d) Dendritic Polymers.

Linear-Pendant Pyrrolidone Oligomers/Polymers:
1°-Polyamines [RX—(NH$_2$)$_z$]+ITA or ITE→

In the above reaction some primary polyamines are poly (vinyl amine), poly(allylamine), poly(vinylbenzylamine) or other suitable polyamines having 1 or more primary amines; and Z=degree of polymerization (DP). The stoichiometry is:
[1° Amine moiety: ITA/ITE]=[1:1]
[1:1]→Linear-[Poly-2-(R(X))-Substituted-4-Carboxylic acid/ester Pyrrolidones]$_{DP=n}$ Linear-Pyrrolidone Oligomers

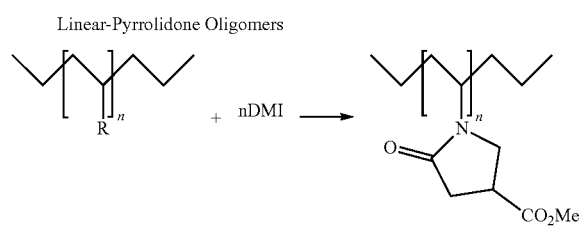

Where: R = —NH$_2$, —CH$_2$—NH$_2$, benzyl-NH$_2$, etc.

Cross-linked, Linear-Pendant Pyrrolidone Polymers:
[1° Amine Moiety: ITA/ITE]=[DP: DP-x]
[DP: DP-x]→Cross-Linked-[2-(R(X))-Substituted Poly-4-Carboxylic acid/ester Pyrrolidones]$_{DP-x}$ One can readily form cross-linked versions of the above linear-pendant pyrrolidone oligomers/polymers (shown above) by simply adjusting the ratio of DMI to primary amine so that the DMI:primary amine stoichiometry is <1:1.

Linear-Pendant Branched Pyrrolidone Polymers

Linear-Pendant Branched Pyrrolidone Polymers

Figure 10:
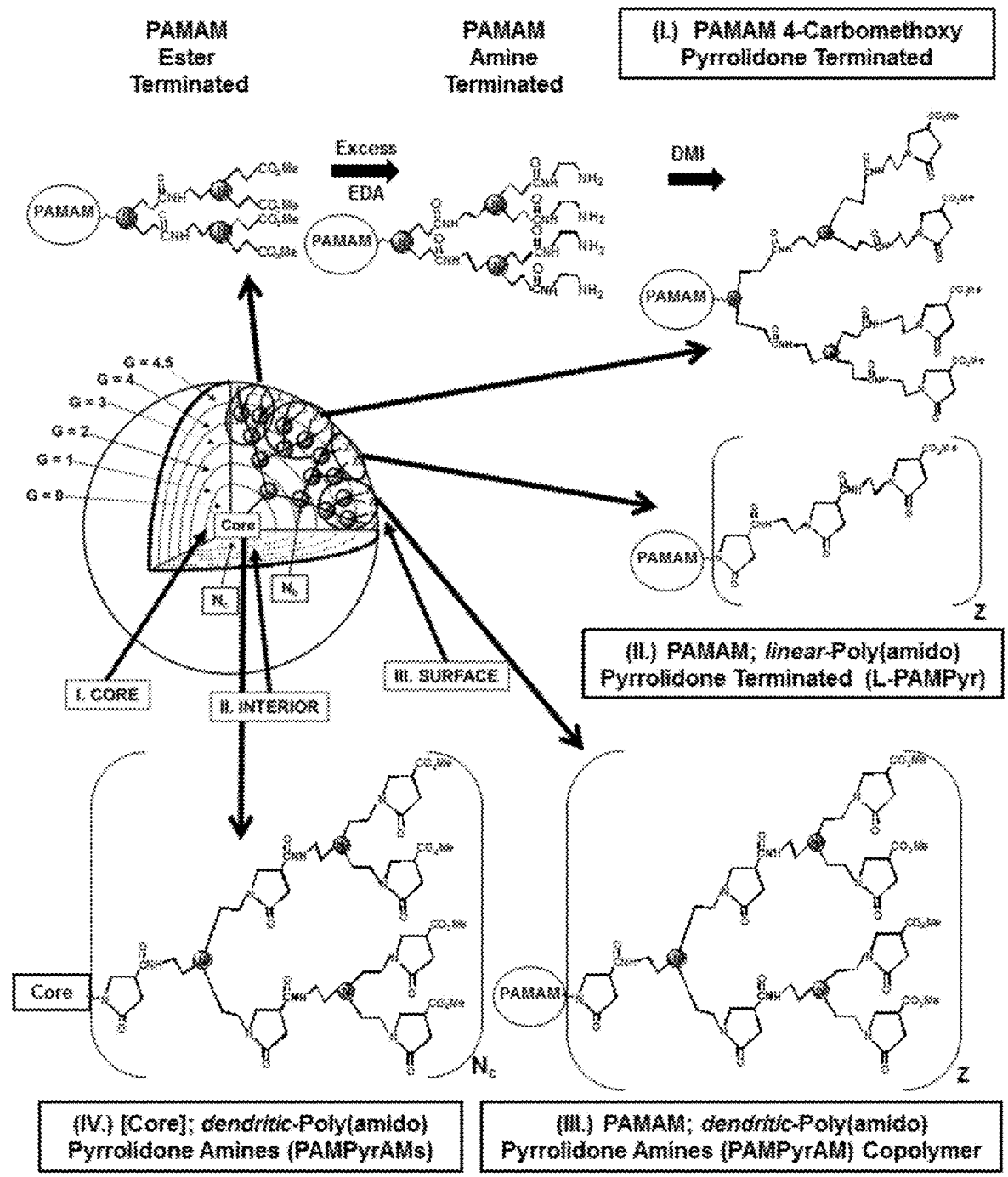
FIG. 10 illustrates the comparison between PAMA dendrimers and the pyrrolidones of this invention.

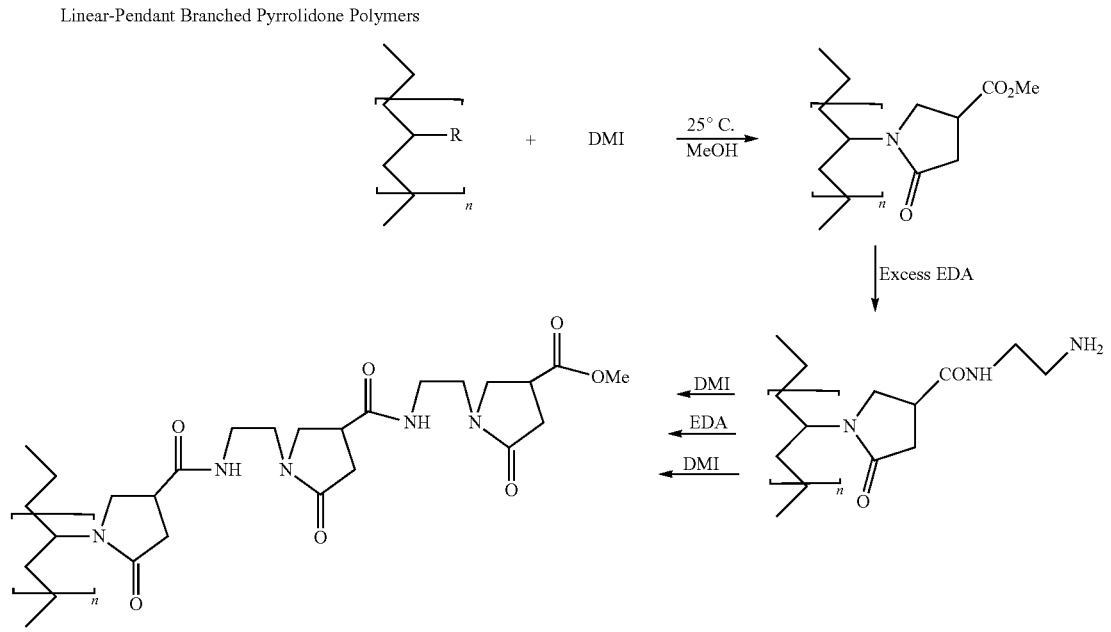

cesses developed for dendron/dendrimer based systems it has been possible to synthesize at last three new poly (pyrrolidone) compositions that may be designed and engineered according to mathematically driven principles/expressions as described below and illustrated in FIG. 10.

Figure 12:
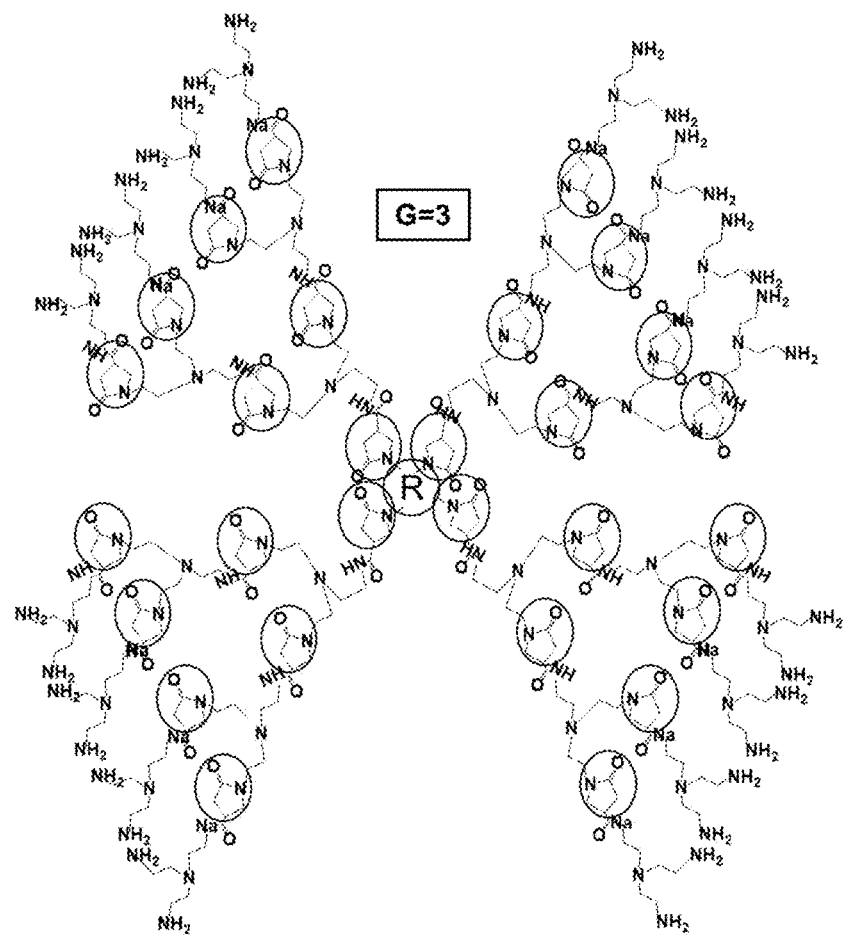
FIG. 12 illustrates a chemical structure of a dendri-{poly (amidopyrrolidone) amine}-$(NH_2)_z$; G=3; (PAMPyrAM) dendrimer derived from a core=R=[DAB]; where: $N_c$=4, contains exactly 28-pyrrolidone rings.

Dendritic Core-Dendritic Surface Poly(Pyrrolidone) Copolymeric Dendrimers:

As shown above, one may grow pure, all poly(pyrrolidone) based dendrons by performing iterative reaction sequences using [1:1] DMI stoichiometry followed by using excess TREN starting from simple, small molecule primary amine cores such as tris-(2-aminoethyl) amine (i.e.,TREN), ethylene diamine (EDA), 1,4-diaminobutane (DAB), etc. Such a dendri-{poly(amidopyrrolidone) amine}-$(NH_2)_z$; G=3; (PAMPyrAM) dendrimer derived from a core=R= [DAB]; where: $N_c$=4, contains exactly 28-pyrrolidone rings and is as illustrated in FIG. 12.

Alternatively, one may grow dendri-poly(pyrrolidone) type dendron components from the surface of primary amine terminated dendrimers derived from any desired interior dendrimer composition to produce new, unprecedented [dendri-1]-[dendri-2 (pyrrolidone)] type copolymeric dendrimers. This strategy assures complete mathematical control over the total number of pyrrolidone rings that may be introduced as a function of generation and may be predicted according to the traditional expression; $Z=N_c N_b^G$ were Z=the number of pyrrolidone rings introduced per generation. Therefore total control over the number of pyrrolidone rings desired in a particular PYRROLIDONYlation reagent structure may be designed and engineered according to the below mathematics.

One the most important aspects of this invention is the ability to engineer and control molecular weights of poly (pyrrolidone) oligomers, polymers, dendrons and dendrimers. Applying well documented iterative principles/pro- (I). Traditional Dendri-PAMAM-4-Carbomethoxy Pyrrolidone Terminated Dendrimers
Traditional PAMAM dendrimer; # of terminal primary amines=$Z=N_c N_b^G$
Total # of terminal pyrrolidone moieties=$P=Z=N_c N_b^G$
(II). Dendri-PAMAM: linear-Poly(amidopyrrolidone) Terminated; (L-PAMPyr) Copolymer; (linear chain modified surface; chain length=n)
Total # of pyrrolidone moieties=$P=nZ=nN_c N_b^G$
(III). Dendri-PAMAM: dendritic-Poly(amidopyrrolidoneamines); (PAMPyrAM) Copolymer
Assumptions:
# of base PAMAM dendrimer terminal primary amines=$Z=N_c N_b^G$
# of PAMPyrAM) surface generations defined by G' and $N'_b$
(Single pyrrolidone as above G'=0)
Total # of surface pyrrolidone moieties=$P_z=Z\ N'_b{}^{G'}=N_c N_b^G N'_b{}^{G'}$
Total # of interior+surface pyrrolidone moieties=$P=Z(N'_b{}^{G'+1}-1)/(N'_b-1)$
Total # of interior+surface pyrrolidone moieties=$N_c N_b^G (N'_b{}^{G'+1}-1)/(N'_b-1)$
(IV). [Core]: dendritic-Poly(amidopyrrolidoneamines) (PAMPyrAMs)
Assumptions:
Total pyrrolidone dendrimer (G' and $N'_b$ as above)
Total # of surface pyrrolidone moieties=$P_z=N_c(N'_b)^{G'}$
Total # of interior+surface pyrrolidone moieties=$P=N_c(N'_b{}^{G'+1}-1)/(N'_b-1)$
1°-Polyamine Terminated Dendrimers (i.e., Where: Dendrimer-$(NH_2)_z$=[Core; $(N_c)$]; [Interior; $(N_b)$]; [Terminal Groups; (Z)])
There must be at least 1 primary amine on the surface of the dendrimer as a Z moiety available for the reaction with ITA, ITE or DMI. Some possible dendritic structures are poly(amidoamine) (PAMAM) dendrimers, poly(propyleneimine) (PPI) dendrimers, poly(lysine) dendritic polymer and others [DENDRIMERS, DENDRONS, AND DENDRITIC POLYMERS, Tomalia, D. A., Christensen, J. B. and Boas, U. (2012) Cambridge University Press, New York, N.Y.]; and $Z=N_cN_b^G$). The stoichiometry is:

[1° Amine Moiety: ITA/ITE]=[1:1]

[1:1]→[Dendrimer]-[(2-Substituted-4-Carboxylic acid/ester) Pyrrolidones)]$_z$ where $Z=N_cN_b^G$.

The generation of the dendrimer can be G=0, 1, 2, 3, 4 (e.g. PAMAM) which is reacted with DMI and methanol to form the desired number of pyrrolidone moieties on the surface in accordingly from 1 to the maximum number of amines available on the surface (i.e., 4, 8, 16, 32, 64, respectively). This is generalized by the following:

[(1° Amine moieties)x: (ITA/ITE)y]=[X:Y] as a function of dendrimer generation (G) so that when Core=$N_c$=4) then (X), (Y) result as shown in Table 1.

TABLE 1

| Core (G) | Z | (X) | (Y) |
|---|---|---|---|
| 0 | 4 | [1-3] | [3-1] |
| 1 | 8 | [1-7] | [7-1] |
| 2 | 16 | [1-15] | [15-1] |
| 3 | 32 | [1-32] | [32-1] |
| 4 | 64 | [1-63] | [63-1] |
| 5 | 128 | [1-127] | [127-1] |

Figure 8:
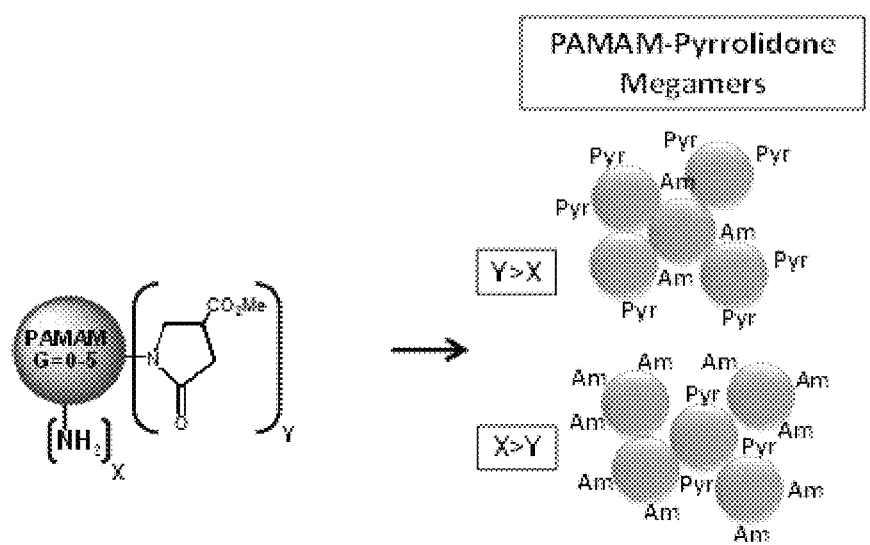
FIG. 8 illustrates the structure for random PAMAM PyrAm megamers.

Megamers:

Random-Structured Dendrimer PyrAm Megamers:

A wide range of Random-Structured Dendrimer Pyrrolidone Amine (PyrAm) megamers are readily produced by adjusting the stoichiometries of the 1° amine component (X) and the (ITA or ITE) component (Y) on any amine terminated dendrimer. More specifically, adjusting these (X) and (Y) ratios as a function of PAMAM dendrimer generation (G) as shown above in Table 1, will lead to the random structured PAMAM-PyrAM megamers. When Y>X, the megamer will present a predominance of pyrrolidones moieties on the surface. When X>Y the megamers will present a predominance of 1° amine groups. These megamers are shown in FIG. 8.

Figure 9:
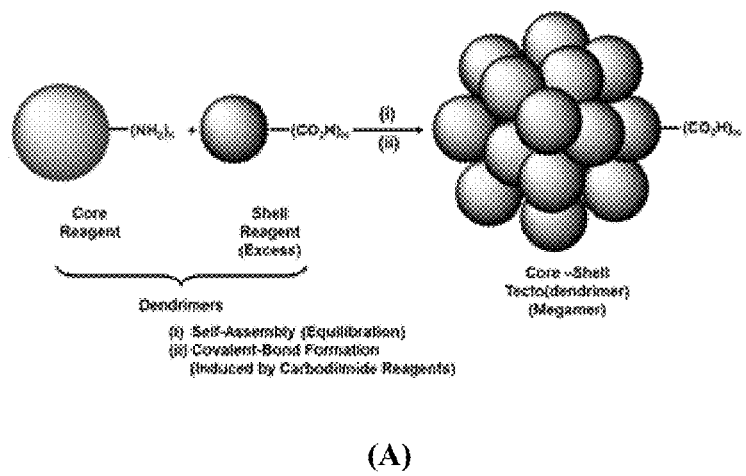
FIG. 9 illustrates the structure of a dendrimer coated with a shell reagent having pyrrolidone moieties.
Figure 9:
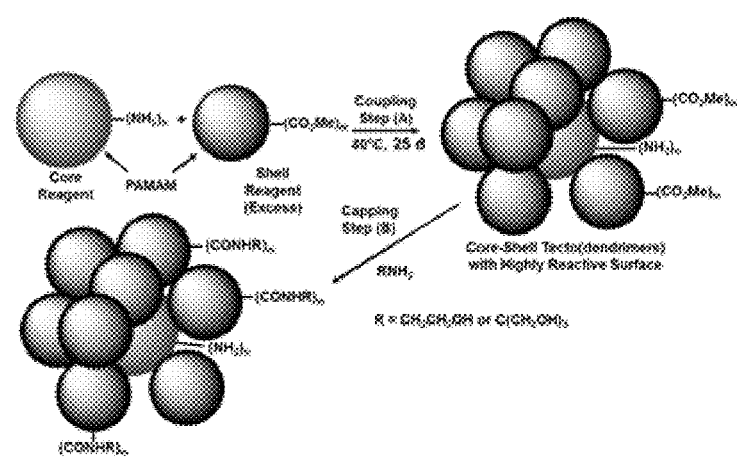

Structurally Organized Megamers: Core-Shell tecto(Dendrimers):

FIG. 9 (A) illustrates a core-shell tecto(dendrimer) as an organized megamer; (B) illustrates a highly reactive megamer surface where a pyrrolidone moiety is present in the shell reagent.

The present invention relates to new unexpected properties observed for certain categories of 4-15-membered amido, urea, urethane and amidoamino heterocycle molecules as well their use in terminated dendritic, functionalized linear or crosslinked polymers that are valuable and useful for a wide range of medical and commercial applications. The molecules are useful as tracers (defined above) having strong non-traditional intrinsic fluorescence.

Non-traditional, intrinsic fluorescent (NTIF) materials have generally been recognized to be polymeric materials containing high multiplicities of tertiary amines. They initially were considered to be derived exclusively from dendrimer structures; however, it is now known that the NTIF phenomenon has been observed in all four major architectural categories.

These NTIF phenomena have never been observed or reported in low molecular weight organic structures such as traditional fluorophores such as those described in traditional fluorophores (Category I above). The present invention concerns classes of small molecule organic materials not possessing any of the attributes or features of traditional fluorescent materials, yet exhibit fluorescence emissions between 300 and 800 nm. One very important distinguishing property is that they generally contain non-aromatic, low molecular weight structures (basic units <500 da) and are characterized by low toxicity, non-immunogenic constituents that appear to be robust against photobleaching. Furthermore, they may be used independently as individual small NTIF structures or integrated into a broad range of organic/inorganic polymeric lattices or nanoparticles to produce useful fluorescence emission properties or high value and importance in diagnostics, whitening agents, sunscreens, forensics, LEDs, drug delivery, biological cell labeling and imaging. An example of such NTIF nanoparticle is the use of these small structure fluorophores as terminal groups on dendrimers. These NTIF fluorophores may be polymerized, conjugated and/or attached by charge neutralization to substrates varying from nanoscale to macroscale. They are building blocks that show valuable emission fluorescence properties that are enhanced by associating high multiples of these fluorophores on substrates with dimensions ranging from nanometric (nanometer) to macroscale (meters). Their fluorescence properties may be enhanced by associating large multiples of these fluorophores by polymerization, conjugation, aggregation, supramolecular assembly, charge neutralization and physically.

When a wide variety of simple, low molecular weight (i.e. <700 Dalton) N-substituted-4-carboalkoxy/carboxylic acid functionalized pyrrolidone compounds (i.e., cyclic amide type heterocyclics), not even attached to dendrimers or other polymer scaffolding were tested, they exhibit significant non-traditional fluorescence (NTF)/intrinsic fluorescence (IF) with emissions in the visible-near infrared region (i.e., 400-850 nm). These emissions appear to be influenced by the presence or absence of certain electron withdrawing/donating groups. For example such groups are: hydroxyl, amino, carboxyl, amido, urea, carbamate (i.e., urethane). These simple pyrrolidone derivatives possess various connector functionalities that allow attachment of these NTF fluorophores to a wide range of inorganic/organic particles or scaffoldings including silica, carbon, metals, synthetic polymers, proteins, DNA/RNA, viruses, and others.

Surprisingly, the absorption/emission properties of these simple pyrrolidone based NTIF fluorophores coincide very closely with very desirable features that are required for commercially significant fluorescent whitening agents (FWAs). In essence, the objective of an FWA is to use a fluorescent compound that absorbs UV light and converts the energy into visible light of higher wave length (i.e., in the blue region). In this way, a yellow appearance of a substrate can be corrected by the emission of a corresponding amount of blue-violet light by the fluorescent compound. The effectiveness of the fluorescent agent depends on the presence of ultraviolet light in the illuminant.

FWAs are used in many large scale commercial applications such as: textile/fabric/dental whiteners, dental composites, personal care, paints, paper coatings, inks, synthetic polymers, coatings, natural polymers (i.e. wool/silk and others), cosmetics, fluorescent tracers for detection of minute leaks (i.e., adhesives/sealants), films, surfaces, fluorescent calibrators for defining nano-porosity in membranes or other substrates or as tracers for drug delivery applications (i.e. siRNA, DNA, oncology, other biomedical roles, etc.). By far, the greatest use of FWAs is in detergents, and almost every commercial detergent contains one or more FWAs, in proportions of 0.05%-0.3% by weight.

These present NTIF-FWAs are expected to exhibit enhanced properties in the areas of: lower cytotoxicity, lower phototoxicity, biodegradability, non-immunogenicity, retention or rejection to substrates, quenching, shelf stability and be cost competitive with many current traditional UV absorbers and fluorophores; yet present a wide range of very tunable chemistry moieties suitable for applications in many life science/medical applications such as for their use in gene transfection and other drug delivery roles (i.e. biocompatible tracers).

PYRROLIDONylation

Based on the extensive and highly positive history for the in vivo use of PVP in over 500,000 human recipients during the past 70 years, there has been a very active interest in remediating the shortcomings of this polymeric composition as a replacement for PEG's. [F. M. Veronese et al., *J. Bioactive Compatible Polym.*, (1995), 10, 103-12], and *Macromolecular Chem. Phys*, (1999), 195, 9-79]. These efforts have been directed mainly at avoiding high MW (i.e., >50 KDa) PVP fractions by using chain transfer polymerization protocols [Torchillin et al., *Biomaterials*, (2001), 22, 3035-3044]. Unfortunately, the products obtained were very poly-dispersed and generally lacked suitable functionality for covalent attachment to the therapeutic drugs. In another more recent effort, Pfister et al., [U.S. Pat. No. 6,080,397 (2000)] attempted to remove high molecular weight fractions by ultra-filtration of commercial PVP, however, without complete success. These failures to remediate these widely recognized deficiencies of commercial PVP were highlighted recently by Login et al., (www.rloginconsulting.com/ . . . pyrrolidone%20backbone%20polymers.pdf) with the suggestion that condensation polymerization strategies be considered for introduction of the highly desirable pyrrolidone ring into the polymer main chain versus the use of free radical polymerization approaches which yield products with the pyrrolidone ring pendant to the main chain.

Synthesis of Mono-Functional Linear/Dendritic PYRROLIDONylation Agents:

Iterative Aza-Michael Addition/Amidation Sequencing Chemistry

The iterative di-aza-Michael addition/cyclization with dimethyl itaconate (DMI) followed by di-amidation with an excess of ethylenediamine (EDA) protocol was first performed on cystamine as described below:

Aza-Michael Addition/Cyclization Step:

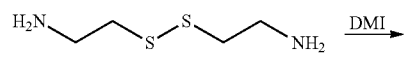

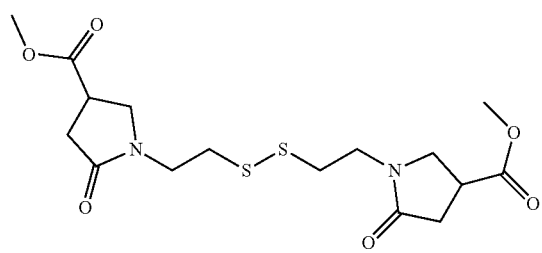

Excess EDA Amidation Step:

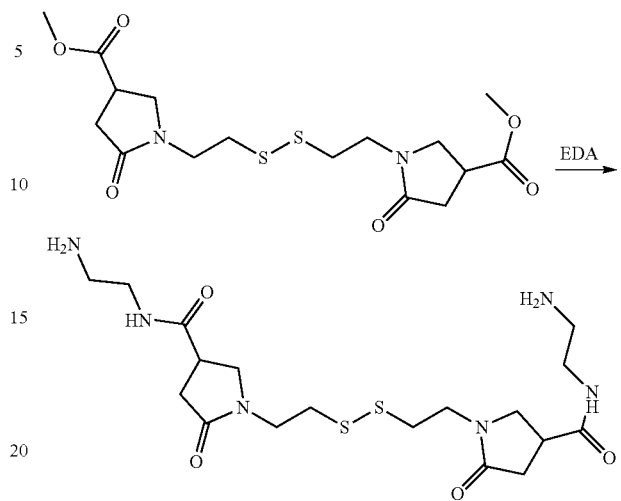

General Procedure:

Aza-Michael Addition/Cyclization: Pyrrolidonylation Step:

To a stirred methanolic solution of DMI (i.e., 20% excess) was added a methanolic solution of amine terminated core or amine terminated pyrrolidone polymer in a dropwise manner. The reaction mixture was allowed to stir at RT overnight. The methanol solvent was removed on a rotary evaporator and then extracted three times (i.e., a liquid-liquid extraction) with 20 mL of toluene and 20 mL of water (per 30 g of theoretical product). Complete removal of excess DMI was confirmed by NMR. Generally, a silica plug flow purification step was performed by mixing 110 g of silica with the product and filtering on to a Buchner funnel. This filter cake was then washed with 100 mL of denature alcohol (per 30 g of theoretical product). Removal of amine containing impurities was confirmed by the absence of a baseline was noted using TLC (i.e., methanol solvent). Additional support for desired structures was confirmed by $^1$H and $^{13}$C-NMR and FTIR (i.e., characteristic enhancements for ester and pyrrolidone amide functionality).

Amidation with Excess EDA Step:

The 4-ester pyrrolidone terminated polymers dissolved in a minimum amount of methanol were added dropwise to a stirred excess (i.e., 5-10 fold excess) of EDA. Progress of the amidation reactions was followed by TLC and FTIR. Since the pyrrolidone ester terminated polymers are very mobile (i.e., methanol) on silica plates the extent of amidation was readily determined by loss of mobile TLC bands which conformed to the concurrent loss of ester carbonyl absorption (i.e., ~1745 cm$^{-1}$) by FTIR. These amidation reactions were performed under several different conditions as described below:

(a) Amidations complete in 2-3 days by stirring at RT.
(b) Amidations complete in 4-6 h at 50° C.
(c) Amidations complete in 5-30 min when run in a microwave apparatus at 10% power.

The excess EDA was removed by azeotropic distillation with toluene (10 mL for 13 g theoretical product) and minimal methanol to make the polymer miscible on a rotary evaporator. Generally 5-10 azeotropic distillations were required to completely remove all EDA. The product quality was monitored by TLC (i.e., elution solvent was NH$_4$OH in methanol); wherein, the products were found to become more mobile on the silica plates as the degree of polymeric pyrrolidonylation increased.

This two-step iterative process strategy was demonstrated for several substrates including: (a) simple amine cores, (b) amine terminated PAMAM dendrimers and (c) amine functionalized silica substrates (i.e., nano/micro particles). Specific examples are as described in the later examples.

Improved Synthesis of Linear-Poly(Amidopyrrolidones); Silica Supported Pyrrolidonylation Cores The interative pyrrolidonylation of functionalized amine cores (i.e., cystamine) using the two-step (a) aza-Michael addition/cyclization, (b) amidation solution chemistry to synthesize linear-poly (amidopyrrolidones) may be readily used to prepare gram quantities of the desired linear-poly (amidopyrrolidones). A rate limiting operation encountered with this solution protocol involves the complete removal of excess EDA in the amidation step. Incomplete removal of EDA leads to formation of trailing degrees of pyrrolidonylation products and less discrete oligomer lengths. Currently, the only effective EDA removal method has been repetitive azeotropic distillation with toluene. In some cases, as many as 6-10 azeotropes are required for complete EDA removal. That withstanding, an improved protocol which allows faster and higher levels of linear-poly (amidopyrrolidones) production by covalently attaching appropriate cleavable (i.e., cystamine) or non-cleavable (i.e., amine functionalized) pyrrolidonylation cores to heterogeneous substrates such as silica nanoparticles, fumed silica or micron sized silica particles was found. This is accomplished by using either non-cleavable silane coupling agents such as: (3-aminopropyl) trimethoxysilane (KH540) or (3-glycidylpropyl)trimethoxysilane (KH560) as described in Wang et al., *High Performance Polymers*, 2018, 30, (1), 24-37.

Using non-cleavable amine coupling agents (i.e., (3-aminopropyl) trimethoxysilane) (KH540) leads to a variety of new pyrrolidonylated silica particles with potential applications as fillers, pyrrolidone complexation agents, excipients, etc. Using the 3-glycidylpropyl (trimethoxysilane) (KH560) coupling agent allows subsequent reaction with cystamine to produce heterogeneous silica functionalized pyrrolidonylation cores with cleavable disulfide linkages as shown below:

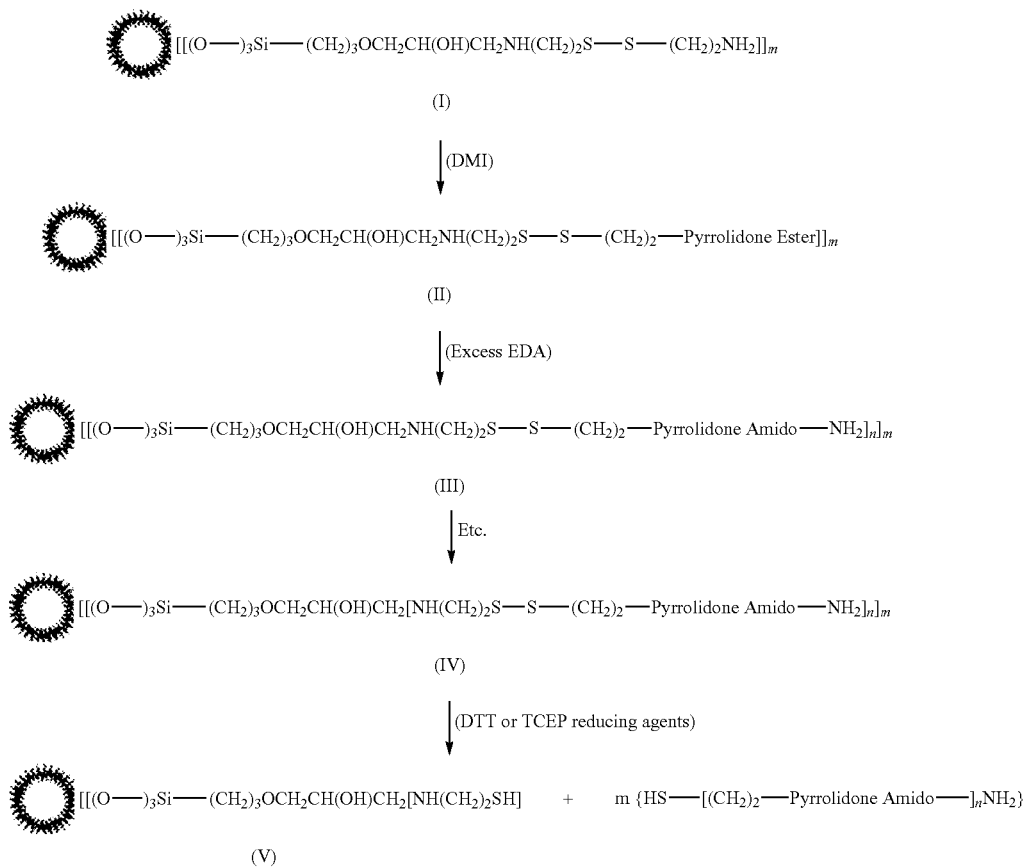

Finally the glycidyl functionalized silica particles with (m) arms are reacted with an excess of cystamine as described in Reaction (I). Following that modification, the two-step iteration of Reaction (II) (a) aza-Michael/cyclization with DMI to give ester functionalized pyrrolidone followed by Reaction (III) (b) amidation with excess EDA produces the silica particle with pyrrolidone amido amine terminated arms (m) as shown in Reaction (IV). These heterogeneous silica substrates allow rapid purification of immobilized pyrrolidonylation products, as well as facile removal of incidental itaconate esters or diamines (i.e., EDA or α,ω-alkylene diamines) by simply washing with appropriate solvents. The robust nature of this protocol also allows acceleration of the amidation step by using microwave assisted techniques. In the case of the cystamine core, after attaining a desired length (i.e., degree of pyrrolidonylation=n), the mono-thiol functionalized, linear-poly (amidopyrrolidone) product may be cleaved by disulfide reduction (i.e., dithiothreitol (DTT) or tris-(carboxy ethyl) phosphine (TCEP)) (Burin, et al, *J. Org. Chem.*, 1991, 56, 2648-2650) and recovered by washing with an appropriate solvent to give the very important orthogonally reactive amino terminated thiol; $NH_2$-[pyrrolidone amido]$_n$-SH or ester terminated thiol; ester-[pyrrolidone amido]$_n$-SH with a discrete linear length defined by n, as shown in Reaction (V).

This two-step, iterative silica particle protocol (i.e., Reactions (I)-(V)) may also be used as a very facile procedure for producing thiol-focal point functionalized (pyrrolidone amido) dendrons possessing amine or ester surface groups. It is practiced by using tris-(2-aminoethyl) amine (i.e., TREN) versus EDA. After performing the two-step iteration sequence to reach a desired dendron generation level, the mono-thiol focal point functionalized pyrrolidonylated dendron is obtained by reduction of the silica supported pyrrolidonylation assemblies with dithiothreitol (i.e., DTT) or tris-(carboxyethyl) phosphine (TCEP). Furthermore, higher boiling point a,ω-diaminoalkanes (i.e., hexamethylene diamines, etc.) may be used as alternates to ethylene diamine since they may be readily washed from the silica supported components.

Other modifications have included the conversion of amine terminated [pyrrolidone amido] functionalized silica particles; Reaction (IV) with maleic anhydride to produce maleimide terminated [pyrrolidone amido] functionalized silica particles (US 2008/0262191 A1, Oct. 23, 2008). These maleimide terminated, [pyrrolidone amido]$_n$-functionalized silica particles may then be reacted with furan to form maleimide-furan Diels-Alder adduct protected termini (Nawroth et al, *Macromol. Biosci.*, 2016, 16, (13), 323-333). Reduction of these silica particles with dithiothreitol (DTT) or tris-(carboxyethyl) phosphine (TCEP)releases these protected maleimide terminated oligomeric arms to yield mono-reactive thiol terminated-[pyrrolidone amido]-maleimide Diels-Alder protected reagents suitable for various selective conjugations to drugs, proteins and other clinically relevant substrates.

Living Cationic Polymerization of Pyrrolidonyl-2-oxazoline Monomers to Linear-Poly(Pyrrolidonyl Oxazolines)

Since the first living cationic polymerization of 2-alkyl-2 oxazoline monomers reported by Tomalia et al. in 1966 (Tomalia et al., *J. Polym. Sci. A*, 1966, 4, (9), 2253-2265) giving mono-dispersed, linear-poly(oxazolines) (POxs) with controlled molecular weights, considerable activity has been noted in this field (Sedlacek et al., *Macromol. Rapid Commun.*, 2012, 33, 1648-1662; Viegas et al., *Bioconjugate Chem.*, 2011, 22, 5976-986). More recently, specific attention has turned to the use of these linear-2-alkyl-poly(oxazolines) (POxs) as replacements for analogous poly(alkylene glycol) (PEG) polymers in stealth-type, drug delivery applications (Bludau et al., *Eur. Polym. J.*, 2017, 88, 679-688).

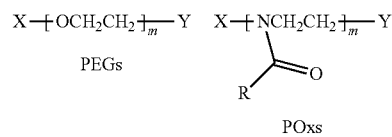

The linear-2-alkyl-poly(oxazolines) have proven to be attractive as alternates/replacements for PEGylated polymers based on: (a) their ability to be polymerized to desired, lower molecular weight PEG analogues (i.e., up to 30 KDa) by means of controlled "living cationic polymerization" mechanisms, (b) linear-2-alkyl-poly(oxazolines) (POx's) have exhibited excellent stealth properties comparable to PEG polymers (Tavano et al., *ACS Nano*, 2018, 12, 5834-5847) and (c) the resulting linear-2-alkyl-poly(oxazolines) have been shown to exhibit superior resistance to oxidation by exposure to air compared to PEG-type polymers. This latter property is believed to be largely responsible for producing oxidation degradation products that cause a variety of immune responses when used in the clinic.

As such, many 2-alkyl-2-oxazoline monomer based polymers (POxs) have been examined recently for use as PEG replacements for enhanced drug delivery applications in the clinic (Knop et al., *Angew. Chem. Int. Ed.*, 2010, 49, 6288-6308; Bauer et al., *Macromol. Biosci.* 2012, 12, 986-998; Harris et al., U.S. Pat. No. 8,088,884 (Jan. 3, 2012) and U.S. Pat. No. 7,943,141 (May 12, 2011)).

Very surprisingly, only a single example describing the synthesis and polymerization of pyrrolidone functionalized-2-oxazoline monomers has been reported by Dandreaux, et al., U.S. Pat. No. 5,008,367, Apr. 16, 1991. That withstanding, there are currently no known examples of their use or proposed application as PEG replacements. The synthesis and polymerization of these pyrrolidonyl oxazoline monomers is readily practiced as described below:

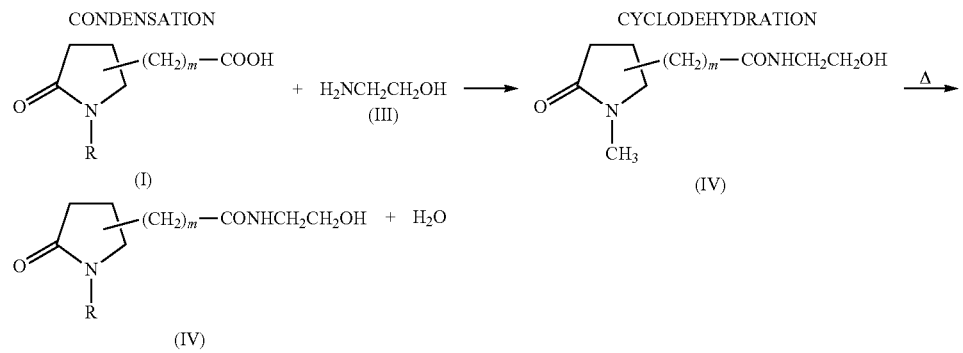

-continued

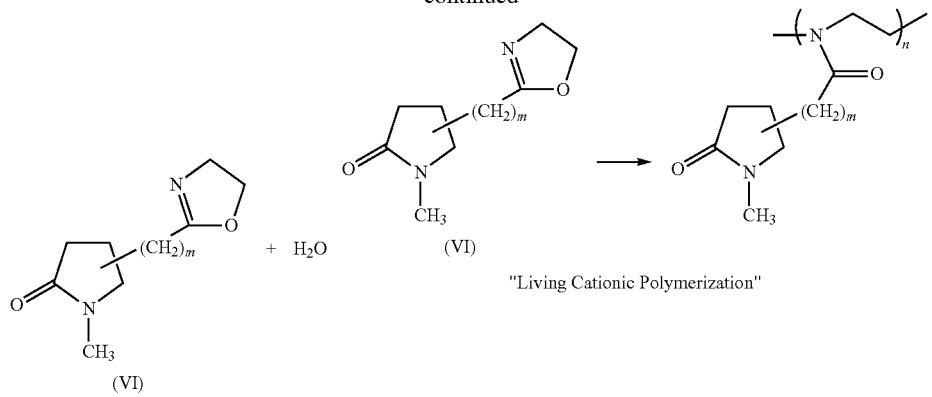

(VI)

"Living Cationic Polymerization"

It is the purpose of this invention to describe/demonstrate the use of pyrrolidonyl-2-oxazoline polymers as monodispersed, controlled molecular weight, stealthy analogues of linear-poly(pyrrolidone) examples above. These unique pyrrolidonyl-2-oxazoline polymers may be readily synthesized within the preferred molecular weight and nanoscale size (i.e., 1-30 KD range), thus assuring excretion by the kidney and use as PEG replacements for drug delivery applications. Furthermore, initiator and terminal functional groups suitable for selective attachment to specific drugs, proteins or other relevant clinical substrates may be introduced into these linear-poly (pyrrolidonyl oxazolines). This allows them to be used as discrete mono-functionalized PEG conjugation analogs. Introduction of suitable reactive moieties either at the initiator or terminal positions on the linear-poly(pyrrolidonyl oxazolines) chain will also allow discrete attachments to functionalized linear-poly(amidopyrrolidones) described above. More specifically, these mono-functionalized, linear-poly (pyrrolidonyl oxazolines may be directly conjugated to functionalized drugs (i.e., Doxorubicin), proteins (i.e., insulin) or other clinically relevant substrates. Alternatively, these stealth-like, mono functionalized, pyrrolidone functionalized poly(oxazolines) may be used as reactive intermediates suitable for modifying and hybridizing many of the dendritic, dendrimer and linear-poly(pyrrolidones) described throughout this invention to produce discrete and unprecedented pyrrolidonyl copolymeric structures suitable for use as PEG replacements.

Using a modification of the method illustrated above for the cationic polymerization of 2-ethyl-2-oxazoline, the corresponding 2-(allyl pyrrolidone functionalized)-2-oxazoline was polymerized to give poly (2-(allyl pyrrolidone functionalized)-2-oxazoline) (where: X=methyl, propargyl; Y=azido, mono-protected piperazine). Using either traditional thermal conditions or microwave assisted conditions, one readily obtains monodispersed poly (2-(allyl pyrrolidone functionalized)-2-oxazoline) as shown below with acceptable molecular weights to assure renal excretion through the kidney. For example, in one instance a poly(2-(pyrrolidonyl functionalized)-2-oxazoline) (i.e., R=1-Me-pyrrolidone, X=Me and Y=—OH) was found to have a relative viscosity in water of 1.63 (1% solution, 25° C.). The absolute molecular was 12,100 by vapor phase osmometry and it had a Tg of 150° C.

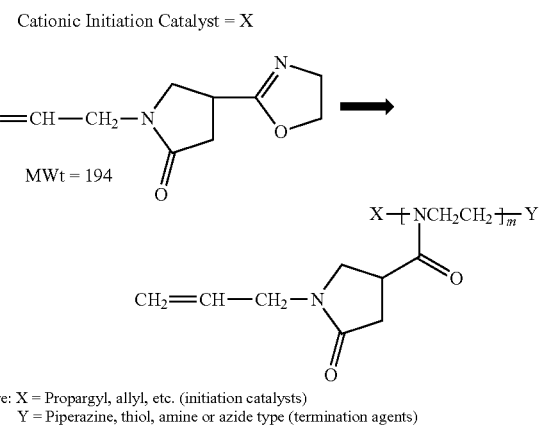

Where: X = Propargyl, allyl, etc. (initiation catalysts)
Y = Piperazine, thiol, amine or azide type (termination agents)
m = 1-150

These various cationically polymerized poly(pyrrolidonyl oxazolines) possessing reactive oxazolinium terminal groups may be allowed to react with reactive (i.e., thiol, piperazine, amine) terminated poly(amido pyrrolidone) intermediates described above. This provides a wide range of suitable poly(oxazoline)-poly(amido pyrrolidone) copolymers for conjugating to various drugs, proteins and clinically relevant substrates as described extensively by G. T. Hermanson Chapter 18 (pp 562-581) in *Bioconjugate Techniques*, 2nd edition, Academic Press, 2008). See especially pp 739-742 for various PEGylation protocols relevant to this invention.

For example, mono thiol-[poly(pyrrolidone amido]$_n$ amine/ester intermediates may be used to terminate living cationic poly(oxazoline)$_m$ groups to produce copolymers with components as described below. For example this would lead to "click reactive" (x) poly(oxazoline)$_m$-(y) poly(amido pyrrolidone)$_n$ type A-B copolymers; where: x=a click reactive propargyl moiety with m=discrete number of poly(oxazoline) units (A) attached to y=discrete number of poly(pyrrolidone amido) units (B) with n=degree of pyrrolidonylation.

(A)

-continued

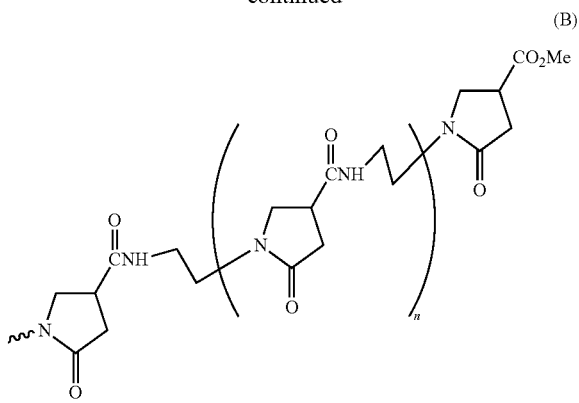

(B)

Note that Formula (A)=Formula (V); Formula (B)=Formula (VI).

Figure 3A:
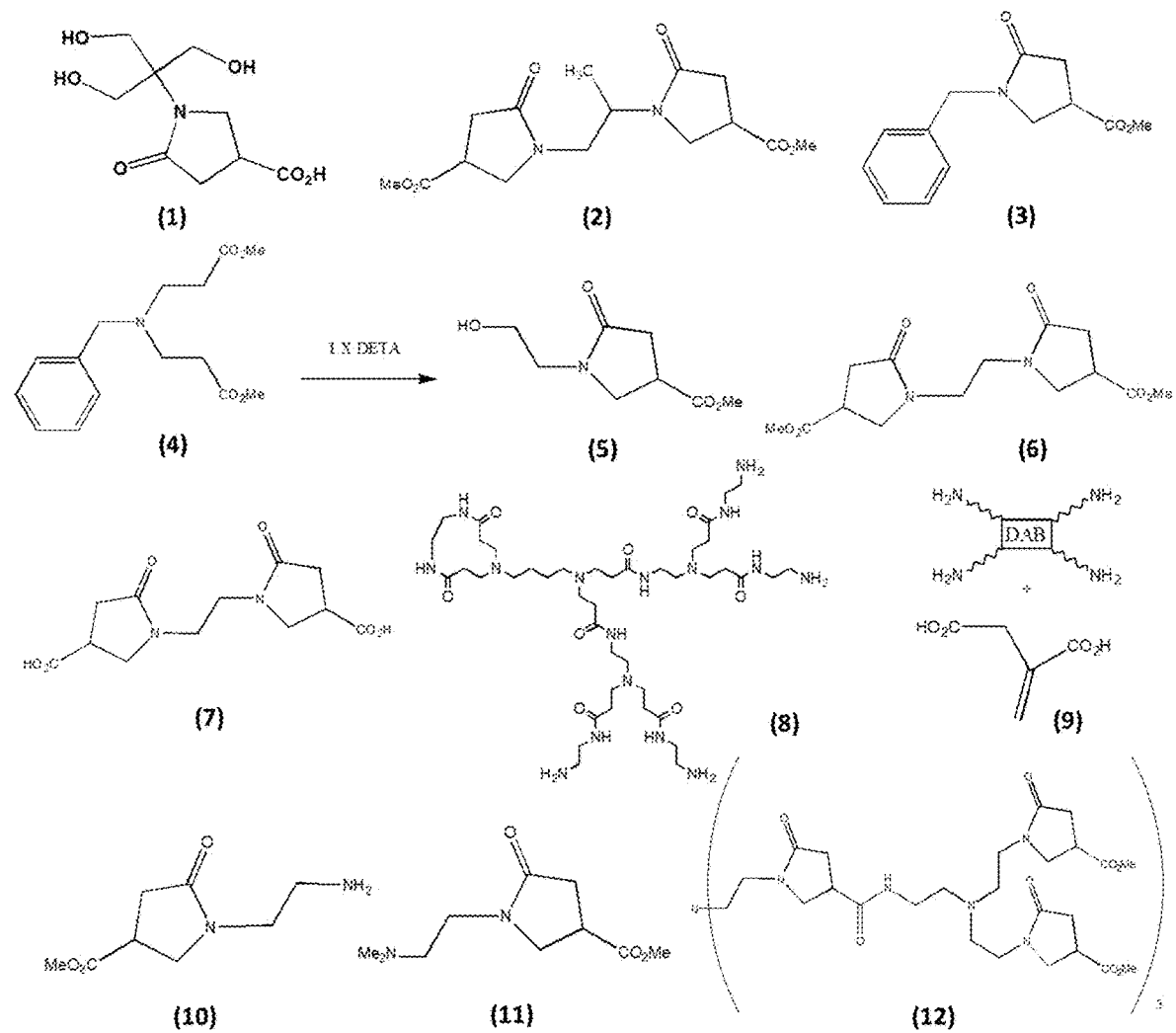
FIGS. 3A-3D show the chemical structure of the compounds of the Examples numbered in Table 2.
Figure 3:
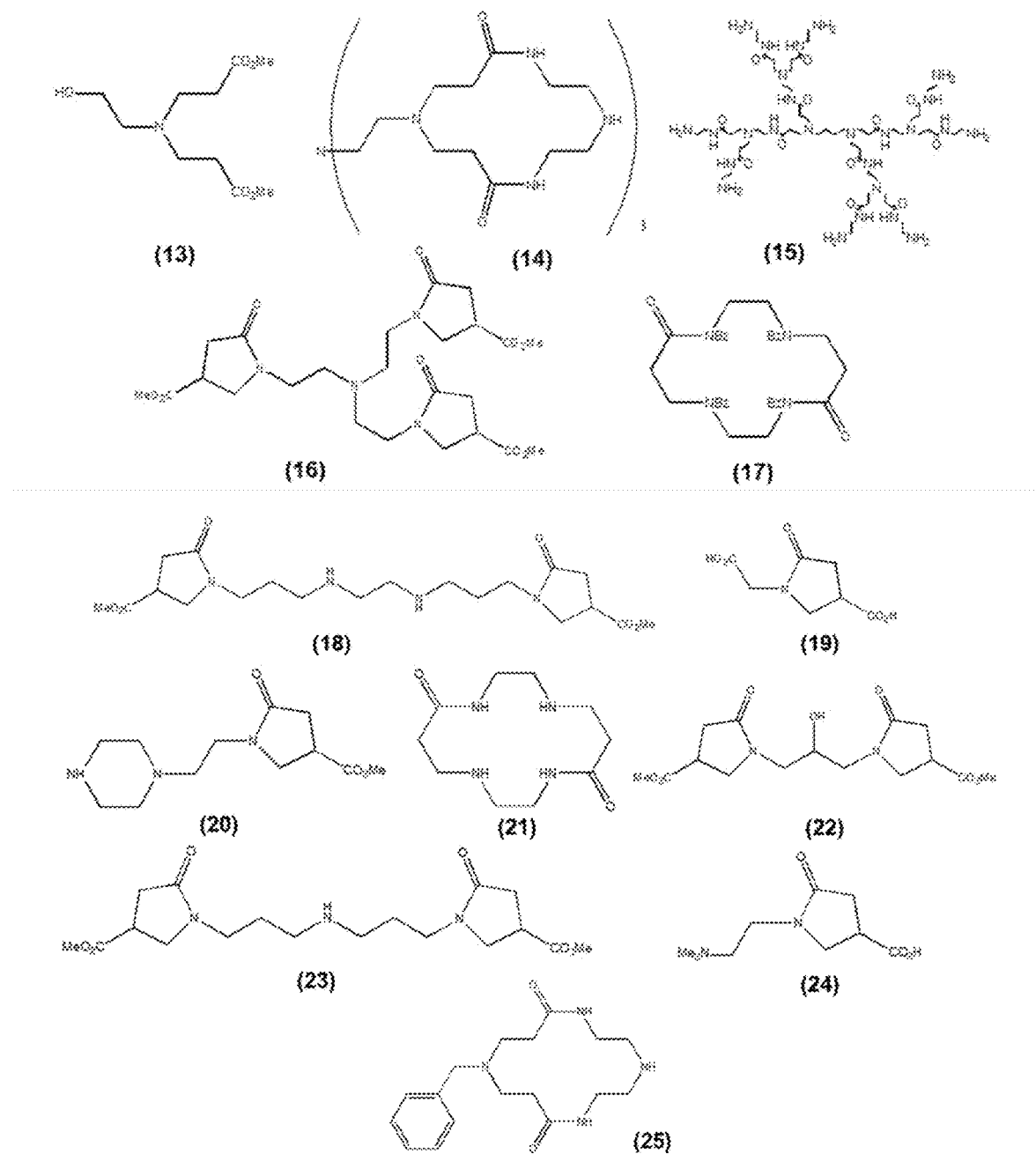
Figure 3:
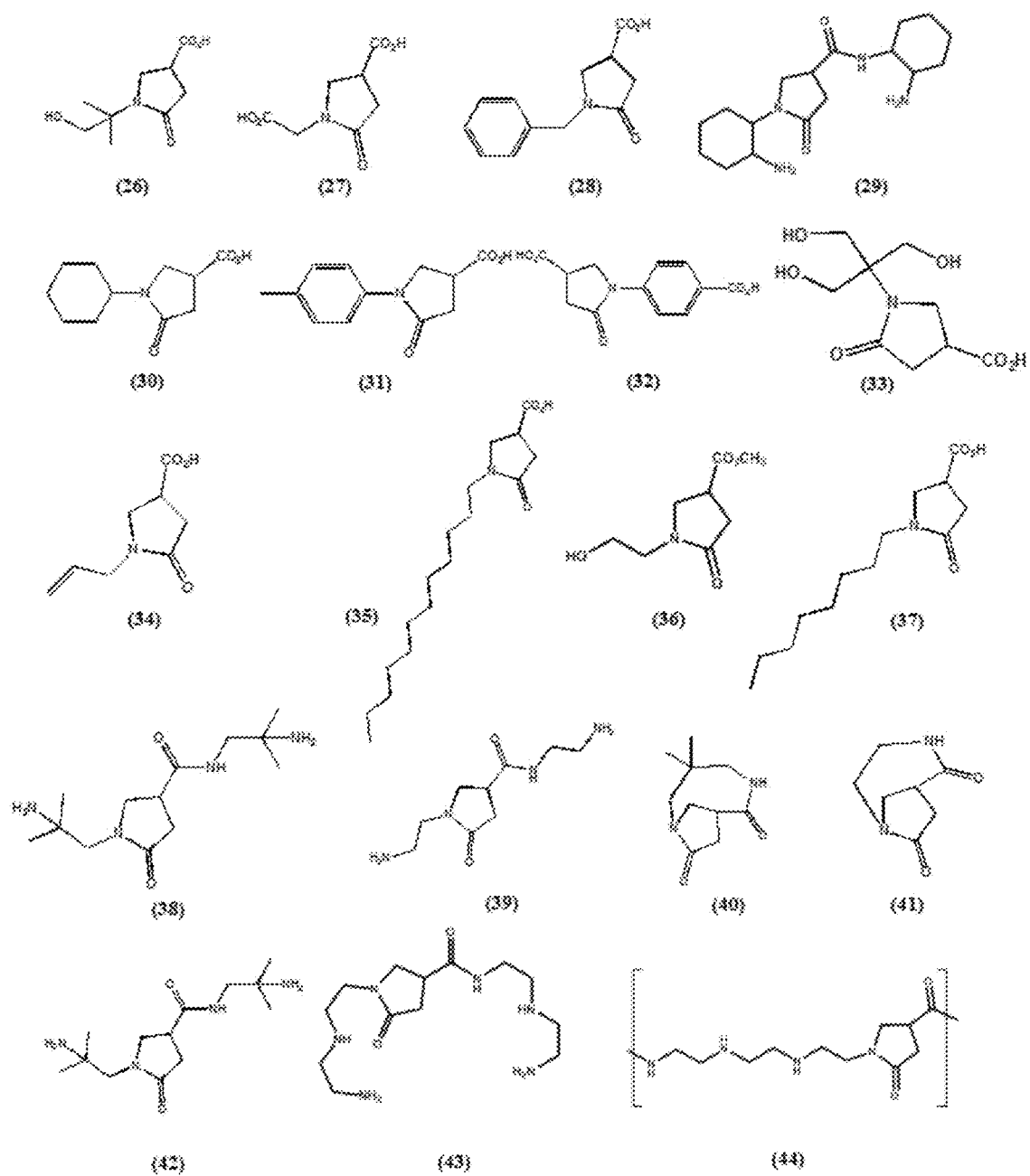

General Procedure for the Synthesis of N-Substituted-4-Carboxy-Alkylate/Arylate Pyrrolidones The appropriate alkyl or aryl amine (0.05 moles) was weighed into a 100 mL round-bottom flask equipped with a magnetic stirrer and containing 15 mL of dry methanol. While stirring, the appropriate dialkyl/diaryl itaconate (0.05 moles/primary amine moiety) dissolved in 15 mL of dry methanol was added dropwise over a period of 10 min. In some cases, a moderate exotherm was noted. The reaction was allowed to stir at RT for 1 h followed by refluxing for 8-10 h. The final product was obtained by removal of the solvent with a Buchi roto-evaporator to give a solid, liquid or syrup with yields ranging from 75-98%. See Table 2 in the Examples and FIGS. 3A-3B for their structures. These final products were characterized by FTIR, $^1$H—, $^{13}$C-NMR. Their UV-vis/fluorescence properties were evaluated with a fluorospectrometer (Spectramax from Molecular Devices) yielding data as described in Table 2 in the Examples.

General Procedure for the Synthesis of N-Substituted-4-Carboxylic Acid Pyrrolidones Itaconic acid (Sigma-Aldrich) (0.05 moles/primary amine moiety) was weighed into a 100 mL round-bottom flask equipped with a magnetic stirrer. While stirring, the appropriate alkyl or aryl amine (0.05 moles) was added dropwise over a period of 10 min. In some cases, a moderate exotherm was noted with a transformation into a liquid melt, while in other cases each reactant remained as a solid and was intimately mixed. The flask and reaction mixture was surmounted by a reflux condenser and immersed in an oil bath and heated at 125° C. for 2-5 h. The formation of water condensate from the reaction can be noticed in the condenser. A 25 mL portion of dry methanol is then added and the reaction mixture is refluxed for 1 h. Removal of solvent on a Buchi roto-evaporator produces the desired pyrrolidone product as an oil, syrup or solid in yields ranging from 59-95%. These final products were characterized by using a Thomas-Hoover capillary melting point apparatus, FTIR and $^1$H—, $^{13}$C-NMR. Their UV-vis/fluorescence properties were evaluated with a fluorescence spectrometer (Spectramax from Molecular Devices) yielding data as described in Table 2.

Functionalized Dendritic Polymers

The first report that carboxylate-terminated PAMAM dendrimers possess weak, but detectable, fluorescence appeared in 2001 (Larson and Tucker, *Applied Spectroscopy*, 2001, 55, 679-683). A broad peak with an excitation and emission maximum of 380 and 440 nm, respectively, was observed. Even though the exact nature of the fluorescence was not fully understood, the authors claimed that is was most likely due to an n→π* transition from amido groups throughout the dendritic structure. Much stronger fluorescence emission from G2 and G4 amino-terminated PAMAM dendrimers was observed later for very similar excitation and emission wavelengths (Wang and Imae, *J. Am. Chem. Soc.* 2004, 126, 13204-13205). Both G2 and G4 PAMAM dendrimers showed a significant pH-dependent fluorescence property. The emission was detectable in acidic conditions for pH lower than 5. Linear relation between fluorescence intensity and dendrimer concentration was observed. Unsuitable low pH value required to observe dendrimer intrinsic blue fluorescence substantially limits its applicability in biological systems.

Later, it has been found that the emission intensity can be dramatically enhanced upon oxidative treatment (Wang et al., *J Colloid Interface Science*, 2007, 306, 222-227) probably due to oxidation of tertiary amines. Therefore, G4 PAMAM dendrimer was treated with ammonium persulfate to enhance its intrinsic fluorescence. Such prepared dendrimers were used as carriers of three antisense oligonucleotides enabling gene delivery and bioimaging at the same time (Tsai et al., *Biomacromolecules*, 2011, 12, 4283-4290).

More recent confirmation of the low cytotoxicity and minimal interaction of the poly (pyrrolidone) moiety with proteins, as presented on the surface of poly(amidoamine) (PAMAM) dendrimers is reported by Klajnert et al. (*Nanomedicine, NBM,* 2012, 8, 815-817; *Nanomedicine, NBM,* 2013, 9, 461-464). Currently, PVP is being used as an adjuvant for immobilizing spermatozoa for in vitro fertilization protocols (www.coopersurgical.com).

Figure 2:
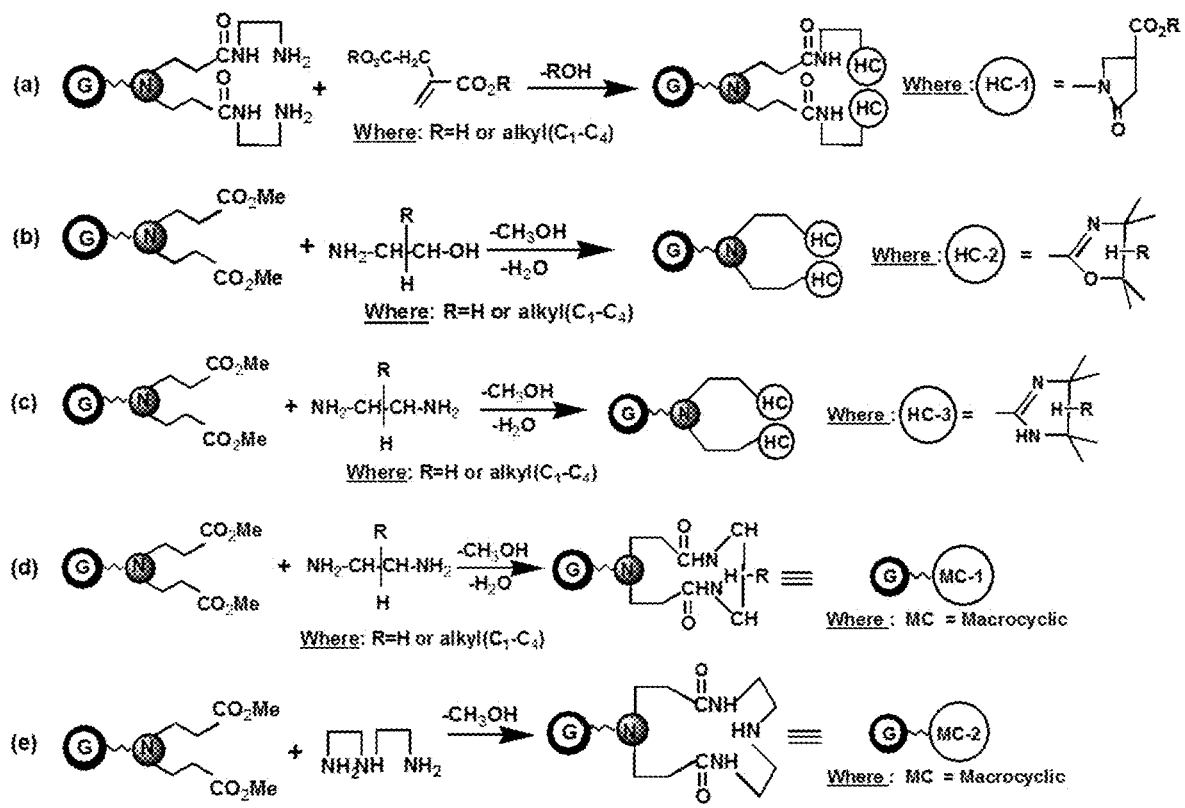
FIG. 2 shows the schematic process for preparing terminated heterocyclic dendrimers.

The present invention modifies the surface of PAMAM dendrimers (G=0–6) by converting its standard surface chemistries (i.e., ester, amino, hydroxylic, carboxylic) into various heterocyclic or macrocyclic moieties containing; amino, amido, imino, ether, ester, keto, carboxylic or thioether functionalities, but not limited to this list, which has led to dramatic enhancements in the "intrinsic fluorescence" (IF) observed for the functionalized dendrimer. For example, conversion of dendrimer amine terminal groups into 4-carbomethoxy pyrrolidones as illustrated in FIG. 2 (a) enhanced the intrinsic fluorescence by >18× compared to the amine terminated dendrimer precursor. This dramatically enhanced IF makes it possible to image/label biological cells; whereas, non-heterocylic functionalized dendrimers exhibit very low fluorescence emission intensities that are too weak to use for cell imaging/labeling. Similar results were observed for other heterocylic and macrocyclic moieties as described in FIG. 2 (b), (c), (d) and (e).

More specifically, the present invention relates to new, non-traditional fluorescence (NTF), stealth (i.e., non-immunogenic) and enhanced temperature stabilization properties observed for functionalized 2-pyrrolidone, 2-piperidone, 2-aza-cycloheptanone or 2-azetidinone-terminated dendritic polymers. The preferred examples of 4-carboxalkoxy, 4-carboxamido or 4-carboxylic acid derivatives of pyrrolidone are obtained by reacting a precursor primary amine, (e.g., —$NH_2$)-terminated dendritic polymers with certain functionalized methacrylate ester, methacrylic acid or methacrylamide reagents to produce new and novel dendritic, linear, branched or crosslinked polymers either terminated or functionalized or both with ester, carboxylic acid or amido substituted 2-pyrrolidone moieties. These pyrrolidone terminated dendrimers are made by the process described in WO2004/069878, published 19 August.

Evaluation of Complement Activation Properties for PYRROLIDONylation Agents:

General Complement Activation Evaluation (CAE) Protocol

General procedures and protocols for evaluating complement activation (i.e., immune responses) for various structures and nanoparticles are described extensively in Peakman et al., *J. Clin. Pathol.* 1989, 42, 1018-1025, Wen et al., *J. Allergy & Clincal Immunology,* 2004, 113(4), 585-593, and more recently Tavano et al. *ACS Nano,* 2018, 12, 5834-5847. Thus these procedures have been known for many years and are used currently as well.

More specific protocols used for evaluating complement activation parameters for pyrrolidonylated poly(amidoamine) (PAMAM) dendrimers, such as described in this invention, have been reported in a recent patent application (WO 2017/191219 A1, 9 Nov. 2017) and are described below:

Determination of Complement Activation for Pyrrolidonylated Poly(amidoamine) (PAMAM) Dendrimers To measure complement activation in vitro, the human serum complement products can be measured by Peakman et al., *J. Clin. Pathol.* 1989, 42, 1018-1025. More recently it has been measured according to Tavano et al. *ACS Nano,* 2018, 12, 5834-5847 and described in WO 2017/191219.

Other analogous and suitable small to large (4-15 membered) heterocyclic moieties, such as 2-azetidinone, 2-piperidone, 2-aza-cycloheptanone or macrocyclic amidoamine moieties, may be introduced directly at the surface termini of dendritic or crosslinked polymers or via suitable functionality presented by linear or branched polymers using a variety of synthetic methods described in the literature. These heterocyclic functionalities are referred to herein collectively as "idones".

This invention further embodies the reaction of these "idone-terminated/functionalized" polymers with ester, acid or amine reactive reagents to provide new and novel "mixed functionality" dendritic polymeric materials that exhibit and express these new NTF, stealth or enhanced temperature stability properties.

This invention, based on unpublished work at NanoSynthons LLC/The National Dendrimer & Nanotechnology Center as described herein, demonstrates the following unprecedented results:

A high yield (i.e., 93-98% yield), facile synthetic process (i.e., 1-step) for the conversion of Miaminobutane-Corel; amine terminated PAMAM dendrimers (i.e., G=0–6) to 4-carbomethoxy pyrrolidone terminated PAMAM dendrimers (4-CP-PAMAM's) (i.e., G=0–6) has been made and successfully scaled up to multigram quantities.

A high yield (i.e., 90-98% yield), facile synthetic process (i.e., 1-step) for the conversion of [Cystamine-Core]; amine terminated PAMAM dendrimers (i.e., G=0–6) to 4-carbomethoxy pyrrolidone terminated PAMAM dendrimers (4-CP-PAMAM's) (i.e., G=0–6) has been defined and successfully scaled up to multigram quantities.

4-Carbomethoxy pyrrolidone terminated PAMAM dendrimers (i.e., G=4.0) have been shown to exhibit >18× greater NTF emission intensity compared to the corresponding amine terminated PAMAM dendrimer (i.e., G=4.0) without the need for oxidizing agents or lower pH adjustments. See Table 2 in the Examples.

Figure 6:
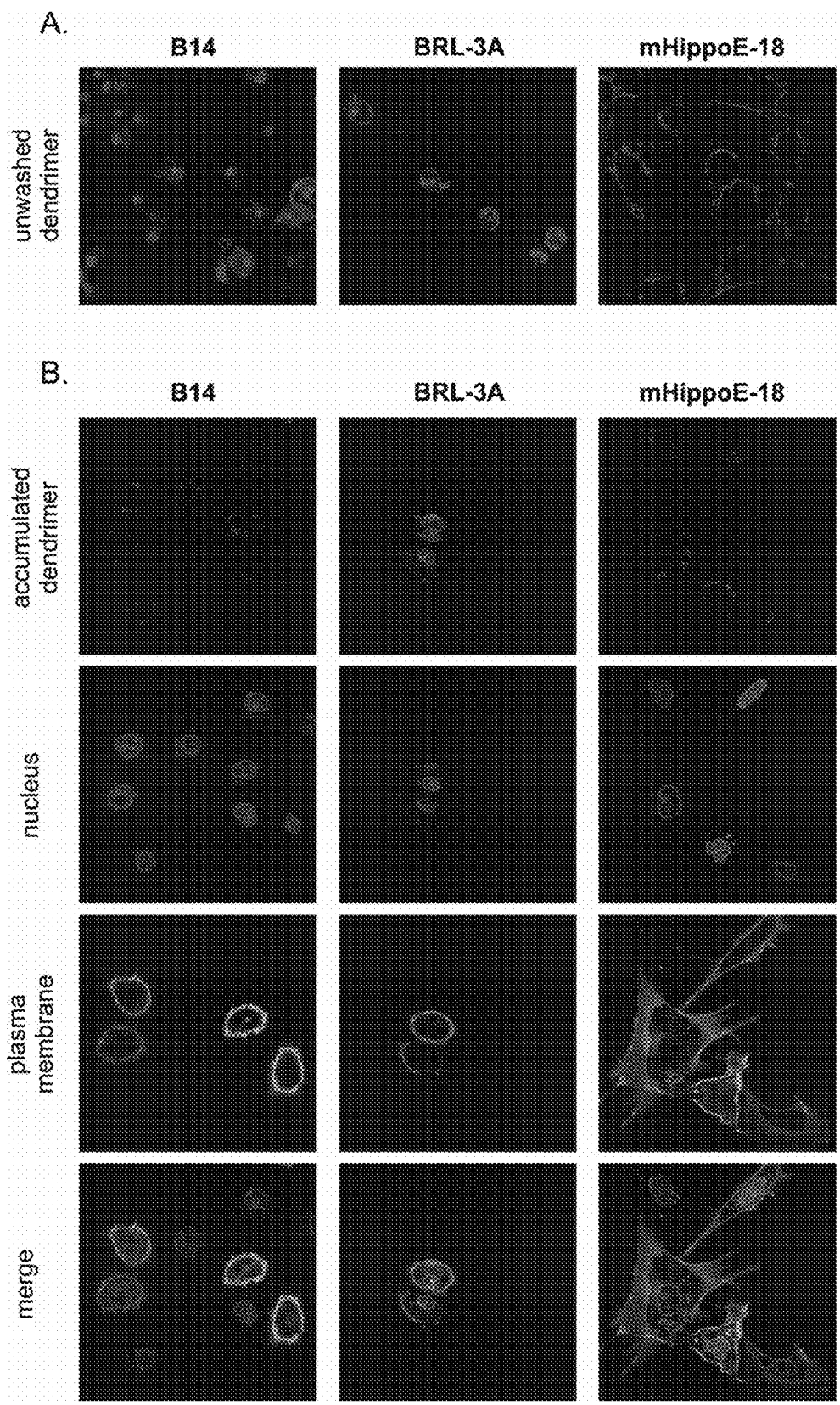
FIG. 6 shows the confocal images of B14, BRL-3A and mHippoE-18 cells treated with 100 μM of PAMAM-pyrrolidone dendrimer for 24 h. (A) Intrinsic dendrimer fluorescence of unwashed and non-fixed cells. (B) Following dendrimer accumulation (blue channel), cells were rinsed once with PBS and stained to visualize cell nucleus (red channel) and plasma membrane (green channel). Before imaging, cells were fixed with formaldehyde.

4-CP-PAMAM dendrimer (i.e., G=4.0) has been demonstrated to enter biological cells by some, as yet to be defined, endocytosis mechanism and exhibited sufficient NTF emission intensity to allow successful imaging of cytoplasmic domains in three different cell lines. (Univ. of Lodz). See Example I and FIG. 6.

4-CP-PAMAM dendrimers (i.e., G=0–4) have been shown to exhibit very low cytotoxicity and virtually no "complement activation" features. See Example I.

Over 30 simple, but different 4-carbomethoxy/carboxylic acid pyrrolidone derivatives have been synthesized, characterized and shown to exhibit significant NTF emission properties having emission maxima ranging from the visible to the near infrared region (i.e., 400-750 nm). See Table 2 in the Examples. While not wishing to be bound by theory, it is believed that these emission maxima appear to be readily designed and controlled by a combination of selecting suitable excitation wavelengths and appropriate pyrrolidone structure design.

This NTF phenomena has never been reported for such simple, low molecular weight pyrrolidone structures or functionalized dendrimers. It has the emission intensity needed for many uses that before were not attainable in a non-toxic system.

These simple, 4-carbomethoxy/carboxylic acid pyrrolidone derivatives, possess suitable chemical functionality to allow them to be conjugated to a wide range of dendrimers and other polymer architectures for NTF and other cell labeling evaluations.

A method of tracing moieties and fluids in various systems, tests, plants or animals and humans by fluorescence, and monitoring or detecting the location of the moiety by fluorescence using a compound of Formula (I) or Formula (II).

Modification of dendrimer surface groups is a commonly applied method to reduce toxicity of dendrimers. Such modification was proposed by Tomalia et al. who developed a polyamidoamine (PAMAM) dendrimer with 4-carbomethoxypyrrolidone surface groups (WO 2004/069878, 19 Aug. 2004). Biocompatibility of this dendrimer has been assessed (Ciolkowski et al., *Nanomedicine NBM,* 2012, 8, 815-817; Janaszewska et al., *Nanomedicine NBM,* 2013, 9, 461-464). After analyzing the ability of the dendrimer to interact with human serum albumin, its hemolytic activity and toxic effect on mouse neuroblastoma cell line N2a, it was possible to draw a conclusion that PAMAM dendrimer having carbomethoxypyrrolidone surface groups reveals superior properties in comparison with unmodified PAMAM dendrimers with amine surface groups (Ciolkowski et al., *NBM,* 2012, 8, 815-817).

Further studies on biocompatibility of the modified dendrimer have confirmed their potential towards applicability in nanomedicine. Using three rodent cell lines: Chinese hamster fibroblasts (B14), embryonic mouse hippocampal cells (mHippoE-18) and rat liver derived cells (BRL-3A), it has been shown that the modified dendrimer has not induced cell apoptosis, has not caused reactive oxygen species (ROS) generation and has not changed mitochondrial membrane potential (Janaszewska et al., *Nanomedicine NBM,* 2013, 9, 461-464). Generally, for all three cell lines, the dendrimer has been non-toxic. Such a result gives rise to a question whether the dendrimer enters cells. To address the question, the uptake of the modified PAMAM-pyrrolidone dendrimer for the same three rodent cell lines was done. Monitoring whether the dendrimer enters a cell was possible thanks to a unique property of pyrrolidone-modified PAMAM dendrimers: they possess strong intrinsic fluorescence ($\lambda_{exc}$=370 nm, $\lambda_{max\ em}$=440 nm).

The invention will be further clarified by a consideration of the following examples, which are intended to be purely exemplary of the invention.

Materials and Methods Used in the Examples

Materials

All chemical reagents were purchased from commercial suppliers.

Solvents for the synthesis of the dendrimer were purchased from Sigma-Aldrich.

All cell culture reagents were purchased from Gibco® (Germany).

Flasks and multiwell plates for in vitro studies were obtained from Nunc (Germany) SensoPlate™ 96-well glass-bottom plates for confocal microscopy were from Greiner Bio-One (USA).

PBS and FBS were purchased from Sigma-Aldrich.

Trypan blue was purchased from Molecular Probes (USA).

NeuroDio and RedDotl were purchased from Biotium (USA).

Chinese hamster fibroblasts (B14; ATCC no CCL-14) cell line was purchased from ATCC (USA). Embryonic mouse hippocampal cell line (mHippoE-18) was purchased in CEDARLANE Laboratories Limited (Canada). Rat liver-derived cell line (BRL-3A) was purchased from Banca Biologica e Cell Factory (Italy).

Fluorescence data was acquired with a Perkin-Elmer LS50B Luminescence spectrometer. Constant slit widths (Both excitation and emission—3 nm) were used and the concentrations were adjusted to give on scale emission responses. Emission responses were divided by concentration to give response per gram and multiplied by a scaling factor chosen to set the relative response of the standard, fluorescein-Na, to 1,000,000.

Fourier Transform Infared Spectroscopy (FTIR) 1600 from Perkin Elmer

Anasazi 60 MHz NMR

All the products can also be purified using Sephadex LH-20 in methanol. The columns used here have about 400 g dry Sephadex LH-20. The void volume used for the dendrimer samples is 300 mL. Fractions are taken in test tubes of ~18 mL each (20 mL tubes). Under these conditions G=0 comes out initially at ~ fraction 6 or 7 and G=5 at fraction 2 or 3. Fractions are monitored using a silica gel TLC plate. Two lines are drawn on the plate with each line marked with 0.5 cm separation and each fraction is spotted on every other mark. The plate is simply placed in an iodine chamber. Fractions containing product are collected and stripped on a rotary evaporator.

General Synthesis Scheme

The synthesis of pyrrolidone terminated PAMAM dendrimers were made by the method of Tomalia et al. (WO2004/069878, published 19 Aug. 2004). In a similar matter described by WO2004/069878, all dendritic polymers such as dendrons, dendrimers, dendrigrafts, core-shell tecto(dendrimers), hyperbranched polymers with terminal primary amines can be reacted in this manner, including Examples 1-25. In the following Table 2 and Example I, these compounds were made by this method. General Processes and specific examples are numbered. Comparative Examples are lettered. Example I shows the process to make, by the similar method, the compound tested in the utility discussed.

Example 1: General Preparation of N-alkyl-4-carbomethoxypyrrolidones from Primary Amines Mono 1° amines (i.e., —NH$_2$) containing a variety of functionalities that exhibit orthogonal reactivity to carboxylic acids may be converted to the corresponding 4-carboxylic acid pyrrolidones in high yield. These products were obtained by heating various stoichiometric quantities of the 1° amine and carboxylic acid in the presence of toluene at ~125° C. using a Dean-Stark apparatus. After removal of predicted stoichiometric amounts of water (~2-3 hrs.), the products are obtained as hygroscopic, powdery solids or brittle glasses exhibiting some level/degree of fluorescence when exposed to UV radiation (265-395 nm). The products were characterized by FTIR, $^1$H-NMR, $^{13}$C-NMR and UV/vis-fluorimetry. (FIG. 3C, compounds 26-37, Table 2)

Stoichiometry: [1° amine moiety: ITA]=[1:1] provides compounds of Formula (I) where W is 1; R$^2$ is —CO$_2$H; m is 1; and Q is X—R—N; and [1° amine moiety: ITA/ITE]=[4:1] provides compounds of Formula (I) where W is 1; R$^2$ is —CO$_2$H; m is 1 and Q is R(X)N where R is C$_2$-C$_{18}$ alkylene, —(NHCH$_2$CH$_2$)$_n$, arylene, alkylarylene, oligomers, macrocyclics, fused bicyclics, linear poly(amides), n is 0, 1-4; and X is —OH, —NR$_2$, NHR, —SH, —CO$_2$H. These compounds can be further reacted to form polymers containing pyrrolidone rings in a linear polymer or as a heterocyclic entity containing 2 pyrrolidone moieties. More specifically, the reaction can be described as follows.

To a solution of 50 mmol of primary amine dissolved in 15 mL of MeOH was added to 50 mmol of DMI (7.9 g). The solution was stirred at RT overnight, and then the solvent was removed by distillation in vacuo to give the desired product. See structures on FIG. 3C, compounds numbered 26-37 and data in Table 2.

Subsequent reaction of these intermediates produces the expected linear-poly(amido-pyyrolidone) (PAMPyr) macromolecules which may be considered to be analogues to PEG and poly(oxazoline) type oligomers. For example a mono-BOC-NR(X)NH$_2$ initiator unit followed by linear iterative growth with DMI and excess NH$_2$R(X)NH$_2$ would yield a macromolecule with the general structure shown below after several iterations:

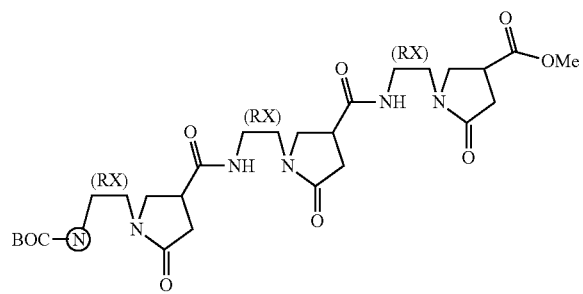

Figure 3D:
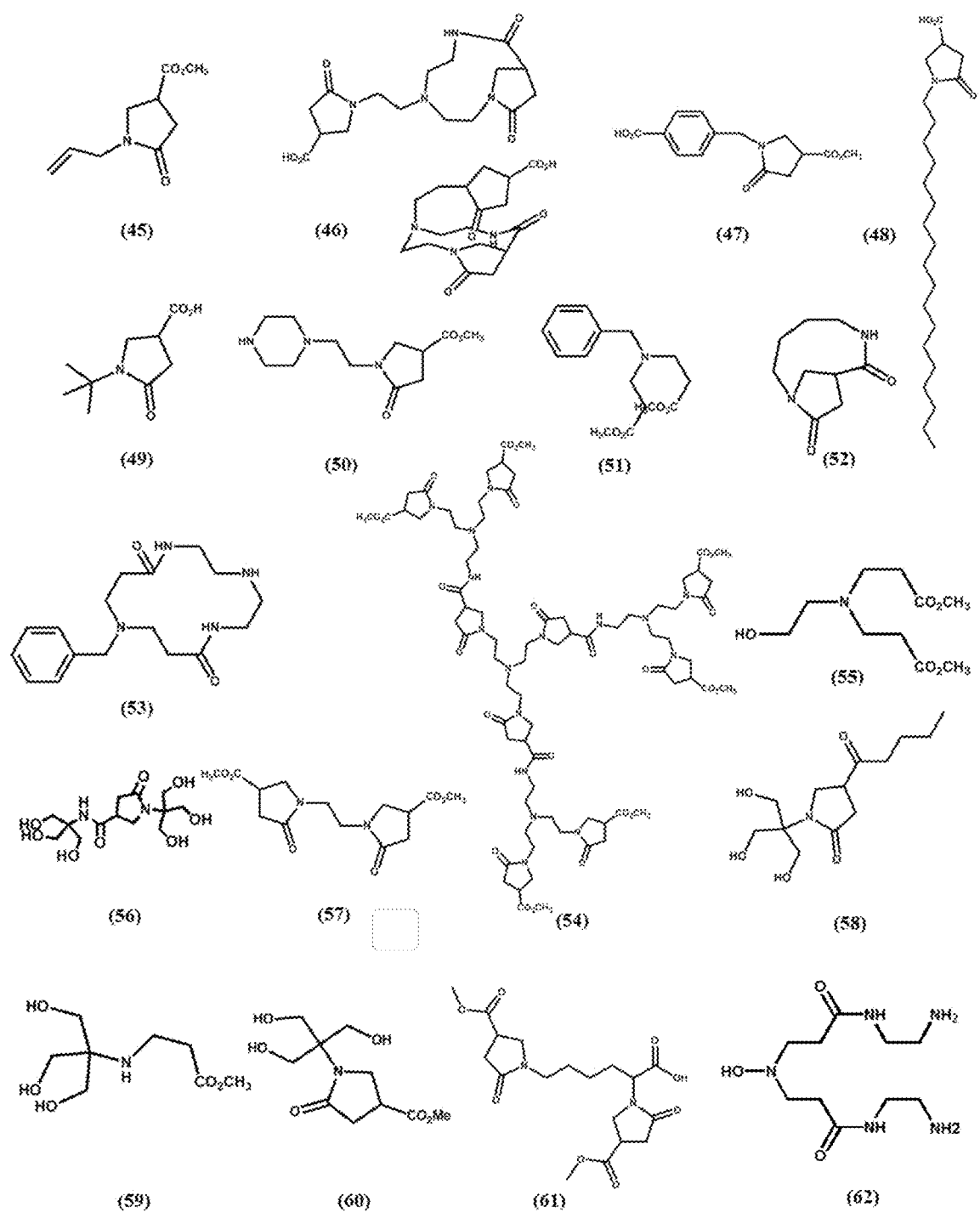

However, the major product type obtained appears to be dependent upon the spacer length of R. When the spacer length R is long, the major product obtained appears to be the linear-poly(amido-pyyrolidone) (PAMPyr) macromolecules. When the spacer R is appropriate to favor intramolecular ring formation, one obtains either fused bicyclic pyrrolidone products and/or macrocylic pyrrolidone products such as shown in FIG. 3D, compounds 40 and 41).

Example 2: General Preparation of N-alkyl-pyrrolidone-4-carboxylic Acids from Primary Amines To 50 mmol of ITA (6.5 g) was added 50 mmol of primary amine. The mixture was heated at 125° C. for 2 h. The mixture was triturated with MeOH to give a white precipitate that was isolated by filtration.

Example 3: General Preparation of N-alkyl-pyrrolidone-4-(N-2-aminoethyl)carboxamides from N-alkyl-carbomethoxypyrrolidones A solution of N-alkyl-4-carbomethoxypyrrolidone in MeOH (50% by weight) was added to excess EDA (25 mol per mol of ester) with stirring. The solution was maintained at RT for 4 days. Excess EDA was removed by distillation, in vacuo, followed by azeotropic distillation with toluene, in vacuo, to give the desired product.

Example 4: General Preparation of N-alkyl-pyrrolidone-4-(N-2-(bis(2-aminoethyl)aminoethyl)carboxamides from N-alkyl-carbomethoxypyrrolidones A solution of N-alkyl-4-carbomethoxypyrrolidone in MeOH (50% by weight) was added to excess TREN (25 mol per mol of ester) with stirring. The solution was maintained at RT for 4 days. Excess TREN was removed by dilution with water and ultrafiltration using a 1kDa cutoff regenerated cellulose membrane to give the desired product.

Note! Using an iterative sequence consisting of reacting a primary amine with DMI to give the 4-(N-2-(bis(2-aminoethyl)aminoethyl)carboxamide pyrrolidone, as above, followed by reaction with an excess of TREN produces a generational sequence for a series of PAMPyrAM dendrons. These dendrons are represented by the Category (IV); [Core]; dendritic-poly(amido)pyrrolidone amine dendrons in FIG. 10.

Example 5: General Preparation of Polymeric N-aminoalkyl-pyrrolidone-4-(N-aminoalkyl)carboxamides from Primary Diamines To a solution of 50 mmol of primary diamine (e.g. EDA 3.0 g) dissolved in 15 mL of MeOH was added 50 mmol of DMI (7.9 g). The solution was stirred at RT for 4 days, and then the solvent was removed by distillation in vacuo to give the desired product.

The 2,4-diamino pyrrolidones, derived from the stoichiometric reaction of 2 moles of diamine with 1 mole of itaconic acid, may be used as intermediates in combination with 2,4-dicarboxylic acid pyrrolidones derived from the reaction of 1× mole amino acid with itanonic acid to produce the corresponding linear-amido-pyrrolidone (i.e., amido-pyrrolidone nylons) which may be considered to be linear-poly(amido-pyrrolidone) mimics of poly(ethyleneglycol). (See FIG. 3D, compounds 38 and 39.)

When stoichiometry of 1° amine moiety: itaconic acid/ester=4:1, one obtains the corresponding di-substituted pyrrolidones (i.e., 2-(NH$_2$—R(X))-4-(CONH—R(X)—NH$_2$) Pyrrolidones) as described below:

NH$_2$—R(X)NH$_2$+itaconic acid/ester→2-(NH$_2$—R(X))-4-(CONH—R(X)—NH$_2$) Pyrrolidone Examples of these 2,4-disubstituted pyrrolidone products are shown in FIG. 3D, compounds 42 and 43).

Preparation of PAMAM Dendrimer Pyrrolidone Surface from Primary Amine Surface Dendrimer and Dimethyl Itaconate

Example 6: [Core: DAB]; (4→2); Dendri-{poly(amidoamine)-(Pyr-4-CO$_2$Me)$_4$}; (G=0); PAMAM Dendrimer; MW=1049

To a stirred mixture of DMI (1.3 g, 8.2 mmol, 10% excess) in 5 mL of MeOH cooled to 5° C. was added dropwise a solution of: [DAB core]; dendri-{poly(amidoamine)-(NH$_2$)$_4$}; (G=0); (PAMAM) dendrimer, (1.0 g, 1.8 mmol, 7.3 mmol amino groups) in 5 mL of MeOH over 2-3 minutes. This mixture was warmed to RT and stirred for 24 h. The reaction mixture was spotted on a TLC plate and stained with ninhydrin solution to give a negative test. The reaction mixture was evacuated free of volatiles using a Buchi rotary evaporator. The resulting residue was dissolved in 10 mL of water and washed with diethyl ether (3×5 mL). The aqueous layer was stripped free of volatiles and the resulting residue re-dissolved in 10 mL of MeOH. The volatiles were removed from this sample using a Buchi rotary evaporator. This process was repeated three times to give, after a final solvent removal under high vacuum, 1.8 g (96% yield) of the title compound that has the following spectra:

$^{13}$CNMR (75 MHz, D$_2$O) δ 23.32, 32.00, 33.72, 35.62, 36.22, 41.94, 48.64, 49.55, 52.35, 52.79, 174.55, 175.43, 176.75.

Example 7: [Core: DAB]; (4→2); Dendri-{poly(amidoamine)-(Pyr-4-CO$_2$Me)$_8$}; (G=1); PAMAM Dendrimer; MW=2466

To a stirred mixture of DMI (1.9 g, 12 mmol, 10% excess) in 5 mL of MeOH cooled to 5° C. was added a solution of: [DAB core]; dendri-{poly(amidoamine)-(NH$_2$)$_8$}; (G=1); (PAMAM) dendrimer, (2.0 g, 1.4 mmol, 11 mmol amino groups) in 5 mL of MeOH dropwise over 2-3 minutes. This mixture was warmed to RT and stirred for 24 h. The reaction mixture was spotted on a TLC plate and stained with ninhydrin solution to give a negative test. The reaction mixture was evacuated of volatiles using a rotary evaporator and the resulting residue dissolved in 10 mL of water. This mixture was washed with diethyl ether (3×5 mL). The aqueous layer was stripped of volatiles and the resulting residue re-dissolved in 10 mL of MeOH. The volatiles were removed using a rotary evaporator. This process was repeated three times to give, after a final evacuation with high vacuum, 3.3 g (95% yield) of the title compound that has the following spectra:

$^{13}$CNMR (75 MHz, D$_2$O) δ 23.32, 32.41, 33.74, 35.66, 36.25, 36.61, 41.96, 48.79, 49.83, 51.08, 52.80, 174.69, 175.42, 176.73.

Example 8: [Core: DAB]; (4→2); Dendri-{poly(amidoamine)-(Pyr-4-CO$_2$Me)$_{16}$}; (G=2);PAMAM Dendrimer; MW=5300

To a stirred mixture of DMI (2.5 g, 16 mmol, 10% excess) in 10 mL of MeOH cooled at 5° C. was added dropwise a solution of: [DAB core]; dendri-{poly(amidoamine)-(NH$_2$)$_8$}; (G=2); (PAMAM) dendrimer, (3.0 g, 0.91 mmol, 14.6 mmol amino groups) in 15 mL of MeOH over 2-3 min. This mixture was warmed to RT and stirred for 24 h. The reaction mixture was spotted on a TLC plate and stained with ninhydrin solution to give a negative test. The reaction mixture was evacuated of volatiles using a rotary evaporator and the resulting residue dissolved in 20 mL of water. This mixture was washed with diethyl ether (3×5 mL). The aqueous layer was stripped of volatiles and the resulting residue redissolved in 10 mL of MeOH. The volatiles were removed using a rotary evaporator. This process was repeated three times to give, after a final evacuation with high vacuum, 4.6 g (95% yield) of the title compound.

In a second purification procedure, the reaction mixture was diluted to 100 mL in MeOH and ultrafiltered to give 8 retentate volumes of permeate using a tangential flow ultrafiltration apparatus containing regenerated cellulose membranes with a 1000 molecular weight cut off. The retentate was stripped of volatiles using a rotary evaporator followed by high vacuum to give 4.6 g (95% yield) of the title compound.

The title compound has the following spectra:
$^{13}$CNMR (75 MHz, D$_2$O) δ 32.38, 33.70, 35.59, 36.20, 36.55, 41.92, 48.73, 48.81, 49.52, 51.06, 52.74, 174.38, 174.63, 175.35, 176.68.

Example 9: [Core: DAB]; (4→2); Dendri-{poly(amidoamine)-(Pyr-4-CO$_2$Me)$_{32}$}; (G=3); PAMAM Dendrimer; MW=10969

To a stirred mixture of DMI (3.2 g, 20.3 mmol, 10% excess) in 15 mL of MeOH cooled at 5° C. was added: PAMAM dendrimer, DAB core, G=0 (4.0 g, 0.58 mmol, 18.5 mmol amino groups) in 15 mL of MeOH dropwise over 2-3 min. This mixture was warmed to RT and stirred for 24 h. The reaction mixture was spotted on a TLC plate and stained with ninhydrin solution to give a negative test. The reaction mixture was evacuated of volatiles using a rotary evaporator and the resulting residue dissolved in 30 mL of water. This mixture was washed with diethyl ether (3×5 mL). The aqueous layer was stripped of volatiles using a rotary evaporator followed by high vacuum to give 6.0 g (94% yield) of the title compound.

In a second purification procedure, the reaction mixture was diluted to 100 mL in MeOH and ultra-filtered to give 8× retentate volumes of permeate using a tangential flow ultrafiltration apparatus containing regenerated cellulose membranes with a 1000 molecular weight cut off. The retentate was stripped of volatiles using a rotary evaporator followed by high vacuum to give 6.0 g (94% yield) of the title compound.

The title compound has the following spectra:
$^{13}$CNMR (75 MHz, D$_2$O) δ 32.43, 32.60, 33.71, 35.62, 36.22, 36.60, 41.95, 48.76, 48.84, 48.94, 49.54, 51.08, 52.77, 174.35, 174.63, 175.33, 176.65.

Example 10: [Core: DAB]; (4→2); Dendri-{poly(amidoamine)-(Pyr-4-CO$_2$Me)$_{64}$}; (G=4); PAMAM Dendrimer; MW=22,307

To a stirred mixture of DMI (4.7 g, 30 mmol, 10% excess) in 20 mL of MeOH cooled at 5° C. was added: PAMAM dendrimer, DAB core, G=0 (6.0 g, 0.42 mmol, 27 mmol amino groups) in 25 mL of MeOH dropwise over 2-3 min. This mixture was warmed to RT and stirred for 24 h. The reaction mixture was spotted on a TLC plate and stained with ninhydrin solution to give a negative test. The reaction mixture was evacuated of volatiles using a rotary evaporator and the resulting residue dissolved in 30 mL of water. This mixture was washed with diethyl ether (3×5 mL). The aqueous layer was stripped of volatiles to give 8.9 g (95% yield) of the title compound.

In a second purification procedure, the reaction mixture was diluted to 100 mL in MeOH and ultrafiltered to give 8 retentate volumes of permeate using a tangential flow ultrafiltration apparatus containing regenerated cellulose membranes with a 1000 molecular weight cut off. The retentate was stripped of volatiles using a rotary evaporator followed by high vacuum to give 8.9 g (95% yield) of the title compound.

The title compound has the following spectra:
$^{13}$CNMR (75 MHz, D$_2$O) δ 32.45, 32.60, 33.71, 35.62, 36.22, 36.60, 41.95, 48.76, 48.84, 48.94, 49.52, 51.08, 52.77, 174.32, 174.60, 175.28, 176.61.

Preparation of [DAB: core]; dendri-{Poly(amidoamine)-(4-Amidoethylamino Pyrrolidone)z}; (G=0-5); PAMAM Dendrimers Example 11: [Core: DAB]; (4→2); Dendri-{poly(amidoamine)-(Pyr-4-CONHCH$_2$CH$_2$NH$_2$)$_4$}; (G=0); PAMAM Dendrimer To a 250 mL round bottom flask containing a stir bar was added 57 g of a 80% EDA-20% MeOH mixture, w/w, 100 equivalents per ester. This mixture was cooled to 8° C. and a MeOH solution of PAMAM dendrimer, DAB core, G=0 pyrrolidone surface (MW=1049) (2.0 g, 1.91 mmol, 7.6 mmol ester) was added dropwise over about 1-2 min. This resulting mixture was allowed to warm to RT and stirred for 2 days. An infrared spectrum of this material (evacuate an aliquot with high vacuum) indicated the reaction was about 95% complete as determined from the disappearance of the ester carbonyl group at 1738 cm$^{-1}$. This mixture was stripped of volatiles on a rotary evaporator. The resulting residue was dissolved in 15 mL of MeOH and 40 mL of toluene was added and mixed to form a homogeneous solution. This mixture was stripped on the rotary evaporator to azeotrope the EDA out of the mixture. This process was repeated six times or until a TLC (silica gel, 10% NH$_4$OH in MeOH) indicated the absence of EDA by development of the dried TLC plate in an iodine chamber. This mixture was dissolved in MeOH and filtered and stripped of volatiles on a rotary evaporator followed by high vacuum at 50° C. for 1 h to give 2.1 g (95%) (MW=1161) that has the following spectra:
$^{13}$CNMR (75 MHz, D$_2$O) δ 23.64, 32.32, 34.54, 36.17, 36.61, 39.55, 41.71, 41.92, 48.58, 48.76, 50.28, 52.35, 174.89, 175.45, 176.87.

Example 12: [Core: DAB]; (4→2); Dendri-{poly(amidoamine)-(Pyr-4-CONHCH$_2$CH$_2$NH$_2$))$_8$}; (G=1); PAMAM Dendrimer This product was prepared in the same manner as PAMAM Dendrimer, DAB core, G=0 Pyrrolidone amidoethylamine using PAMAM dendrimer, DAB core, G=1Pyrrolidone methoxy ester (MW=2466) (2 g, 0.81 mmol, 6.5 mmol ester), 97 g of a 80% EDA-20% MeOH mixture, w/w, 200 equivalents per ester to give 2.0 g (95% yield) of the title compound that has the following spectra:
$^{13}$CNMR (75 MHz, D$_2$O) δ 23.71, 32.29, 32.42, 34.48, 36.14, 36.64, 39.56, 40.15, 41.25, 41.33, 41.91, 48.70, 48.74, 50.22, 50.96, 52.44, 174.52, 174.74, 175.42, 175.80.

Example 13: [Core: DAB]; (4→2); Dendri-{poly(amidoamine)-(Pyr-4-CONHCH$_2$CH$_2$NH$_2$))$_{16}$}; (G=2); PAMAM Dendrimer

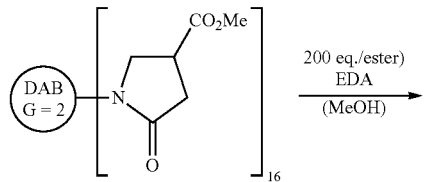

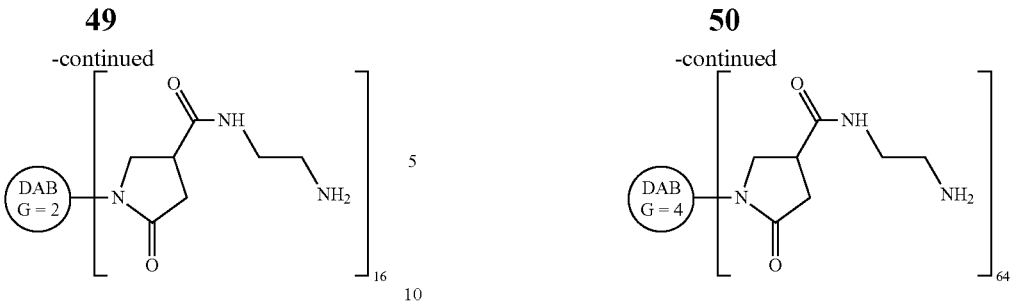

This product was prepared in the same manner as PAMAM Dendrimer, DAB core, G=0; Pyrrolidone amidoethylamine using PAMAM Dendrimer, DAB core, G=2 Pyrrolidone methoxy ester (MW=2466) (2 g, 0.81 mmol, 6.5 mmol ester), 97 g of a 80% EDA-20% MeOH mixture, w/w, 200 equivalents per ester to give 2.1 g (97% yield) of the title compound that has the following spectra:

$^{13}$CNMR (75 MHz, D$_2$O) δ 32.51, 32.51, 34.54, 36.20, 36.61, 39.65, 41.54, 41.59, 41.95, 48.82, 48.94, 50.21, 51.08, 174.46, 174.75, 175.42, 175.03.

Example 14: [Core: DAB]; (4→2); Dendri-{poly(amidoamine)-(Pyr-4-CONHCH$_2$CH$_2$NH$_2$))$_{32}$}; (G=3); PAMAM Dendrimer

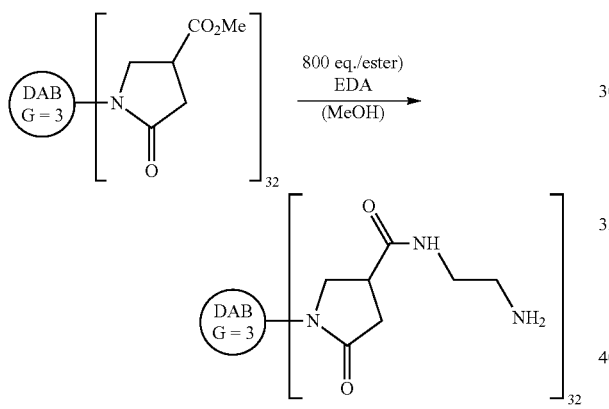

This product was prepared in the same manner as PAMAM Dendrimer, DAB core, G=0 Pyrrolidone amidoethylamine using PAMAM Dendrimer, DAB core, G=3 Pyrrolidone carbomethoxy ester (MW=10969); (3 g, 0.27 mmol, 8.7 mmol ester), 522 g of an 80% EDA-20% MeOH mixture, w/w, 800 equivalents per ester to give 3.0 g (93% yield) of the title compound that has the following spectra:

$^{13}$CNMR (75 MHz, D$_2$O) δ 32.52, 32.55, 34.55, 36.22, 36.61, 39.66, 41.71, 41.56, 41.95, 48.83, 50.29, 51.11, 174.42, 174.72, 175.41, 175.80.

Example 15: [Core: DAB]; (4→2); Dendri-{poly(amidoamine)-(Pyr-4-CONHCH$_2$CH$_2$NH$_2$))$_{64}$}; (G=4); PAMAM Dendrimer

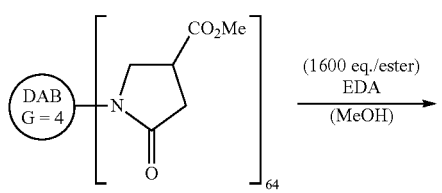

This product was prepared in the same manner as PAMAM Dendrimer, DAB core, G=0 Pyrrolidone amidoethylamine using PAMAM Dendrimer, DAB core, G=4 Pyrrolidone methoxy ester (MW=22307) (2 g, 0.09 mmol, 5.7 mmol ester), 714 g of a 80% EDA-20% MeOH mixture, w/w, 1600 equivalents per ester to give 2.0 g (92% yield) of the title compound that has the following spectra:

$^{13}$CNMR (75 MHz, D$_2$O) δ 32.52, 34.55, 36.20, 36.61, 39.70, 41.62, 41.65, 41.95, 48.78, 48.83, 50.29, 51.11, 174.38, 174.69, 175.36, 175.77.

Example 16: [Core: DAB]; (4→2); Dendri-{Poly(amidoamine)-(Pyr-4-CONHCH$_2$CH$_2$NH$_2$))$_{128}$}; (G=5); PAMAM Dendrimer

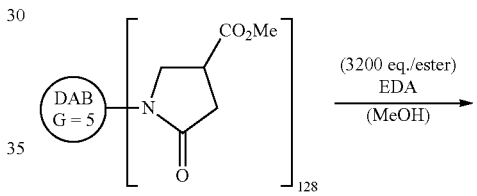

This product was prepared in the same manner as PAMAM Dendrimer, DAB core, G=0 Pyrrolidone amidoethylamine using PAMAM Dendrimer, DAB core, G=5 Pyrrolidone methoxy ester (MW=44782) (1.5 g, 0.03 mmol, 4.2 mmol ester), 1024 g of a 80% EDA-20% MeOH mixture, w/w, 3200 equivalents per ester to give 1.45 g (91% yield) of the title compound that has the following spectra:

$^{13}$CNMR (75 MHz, D$_2$O) δ 32.64, 34.55, 36.20, 36.61, 39.73, 41.66, 41.95, 48.76, 48.87, 50.28, 51.16, 174.32, 174.64, 175.30, 176.72.

Preparation of PAMAM Dendrimer, DAB core, Pyrrolidone-3-Carboamidoethylamino-N,N'-bis-ethylamine Surface Example 17: [Core: DAB]; (4→2); Dendri-{poly(amidoamine)-(Pyr-4-CONH-TREN)$_{16}$}; (G=2); PAMAM Dendrimer

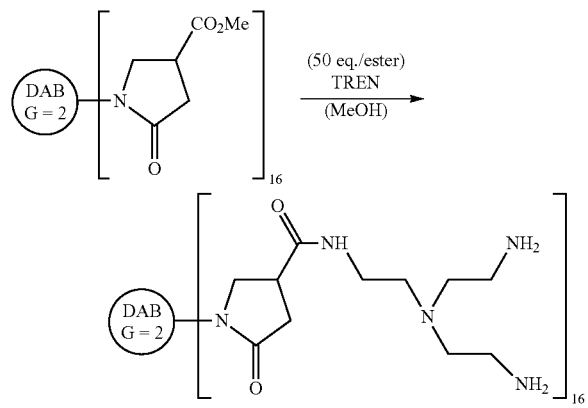

This product was prepared in a 100 mL round bottom flask containing a stir bar using PAMAM dendrimer, DAB core, G=2; pyrrolidone carbomethoxy ester (MW=5300) (1 g, 0.19 mmol, 3 mmol ester) dissolved in 3 mL of MeOH that was added to a mixture of TREN (22 g, 151 mmol, 50 equivalents per ester) and 6 g of MeOH at 8° C. This mixture was stirred at 25° C. for 4 days. An infrared spectrum of this material indicated the complete disappearance of the ester carbonyl frequency at 1735 cm$^{-1}$. This mixture was diluted with MeOH to give a 3-5% solution and purified using a tangential flow ultrafiltration device containing 1K regenerated cellulose membrane for 8-10 retentate recirulations or 2400-3000 ml or until a TLC (20% NH$_4$OH in MeOH) indicated the absence of TREN. The volatiles were removed using a rotary evaporator. The residue was dissolved in MeOH and the resulting mixture was evacuated of volatiles on the rotary evaporator for a total of three times. This residue was evacuated at 40° C. for ~2 h with a high vacuum to give 8.7 g (93% yield) of the desired product (MW=6295) as a white solid. The dialyzed mixture was evacuated of volatiles on a rotary evaporator. The residue was redissolved in MeOH followed by removal of volatiles three times and evacuated at high vacuum at 40° C. for 1 h to give 1.2 g (97% yield) of the title compound that has the following spectra:

$^{13}$CNMR (75 MHz, D$_2$O) δ 32.51, 35.54, 36.22, 36.58, 36.87, 37.71, 41.98, 48.78, 50.24, 51.11, 52.42, 55.47, 174.53, 174.73, 175.07, 175.79.

Preparation of PAMAM Dendrimer Pyrrolidone Sodium Carboxylate Surface

Example 18: [Core: DAB]; (4→2); Dendri-{poly(amidoamine)-(Pyr-4-CO$_2^-$Na$^+$)$_{16}$}; (G=2); PAMAM Dendrimer This product was prepared in a 25 mL round bottom flask containing a stir bar using PAMAM Dendrimer, DAB core, G=2 Pyrrolidone methoxy ester (MW=5300) (1 g, 0.19 mmol, 3 mmol ester) dissolved in 3 mL of deionized water that was added to sodium carbonate monohydrate (MW=124) (450 mg, 3.6 mmol, 1.3 equivalents per ester) dissolved in 4 mL of deionized water. This mixture was stirred at 25° C. for 3 days. An infrared spectrum of this material indicated the complete disappearance of the ester carbonyl frequency at 1735 cm$^{-1}$. This mixture was diluted with deionized water to give a 3-5% solution and dialyzed in a regenerated cellulose membrane with a 1000 molecular weight cutoff. The 250 mL dialysate was changed 10 times with 2-18 h between changes. The dialyzed mixture was evacuated of volatiles on a rotary evaporator. The residue was re-dissolved in MeOH followed by removal of volatiles three times and evacuated at high vacuum at 40° C. for 1 h to give 1.9 g (97% yield) of the title compound that has the following spectra:

$^{13}$CNMR (75 MHz, D$_2$O) δ 32.25, 35.15, 36.35, 38.53, 41.91, 48.87, 51.05, 51.20, 174.40, 174.58, 176.77, 180.98.

Preparation of PAMAM Dendrimer Pyrrolidone Amidoethanol Surface

Example 19: [Core: DAB]; (4→2); Dendri-{poly(amidoamine)-(Pyr-4-CONHCH$_2$CH$_2$OH)$_4$}; (G=0); PAMAM Dendrimer To a 250 mL round bottom flask containing a stir bar was added 37 g of a 80% EA-20% MeOH mixture, w/w, 100 equivalents per ester. This mixture was cooled to 8° C. and a MeOH solution of PAMAM dendrimer, DAB core, G=0 pyrrolidone surface (MW=2466) (1.5 g, 0.61 mmol, 4.9 mmol ester) was added dropwise over about 1-2 min. This resulting mixture was allowed to warm to RT and stirred for 2 days. An infrared spectrum of this material (evacuate an aliquot with high vacuum) indicated the reaction was about 95% complete as determined from the disappearance of the ester carbonyl group at 1738 cm$^{-1}$. This mixture was stripped of EA using a bulb to bulb distillation apparatus at high vacuum and a pot temperature of 120° C. The bulk of the EA was distilled leaving a viscous residue. This residue was dissolved in MeOH to give a 30% w/w solution and loaded on a Sephadex LH-20 column in MeOH. After a void volume was finished a total of 20 fractions were collected each at 20 mL. Fractions were monitored by spotting on a TLC plate and developing in an iodine chamber. Fractions 6-11 were collected, stripped of volatiles to give 1.44 g (95% yield) (MW=2474) of the title compound that has the following spectra:

$^{13}$CNMR (75 MHz, D$_2$O) δ 23.64, 32.02, 32.51, 34.55, 36.23, 36.60, 39.55, 41.57, 41.98, 48.84, 50.33, 51.06, 52.53, 59.91, 174.41, 174.80, 175.44, 175.91.

Example 20: [Core: DAB]; (4→2); Dendri-{poly(amidoamine)-(Pyr-4-CONHCH$_2$CH$_2$OH)$_8$}; (G=1); PAMAM Dendrimer To a 250 mL round bottom flask containing a stir bar was added 37 g of a 80% EA-20% MeOH mixture, w/w, 100 equivalents per ester. This mixture was cooled to 8° C. and a MeOH solution of PAMAM dendrimer, DAB core, G=1 pyrrolidone surface (MW=2466) (1.5 g, 0.61 mmol, 4.9 mmol ester) was added dropwise over about 1-2 min. This resulting mixture was allowed to warm to RT and stirred for 2 days. An infrared spectrum of this material (evacuate an aliquot with high vacuum) indicated the reaction was about 95% complete as determined from the disappearance of the ester carbonyl group at 1738 cm$^{-1}$. This mixture was stripped of EA using a bulb to bulb distillation apparatus at high vacuum and a pot temperature of 120° C. The bulk of the EA was distilled leaving a viscous residue. This residue was dissolved in MeOH to give a 30% w/w solution and loaded on a Sephadex LH-20 column in MeOH. After a void volume was finished a total of 20 fractions were collected each at 20 mL. Fractions were monitored by spotting on a TLC plate and developing in an iodine chamber. Fractions 6-11 were collected, stripped of volatiles to give 1.44 g (95% yield) (MW=2474) of the title compound that has the following spectra:

$^{13}$CNMR (75 MHz, D$_2$O) δ 23.51, 32.19, 32.48, 34.54, 36.23, 36.58, 41.56, 41.93, 48.72, 48.82, 50.32, 51.05, 59.79, 174.40, 174.44, 175.90.

Example 21: [Core: DAB]; (4→2); Dendri-{poly (amidoamine)-(Pyr-4-CONHCH$_2$CH$_2$OH)$_{16}$}; (G=2); PAMAM Dendrimer

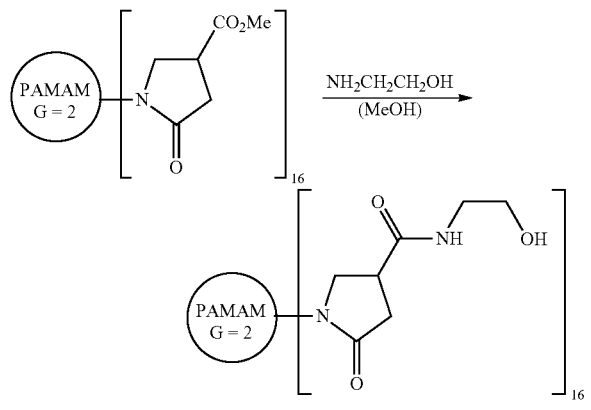

This product was prepared in a 25 mL round bottom flask containing a stir bar using PAMAM dendrimer, DAB core, G=2 pyrrolidone methoxy ester (MW=5300) (2 g, 0.38 mmol, 6.0 mmol ester) dissolved in 8 mL of MeOH that was added to 5 g of a 80% EA-20% MeOH mixture (w/w), ~10 equivalents amine per ester. This mixture was stirred at 25° C. for 3 days. An infrared spectrum of this material indicated the complete disappearance of the ester carbonyl frequency at 1735 cm$^{-1}$. This mixture was diluted with deionized water to give a 3-5% solution and dialyzed in a regenerated cellulose membrane with a 1000 molecular weight cutoff. The 1 liter dialysate was changed 10 times with 2-18 h between changes. The dialyzed mixture was evacuated of volatiles on a rotary evaporator. The residue was redissolved in MeOH followed by removal of volatiles three times and evacuated at high vacuum at 40° C. for 1 h to give 2.1 g (97% yield) of the title compound.

Example 22: [Core: DAB]; (4→2); Dendri-{poly (amidoamine)-(Pyr-4-CONHCH$_2$CH$_2$OH)$_{32}$}; (G=3); PAMAM Dendrimer This product was prepared using PAMAM Dendrimer, DAB core, G=3 Pyrrolidone methoxy ester (MW=10969)(2 g, 0.18 mmol, 5.8 mmol ester) dissolved in 8 mL of MeOH and added to 5 g of a 80% EA-20% MeOH mixture (w/w), 10 equivalents amine per ester. This mixture was stirred at 25° C. for 3 days. An infrared spectrum of this material indicated the complete disappearance of the ester carbonyl frequency at 1735 cm$^{-1}$. This mixture was diluted with deionized water to give a 3-5% solution and dialyzed in a regenerated cellulose membrane with a 1000 molecular weight cutoff. The 1 liter dialysate was changed 10 times with 2-18 h between changes. The dialyzed mixture was evacuated of volatiles on a rotary evaporator. The residue was redissolved in MeOH followed by removal of volatiles three times and evacuated at high vacuum at 40° C. for 1 h to give 2.1 g (97% yield) of the title compound that has the following spectra:

$^{13}$CNMR (75 MHz, D$_2$O) δ 32.60, 34.55, 36.23, 36.61, 41.71, 41.59, 41.95, 48.79, 48.84, 48.97, 52.32, 174.43, 174.74, 175.38, 176.85.

Example 23: [Core: DAB]; (4→2); Dendri-{poly (amidoamine)-(Pyr-4-CONHCH$_2$CH$_2$OH)$_{64}$}; (G=4); PAMAM Dendrimer This product was prepared using PAMAM Dendrimer, DAB core, G=4 Pyrrolidone methoxy ester (MW=22,307)(2 g, 0.09 mmol, 5.7 mmol ester) dissolved in 8 mL of MeOH and added to 5 g of a 80% EA-20% MeOH mixture (w/w), 10 equivalents amine per ester. This mixture was stirred at 25° C. for 3 days. An infrared spectrum of this material indicated the complete disappearance of the ester carbonyl frequency at 1735 cm$^{-1}$. This mixture was diluted with deionized water to give a 3-5% solution and dialyzed in a regenerated cellulose membrane with a 1000 molecular weight cutoff. The 1 liter dialysate was changed 10 times with 2-18 h between changes. The dialyzed mixture was evacuated of volatiles on a rotary evaporator. The residue was redissolved in MeOH followed by removal of volatiles three times and evacuated at high vacuum at 40° C. for 1 h to give 2.1 g (97% yield) of the title compound that has the following spectra:

$^{13}$CNMR (75 MHz, D$_2$O) δ 32.52, 34.55, 36.23, 36.58, 41.61, 41.95, 48.85, 48.96, 50.30, 59.91, 174.34, 174.40, 174.71, 175.33, 175.80.

Example 24: Core: DAB]; (4→2); Dendri-{poly (amidoamine)-(Pyr-4-CONHCH$_2$CH$_2$OH)$_{128}$; (G=5); PAMAM Dendrimer This product was prepared using PAMAM Dendrimer, DAB core, G=5 Pyrrolidone methoxy ester (MW=44982)(2 g, 0.04 mmol, 5.7 mmol ester) dissolved in 8 mL of MeOH and added to 75 g of a 80% EA-20% MeOH mixture (w/w), 10 equivalents amine per ester. This mixture was stirred at 25° C. for 3 days. An infrared spectrum of this material indicated the complete disappearance of the ester carbonyl frequency at 1735 cm$^{-1}$. This mixture was diluted with deionized water to give a 3-5% solution and dialyzed in a regenerated cellulose membrane with a 1000 molecular weight cutoff. The 1 liter dialysate was changed 10 times with 2-18 h between changes. The dialyzed mixture was evacuated of volatiles on a rotary evaporator. The residue was redissolved in MeOH followed by removal of volatiles three times and evacuated at high vacuum at 40° C. for 1 h to give 2.1 g (97% yield) of the title compound.

Preparation of PAMAM Dendrimer, [DAB core], (G=1) Pyrrolidone amidoethyl amine pyrrolidone Surface: Proof of structure for conversion of Pyrrolidone carbomethoxy surface to Pyrrolidone amidoethylamine surface in a PAMAM dendrimer Example 25: [Core:DAB]; (4→2); Dendri-{poly (amidoamine)-(Pyr-4-CONHCH$_2$CH$_2$NH$_2$)$_8$}; (G=1); PAMAM Dendrimer This product was prepared in the same manner as PAMAM Dendrimer, DAB core, G=0 Pyrrolidone amidoethylamine using PAMAM Dendrimer, DAB core, G=1; Pyrrolidone methoxy ester (MW=2466) (2 g, 0.81 mmol, 6.5 mmol ester), 97 g of a 80% EDA-20% MeOH mixture, w/w, 200 equivalents per ester to give 98% yield that has the following spectra:

$^{13}$CNMR (75 MHz, D$_2$O) δ 23.71, 32.29, 32.42, 34.48, 36.14, 36.64, 39.56, 40.15, 41.25, 41.33, 41.91, 48.70, 48.74, 50.22, 50.96, 52.44, 174.52, 174.74, 175.42, 175.80.

Example 26: [Core: DAB]; (4→2); Dendri-{poly(amidoamine)-(Pyr-4-CONHCH$_2$CH$_2$-N-Pyr-4-COMe)$_8$; (G=1); PAMAM Dendrimer PAMAM Dendrimer, DAB core, G=1 Pyrrolidone amidoethyl pyrrolidone Surface

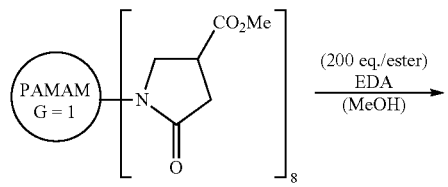

To a stirred mixture of DMI (32 mg, 2 mmol, 10% excess) in 5 mL of MeOH cooled at 5° C. was added PAMAM dendrimer, DAB core, G=1 pyrrolidone amidoethylamine (MW=2690) (600 mg, 0.22 mmol, 1.8 mmol amino groups) in 5 mL of MeOH dropwise over 2-3 min. This mixture was warmed to RT and stirred for 24 h. The reaction mixture was spotted on a TLC plate and stained with ninhydrin solution to give a negative test. The reaction mixture was added to a Sephadex LH=20 column in MeOH and eluted with a 300 mL void volume followed by 20×20 mL fractions. Fractions 6-12 were found to contain the desired product by spotting each fraction on a TLC plate (silica gel, non-fluorescent) and developing the fractions in an iodine chamber. The volatiles of these fractions were removed using a rotary evaporator to give, after a final evacuation with high vacuum, 770 mg (95% yield) of the title compound (MW=3698) that has the following spectra:

$^{13}$CNMR (75 MHz, D$_2$O) δ 32.42, 33.73, 34.40, 36.61, 36.24, 36.38, 36.50, 41.95, 48.81, 48.84, 49.51, 50.15, 51.13, 52.90, 174.69, 175.16, 175.42, 175.70.

Example 27: Linear-Poly (Amido-pyrrolidone) (PAMPyr) Oligomers

These linear-poly(amidopyrrolidone) (PAMPyr) products are analogues to PEGs (Davis et al., *Adv. Drug Delivery Reviews*, 2002, 54(4), 457-458) and PEOx (Harris et al., U.S. Pat. No. 7,943,141, 2011) type polymers. As such they exhibit low toxicity, low complement activation features and may be used to reduce protein interactions with drug conjugates while enhancing in vivo residency times for these conjugates when used as injectables.

The process to prepare these polymers is as follows.

1° Amines/1° Alkylene diamines+n[DMI+excess EDA]→Linear-Poly[(Amido-pyrrolidone)]$_n$ (PAMPyr) Oligomers 1. RNH$_2$+n (DMI+Excess EDA)→R—NH(L-PAMPyr)$_n$-ester/amine terminated 2. BocNHR(X)NH$_2$+n (DMI+Excess EDA)→Boc-NH(L-PAMPyr)$_n$-ester/amine terminated (deprotection) →NH$_2$(L-PAMPyr)$_n$-ester/amine terminated 3. NH$_2$CH$_2$CH$_2$—S—S—CH$_2$CH$_2$NH$_2$+n (DMI+Excess EDA)→[—S—CH$_2$CH$_2$N(L-PAMPyr)$_n$]$_2$→2 HS CH$_2$CH$_2$N(L-PAMPyr)$_n$

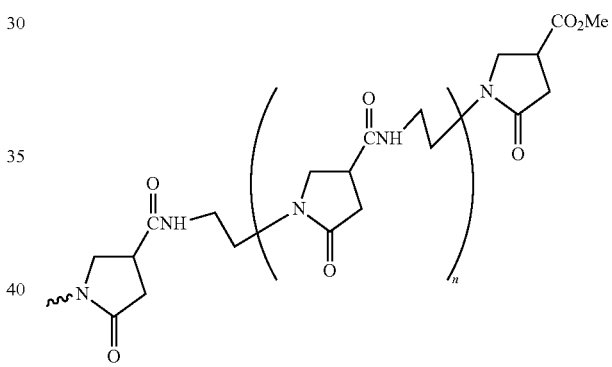

4. (L-PAMPyr)$_n$-ester/amine terminated

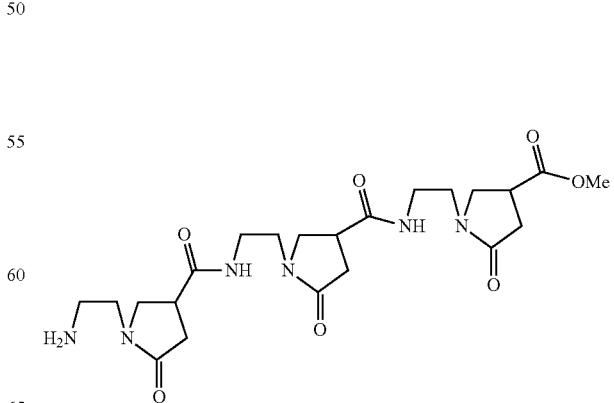

Example 28: Star Branched, Linear-Poly (Amido-pyrrolidones) (PAMPyr)
1. N[(CH$_2$CH$_2$)NH$_2$)]$_3$ (TREN)+n (DMI+Excess EDA) 5
→Dendritic, Poly(amido-pyrrolidone) Amines (PAM-PyrAM)
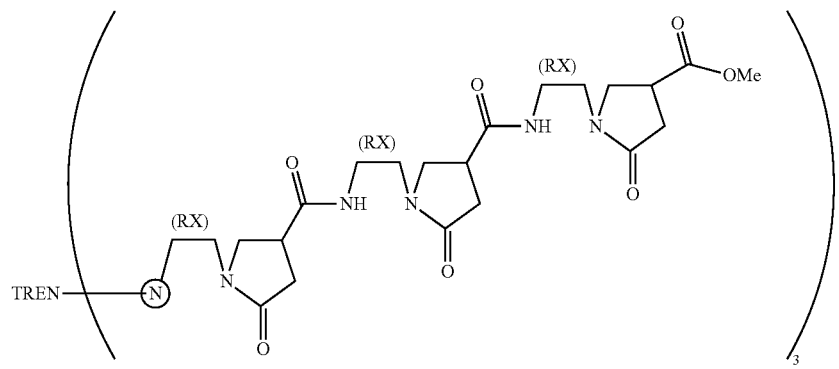
2. N[(CH$_2$CH$_2$)NH$_2$)]$_3$ (TREN)+n (DMI+Excess TREN)→
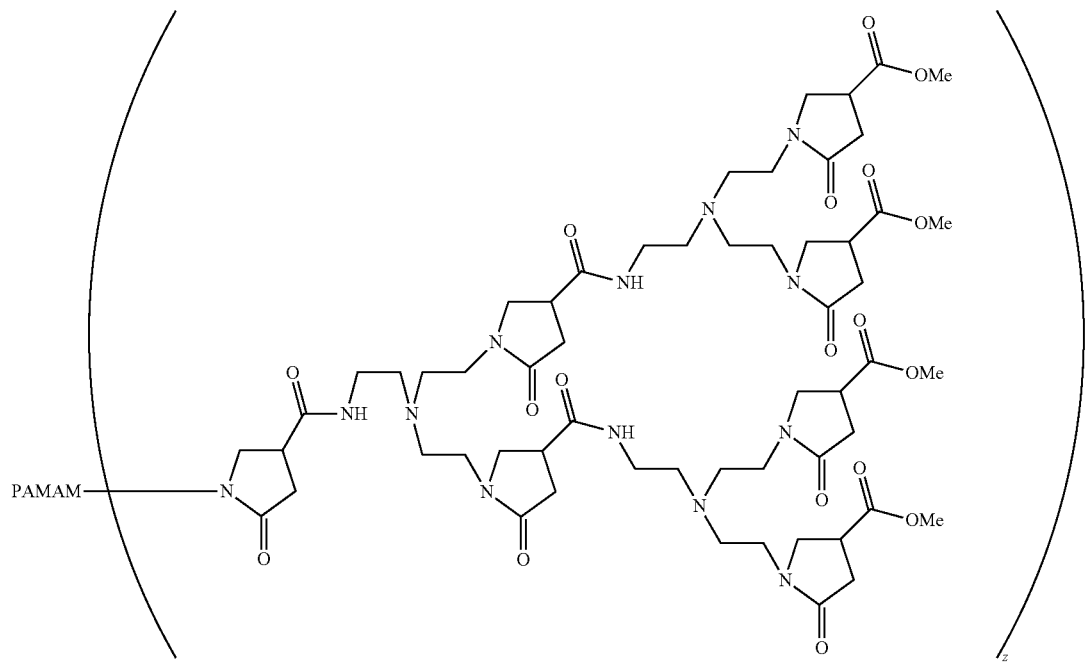

3. PAMAM-(NH$_2$)$_z$+n (DMI+Excess TREN)→

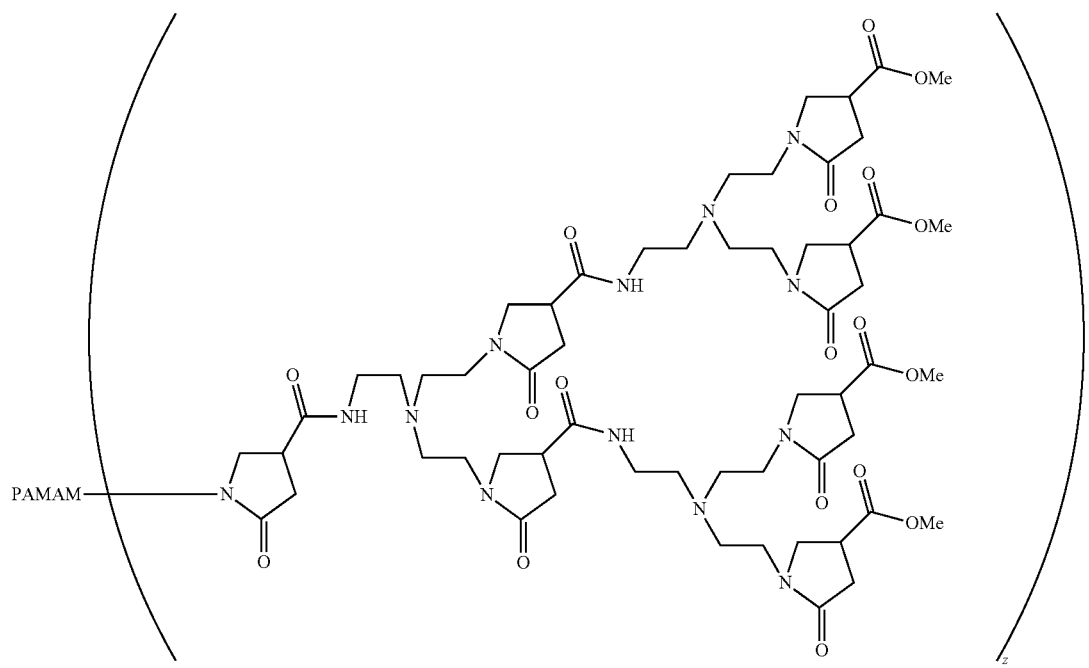

Example 29: Pyrrolidone Terminated PAMAM Dendrimers

Surface functionalized:
Dendrimers (1° amine terminated)+DMI→

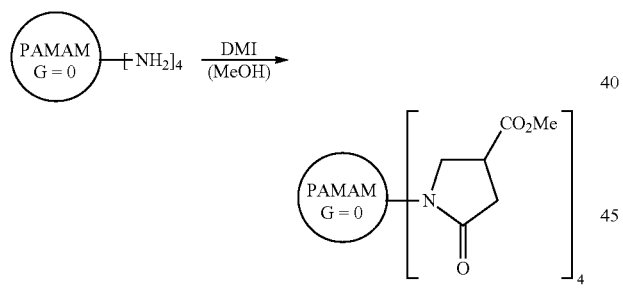

Example 30: Simple Cystamine Core

Cystamine dihydrochloride was first liberated as the free amine by adding a solution of the dihydrochloride (11.80 g, 0.05240 mol, 225.2 g/mol, 96%) (i.e., in water 3 mL) and to a solution of NaOH (8.42 g, 0.2096 mol, 39.997 g/mol) (in 3 mL of H$_2$O) while swirling on ice at RT. Toluene (~20 mL) was added to form a white precipitate (water layer), orange layer, and toluene layer (bottom to top). NaOH pellets were added until the orange layer went into the toluene layer, stirring between each addition. The toluene layer was decanted followed by addition of a second toluene (20 mL) portion with decantation. The toluene layers were combined, filtered and dried on a rotary evaporator to yield 7.07 g (88.4% yield) of a non-viscous pale yellow oily liquid. $^{13}$C NMR confirmed relative purity. The process provides a compound of the following structure.

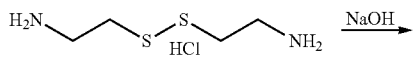

Example 31: Formation of the Di[4-Carbomethoxy Pyrrolidone] from Cystamine

The cystamine (7.07 g, 0.04643 mol, 152.28 g/mol) as a free base in methanol (~7 mL), made by Example 30, was charged into a 100 mL RBF equipped with a magnetic stirrer. While stirring and cooling with ice, DMI (14.69 g, 0.09286 mol, 158.15 g/mol, CAS: 617-52-7, TCI) in methanol (~10 mL) was added dropwise over a period of 15 min. The ice cooled solution was allowed to stir for approximately 1 min and then at RT for 3 days to yield a clear amber solution. TLC and $^{13}$C-NMR were obtained at 2.5 h and 3 days to confirm complete reaction and assess the product purity. This product was designated: [ester-(Pyrr)-SS-(Pyrr)-ester]. The process provides a compound of the following structure.

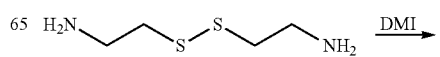

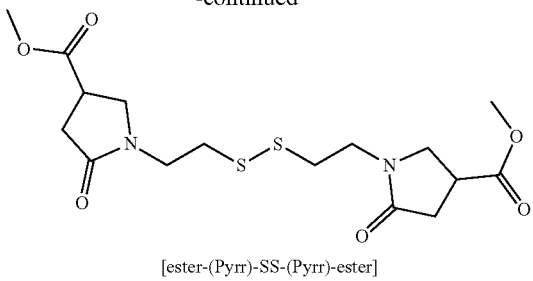

[ester-(Pyrr)-SS-(Pyrr)-ester]

Example 32: First Amidation Extension: [NH₂-(Pyrr)-SS-(Pyrr)-NH₂]

To a RBF(100 mL) containing (~20× excess) EDA (62 mL, 56 g, 0.9286 mol, 60.10 g/mol, d=0.899 g/mL, CAS: 107-15-3) and equipped with a magnetic stirrer, the product [ester-(Pyrr)-SS-(Pyrr)-ester; made by Example 31] (18.78 g, 0.04643 mol, 404.50 g/mol) in MeOH was added dropwise over a period of 1 h, while stirring at RT. The reaction was stirred at RT for 3 days to yield a clear bright yellow solution. Analysis by $^{13}$C-NMR confirmed formation of an amide carbonyl band consistent with the expected product designated as [NH₂-(Pyrr)-SS-(Pyrr)-NH₂]. Excess EDA was removed by azeotroping with toluene (~10 mL) per run. Complete EDA removal was confirmed by TLC (30% NH₄OH in methanol) after 7 azeotropes to yield ~19.2 g (90% yield) of a clear pale orange oil. The process provides a compound of the following structure.

pale yellow solution. Analysis by TLC and $^{13}$C-NMR confirmed product formation and excess DMI. Methanol was removed from the reaction with toluene (5 mL) to yield 4.6 g of crude product. This crude product was run as a plug flow through (25 g silica) using 75 mL of denatured alcohol, followed by an additional 125 mL denatured alcohol, to yield 3.83 g (95.5% yield) of a slightly viscous pale orange oil. Product purity of both fractions was determined by TLC and structure confirmed by $^{13}$C-NMR and FTIR. This product was designated as [ester-(Pyrr)₂-SS-(Pyrr)₂-ester]. The process provides a compound of the following structure.

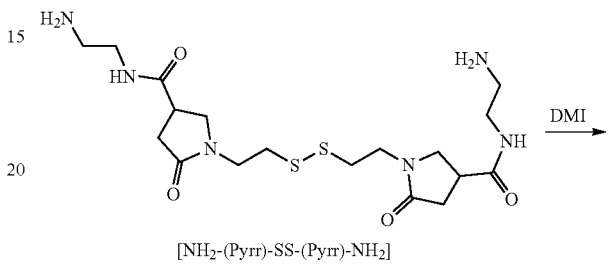

[NH₂-(Pyrr)-SS-(Pyrr)-NH₂]

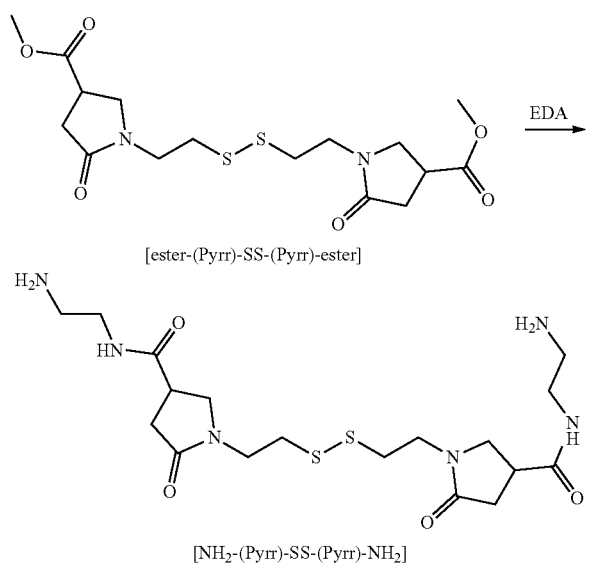

Example 33: Second Pyrrolidonylation Addition: [Ester-(Pyrr)₂-SS-(Pyrr)₂-Ester]

DMI (2.14 g, 0.01351 mol) in 10 mL of methanol was charged into a 50 mLRBFequipped with a magnetic stirrer. While stirring and cooling with ice, a solution of [NH₂-(Pyrr)-SS-(Pyrr)-NH₂; made by Example 32] (2.59 g, 0.005628 mol, 460.61 g/mol) in 10 mL of MeOH was added over a period of 15 min. After stirring in the cold for 10 min the reaction was allowed to stir at RT for 6 days to yield a

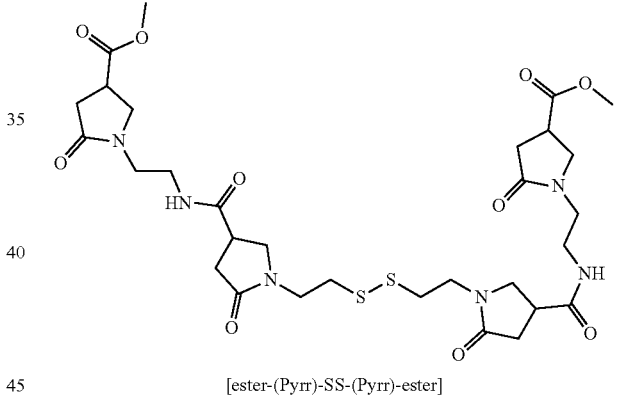

[ester-(Pyrr)-SS-(Pyrr)-ester]

Example 34: Second Amidation Extension: [NH₂-(Pyrr)₂-SS-(Pyrr)₂-NH₂]

EDA (5.45 g, 0.09062 mol) was charged into a 50 mL RBF equipped with a magnetic stirrer. While stirring and cooling with ice [ester-(Pyrr)-SS-(Pyrr)-ester]; made by Example 33] (3.23 g, 0.004531 mol, 712.83 g/mol), dissolved in methanol (i.e.,15 mL) was added drop-wise over a period of 15 min. The reaction mixture was allowed to stir for 20 min on ice and then at RT for 3 days. The excess EDA was azeotroped with 10 mL of toluene. This operation was monitored by silica TLC (i.e., 15% NH₄OH in methanol) and required 11 azeotropes to remove all EDA. The product was a viscous pale yellow oil weighing 4.46 g (128% yield) and was confirmed by silica TLC and $^{13}$C-NMR to be the desired structure containing some residual toluene solvent. The process provides a compound of the following structure.

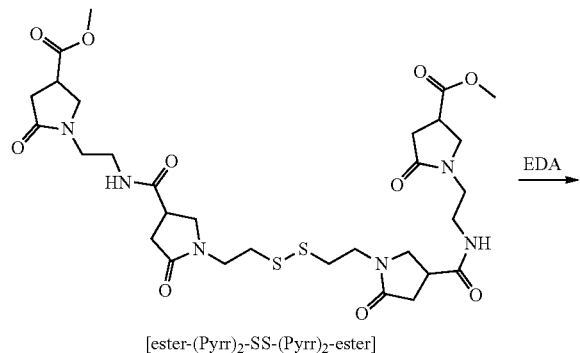

[ester-(Pyrr)₂-SS-(Pyrr)₂-ester]

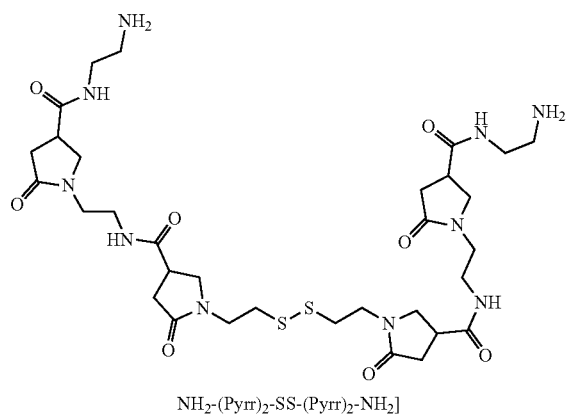

NH₂-(Pyrr)₂-SS-(Pyrr)₂-NH₂]

Example 35: Third Pyrrolidonylation Addition: [Ester-(Pyrr)₃-SS-(Pyrr)₃-Ester]

DMI (1.65 g, 0.01042 mol) in 10 mL of methanol was added dropwise to a stirred solution of NH₂-(Pyrr)₂-SS-(Pyrr)₂-NH₂; made by Example 34] (3.48 g, 0.004531 mol, 768.95 g/mol) in 10 mL of MeOH contained in a 50 mLRBF(i.e., magnetic stirrer) while cooling with ice After stirring in the cold ~5 min, the reaction was allowed to stir at RT for 2 days. Progress of the reaction was followed by $^{13}$C-NMR confirming product formation and the presence of excess DMI by TLC. Added toluene (15 mL) to reaction mixture and decanted; repeated this operation 3 times followed by devolatilized on the rotary evaporator. A chromatographic plug flow separation was done on this crude product (i.e., 25 g silica, 50 mL denatured alcohol, then 100 mL denatured alcohol) to yield 3.45 g of total crude product which appeared to contain some DMI. Minimal methanol was added to decrease the viscosity followed by toluene (10 mL) and decantation. This was repeated 3 times to yield 2.42 g (52.3% yield). Purity and product structure was confirmed by silica TLC (i.e. MeOH) and $^{13}$C-NMR. Although this method did not produce the best yield, it was determined to be the preferred purification method for the removal of excess DMI. The process provides a compound of the following structure.

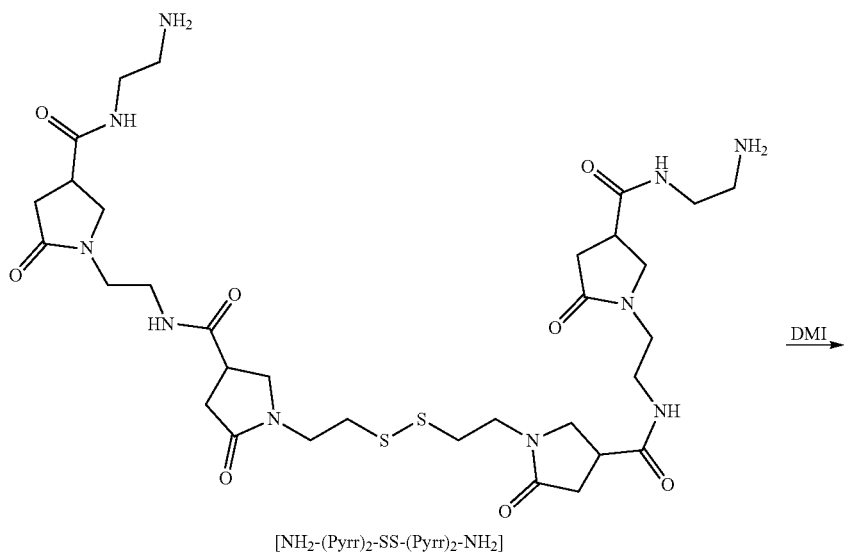

[NH₂-(Pyrr)₂-SS-(Pyrr)₂-NH₂]

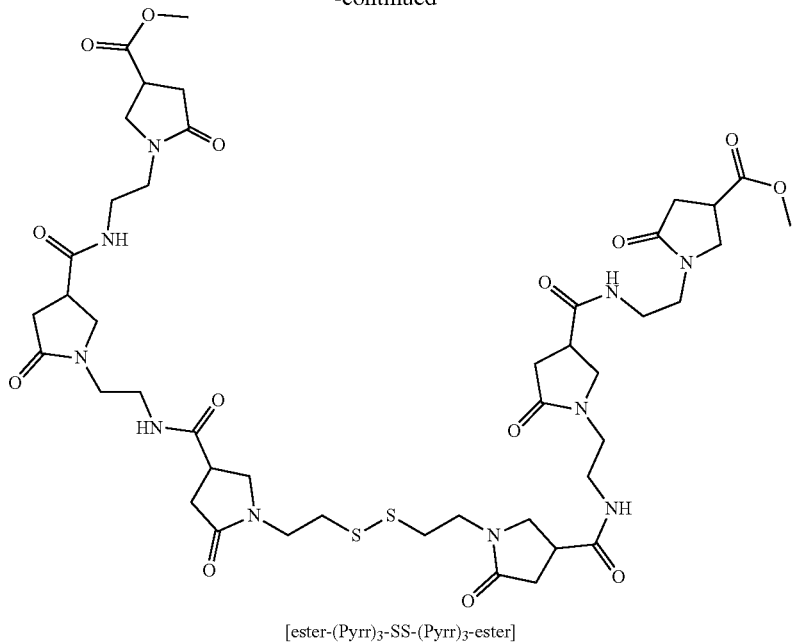

[ester-(Pyrr)₃-SS-(Pyrr)₃-ester]

Example 36: Third Amidation Extension: [NH₂-(Pyrr)₃-SS-(Pyrr)₃-NH₂]

EDA (2.53 mL, 0.03783 mol) in 5 mL of MeOH was charged into a 100 mLRBFequipped with a magnetic stirrer and cooled with ice. While stirring, lester-(Pyrr)₃-SS-(Pyrr)₃-ester; made by Example 351 (1.93 g, 0.001891 mol, 1020.70 g/mol) dissolved in 10 mL of MeOH was added over a period of 15 min. The reaction mixture was stirred in the cold for 15 min and then allowed to stir at RT for 4 days. Minimal methanol was added to make the crude product less viscous, followed by toluene (10 mL) to azeotrope off excess EDA and monitored by silica TLC (10% NH₄OH in methanol). This was azeotropic distillation was repeated 12 times. Yield 2.20 g (108% yield) of a white solid that may contain some solvent. The addition of minimal methanol to decrease viscosity, as well as MeOH use during each round of rotary evaporation to reduce crude product viscosity was determined to be the preferred purification method for the removal of excess EDA. The process provides a compound of the following structure.

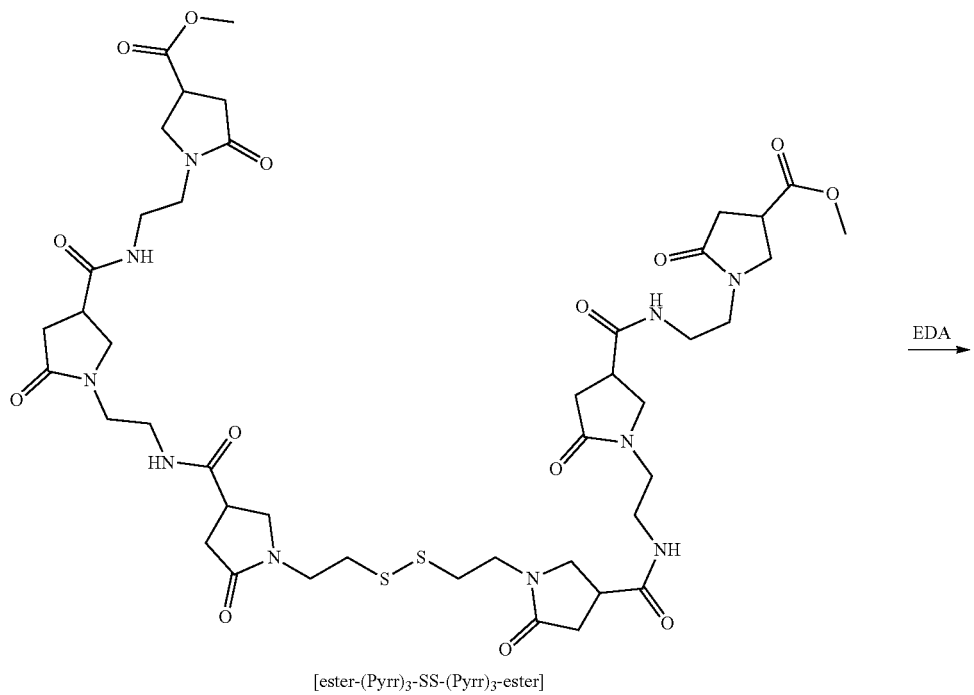

[ester-(Pyrr)₃-SS-(Pyrr)₃-ester]

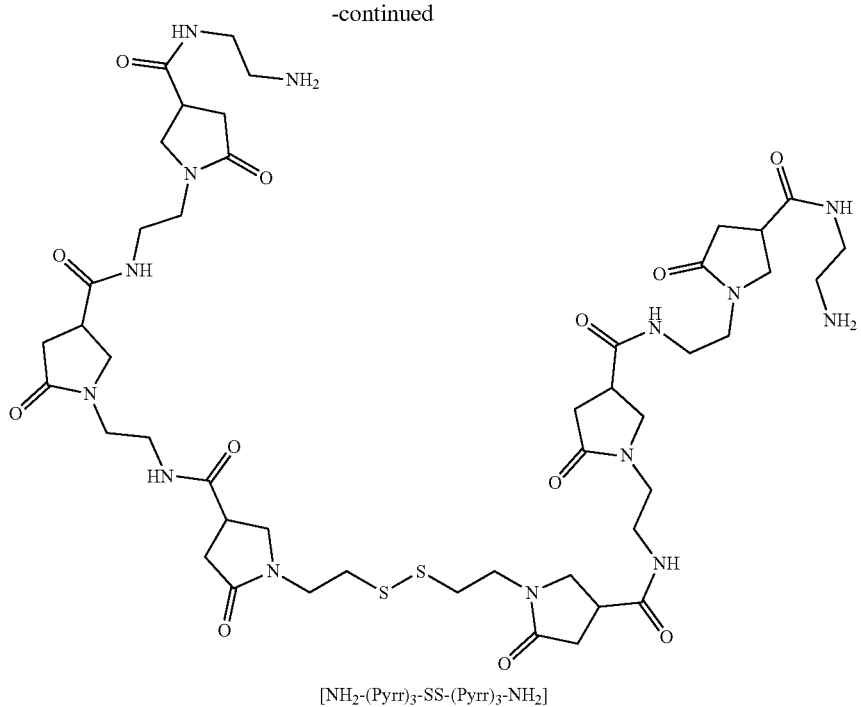

[NH₂-(Pyrr)₃-SS-(Pyrr)₃-NH₂]

Example 37: Fourth Pyrrolidonylation Addition: [Ester-(Pyrr)₄-SS-(Pyrr)₄-Ester]

To a stirred, ice cooled solution of [NH₂-(Pyrr)₃-SS-(Pyrr)₃-NH₂; made by Example 361 (2.29 g, 0.002126 mol. 1077.28 g/mol.) (i.e., 10 mL of MeOH) contained in a 100 mLRBFwas added DMI (0.78 g, 0.004889 mol) (i.e., 10 mL of MeOH) in a dropwise manner over 15 min. After stirring on ice for 15 min, the reaction was allowed to stir at RT for 3 days. $^{13}$C-NMR revealed the absence of DMI and formation of desired product. Methanol was removed by rotary evaporator followed by addition of toluene (10 mL) and decantation. This operation was repeated three times. A plug flow chromatographic separation using (1.5 g silica, 50 mL denatured alcohol) was performed to yield 0.17 g of crude product. Both layers (plug and non-plug) were combined and stored. Both silica TLC (i.e., MeOH) and $^{13}$C-NMR confirmed the presence of desired product [ester-(Pyrr)₄-SS-(Pyrr)₄-ester]. The process provides a compound of the following structure.

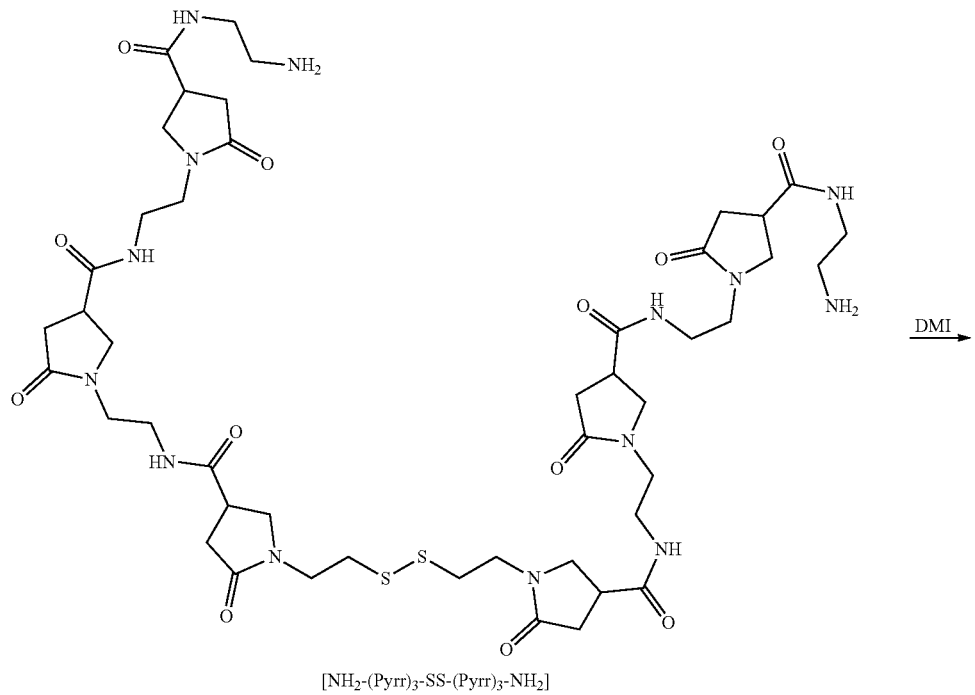

[NH₂-(Pyrr)₃-SS-(Pyrr)₃-NH₂]

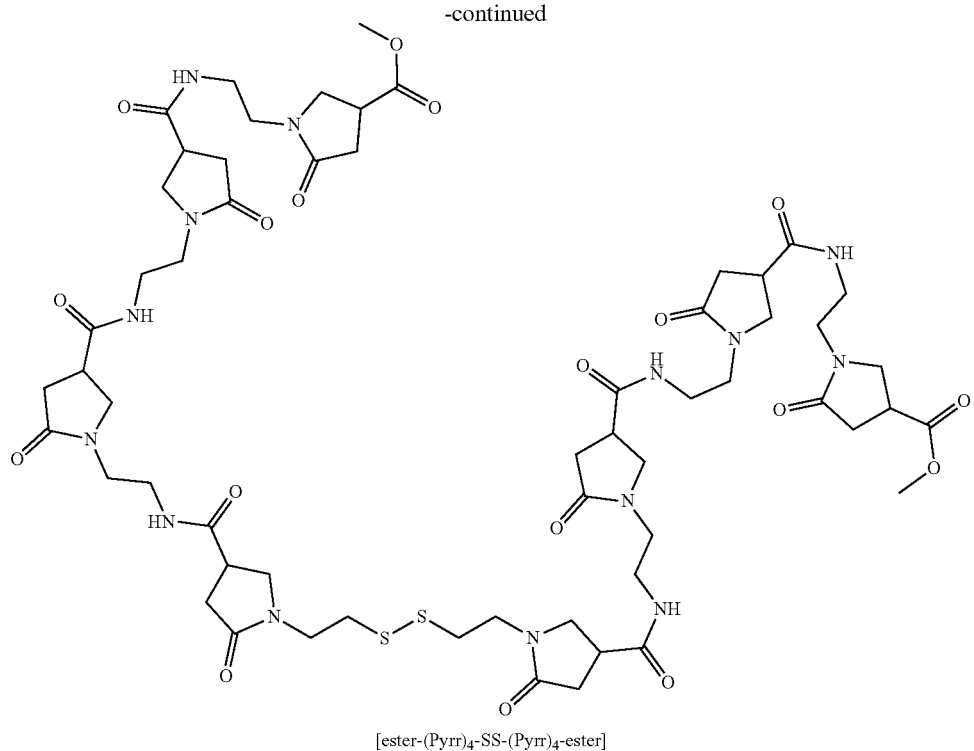

[ester-(Pyrr)₄-SS-(Pyrr)₄-ester]

Example 38: Pyrrolidonylation Using an EDA Core

First Pyrrolidonylation Addition: [Ester-(Pyrr)₂-Ester]

DMI (36.33 g, 0.2297 mol) in 25 mL of methanol (25 mL) was added dropwise while stirring into an ice cooled solution of EDA (6.90 g, 0.1148 mol, 60.10 g/mol) (i.e., in 25 mL of MeOH) contained in a 250 mL round bottomed flask. Drop-wise addition was performed slowly over ~10-15 min. Reaction was allowed to stir on ice for ~15 min and then for 6 days at RT to yield a clear dark yellow solution. Periodic TLC and $^{13}$C-NMR analyses were performed to confirm progression of the reaction. The methanolic solvent was removed on a rotary evaporator, followed by re-suspending the crude product in minimal methanol (i.e., 60° C.). This caused the product to crystallize out of solution as a white solid in the refrigerator overnight. Repeating this crystallization process yielded 32.96 g (92% yield) of white solid product designated as [Ester-(Pyrr)₂-Ester]. The process provides a compound of the following structure.

Example 39: First Amidation Extension: [NH₂-(Pyrr)₂-NH₂]

Excess EDA (6.75 g, 0.1126 mol) was charged into a 50 mL RBF and stirred at RT while [ester-(Pyrr)₂-ester; made by Example 38] (1.76 g, 0.005628 mol, 312.32 g/mol) dissolved in methanol (5 mL) was added drop-wise over a period of 20 min. A slight exotherm was detected. The reaction mixture was stirred in the cold for 30 min, followed by stirring at RT for 3 days. Progress of the amidation reaction was monitored by silica TLC (i.e., 18% NH₄OH in MeOH) and FTIR (i.e., loss of ester peak). The methanol solvent was removed by rotary evaporator, followed by azetropic distillation of excess EDA using repetitive azeotropic distillations with toluene (15 mL). Monitoring with silica TLC (18% NH₄OH in MeOH) showed it required nine azeotropic distillations to remove all EDA. This produced a cloudy viscous orange oil, weighing 2.23 g (108% yield) was confirmed by TLC and $^{13}$C-NMR analyses to contain the desired product with some residual toluene. The process provides a compound of the following structure.

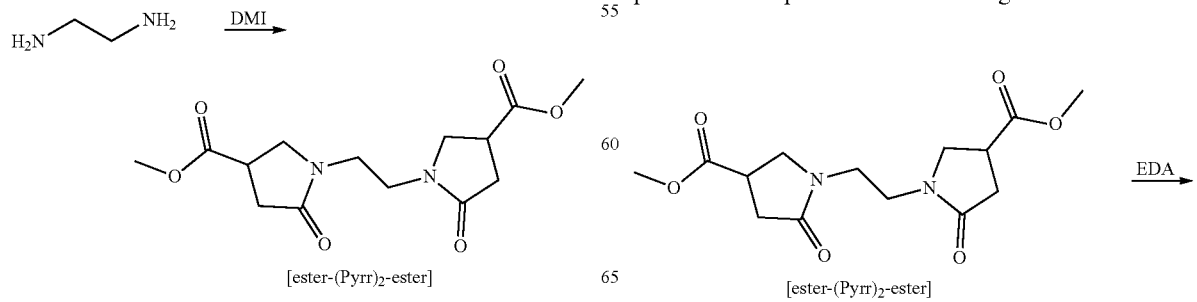

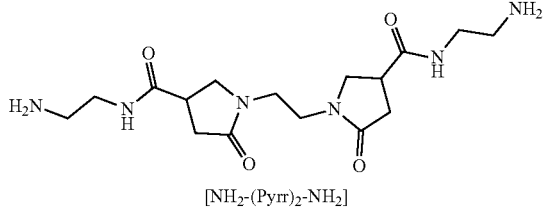

[NH₂-(Pyrr)₂-NH₂]

Example 40: Second Pyrrolidonylation Addition: [Ester-(Pyrr)₄-Ester]

DMI (2.13 g, 0.013507 mol) (i.e., in 10 mL MeOH) was added dropwise over a period of 15 min to [NH₂-(Pyrr)₂-NH₂; made by Example 39] (2.23 g, 0.005628 mol, 368.43 g/mol) (i.e., 10 mL MeOH) in a 50 mL RBF while stirring with ice cooling. After stirring on ice for 15 min, the reaction was then allowed to stir at RT for 18 h. Progress of the pyrrolidonylation reaction was followed by silica TLC (i.e., MeOH) and ¹³C-NMR and FTIR. This analysis demonstrated formation of more mobile pyrrolidone terminated product and new ester functionality for the crude product. Methanol was removed by rotary evaporator and the crude product was further purified by performing a plug flow chromatographic separation using (i.e., 20 g silica, 50 mL denatured alcohol, then 50 mL denatured alcohol, then 100 mL of denatured alcohol). Examination by silica TLC (i.e., MeOH) indicated only minor impurities. All three fractions were combined to yield 2.39 g (68.5% yield) of a slightly viscous pale yellow oil designated: [ester-(Pyrr)₄-ester]. The process provides a compound of the following structure.

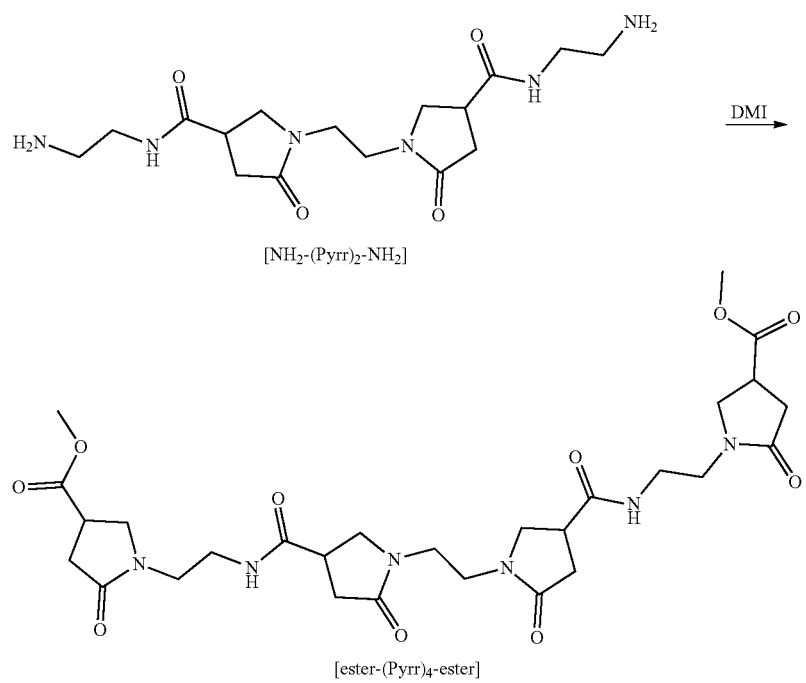

Example 41: Second Amidation Extension: [NH₂-(Pyrr)₄-NH₂]

To a stirred excess of ice cooled EDA (3.24 g, 0.05385 mol) (i.e., 10 mL of MeOH) contained in a 50 mL round bottomed flask, [ester-(Pyrr)₄-ester; made by Example 40] (1.67 g, 0.002692 mol) (i.e., in 10 mL MeOH) was added drop-wise over a period of 15 min, allowed to stir on ice for 5 min and then stirred at RT for 3 days. Methanol solvent was removed by rotary evaporator, followed by azeotropic distillation with toluene (10 mL) to remove excess EDA. This operation was repeated up to 10 times to assure complete removal of EDA and monitored by silica TLC (i.e., 15% NH₄OH in MeOH). After dropping the product on the floor, a "paper towel extraction" was conducted to yield 1.25 g (69% yield) of a viscous pale yellow oil which was consistent with the desired amidation product by FTIR, ¹³C-NMR and TLC. This product was designated as: [NH₂-(Pyrr)₄-NH₂]. The process provides a compound of the following structure.

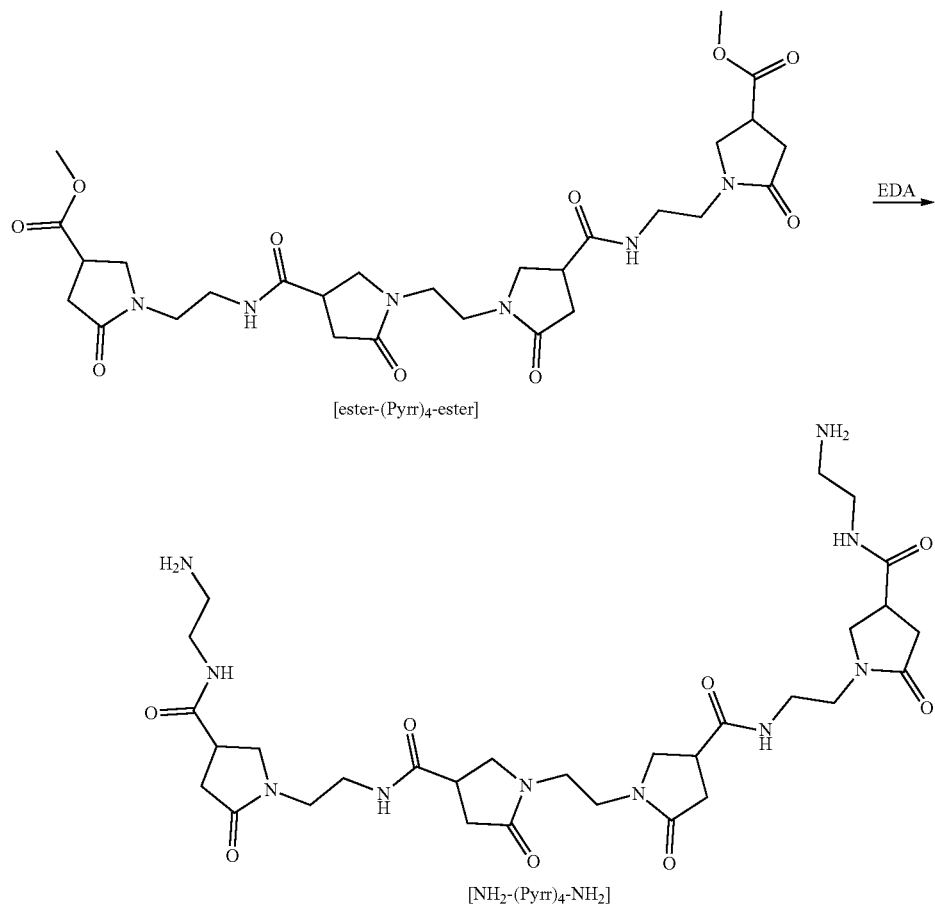

[ester-(Pyrr)₄-ester]

[NH₂-(Pyrr)₄-NH₂]

Example 42: Third Pyrrolidonylation Addition:[Ester-(Pyrr)₆-Ester]

While stirring [NH₂-(Pyrr)₄-NH₂; made by Example 41] (1.25 g, 0.001848 g, 676.37 g/mol) (i.e., 10 mL of MeOH) on ice, a solution of DMI (0.67 g, 0.004251 mol) (i.e., in 10 mL of MeOH) was added drop-wise over a period of 15 min. The reaction mixture was allowed to stir on ice for 15 min, then at RT for 2 days. TLC analysis revealed complete reaction after 4 days. Methanol was removed by rotary evaporator and the crude product was further purified by plug flow silica chromatographic separation using 10 g of silica, 25 mL of denatured alcohol, then 50 mL of denatured alcohol and then analyzed by silica TLC and NMR to give 0.68 g (39.53% yield) of a slightly viscous brown oil designated as:[ester-(Pyrr)₆-ester]. The process provides a compound of the following structure.

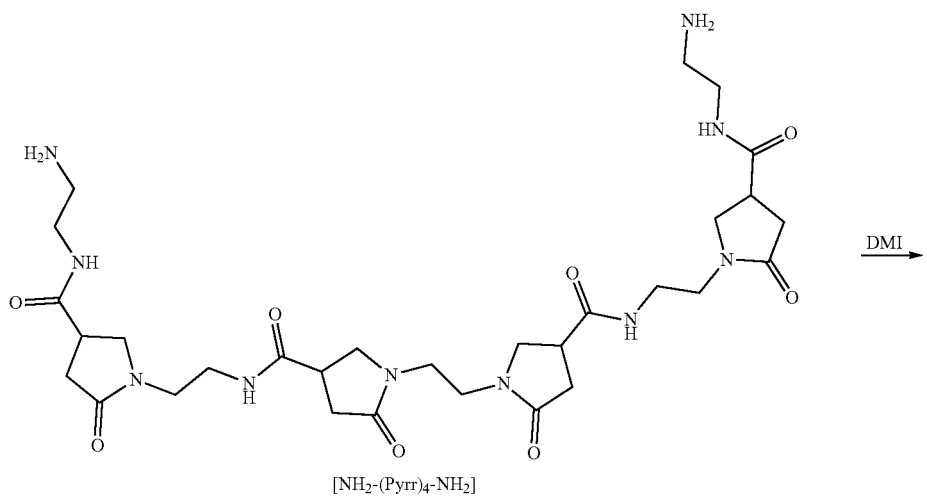

[NH₂-(Pyrr)₄-NH₂]

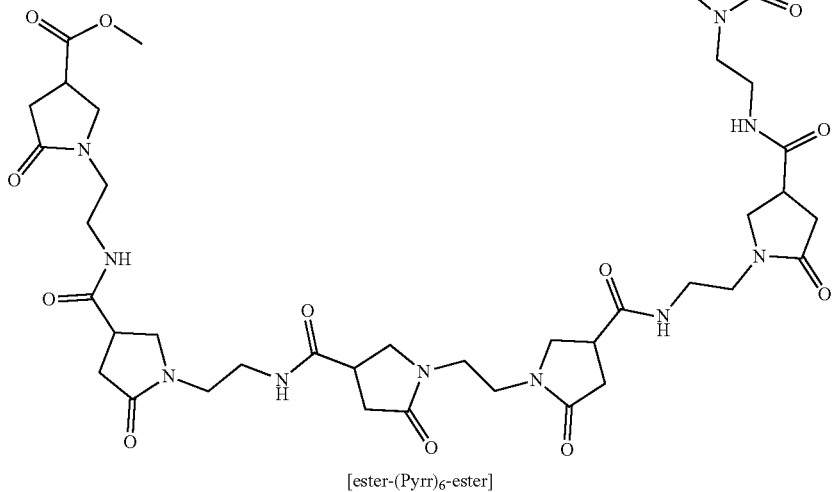

[ester-(Pyrr)₆-ester]

Example 43: Third Amidation Extension: [NH₂-(Pyrr)₆-NH₂]

A solution of [ester-(Pyrr)₆-ester; made by Example 42] (0.48 g, 0.0005167 mol, 928.98 g/mol (i.e., in 10 mL of MeOH) is added drop-wise to a stirred, ice cooled of EDA (0.62 g, 0.01033 mol) (i.e., in 10 mL MeOH) contained in a 50 mL RBF. After stirring for 15 min on ice, the reaction mixture was allowed to stir at RT for 4 days. Residual methanol was removed on a rotary evaporator, followed by azetropic distillation of excess EDA using toluene (10 mL) up to 9 times. Complete removal of EDA was determined by checking with silica TLC (15% NH₄OH in MeOH) to yield 0.68 g (134% yield) which appears to contain some residual solvent. This crude product was designated as: [NH₂-(Pyrr)₆-NH₂]. The process provides a compound of the following structure.

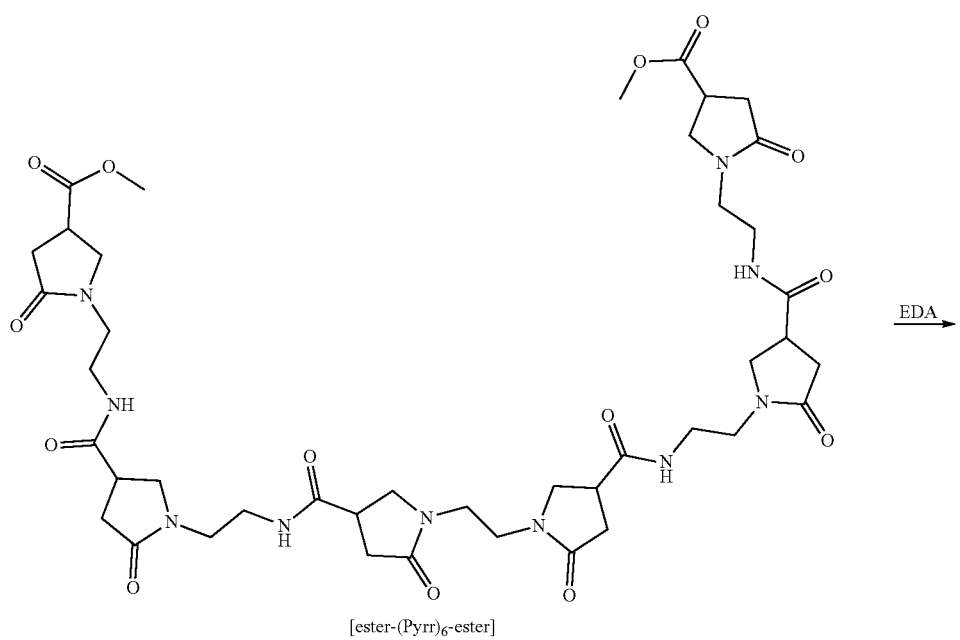

[ester-(Pyrr)₆-ester] →EDA

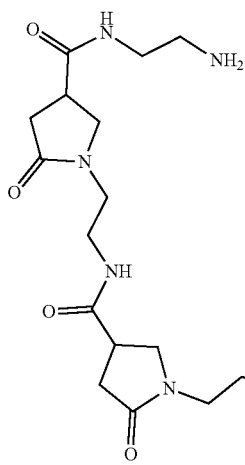
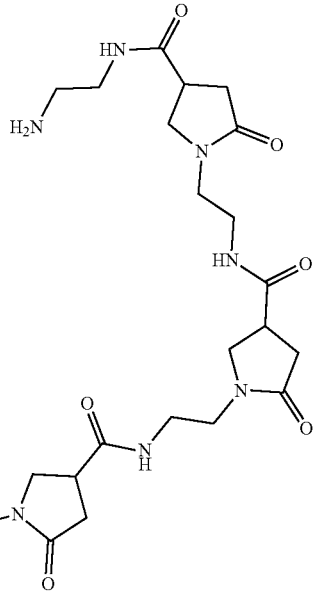

[NH$_2$-(Pyrr)$_6$-NH$_2$]

Example 44: Fourth Pyrrolidonylation Addition: [Ester-(Pyrr)$_8$-Ester]

DMI (0.26 g, 0.001589 mol) (i.e., in 10 mL MeOH) is added dropwise while stirring, to an ice cooled solution of [NH$_2$-(Pyrr)$_6$-NH$_2$; made by Example 43] (0.68 g, 0.0006907 mol, 984.51 g/mol) (i.e., in 10 mL MeOH) contained in a 50 mL round bottomed flask. The DMI addition is performed over a period of 15 min. The reaction was allowed to stir for 15 min while cooled, followed by stirring at RT for 3 days. Progress of the reaction was followed by TLC and $^{13}$C-NMR. The methanol solvent was removed by rotary evaporator, followed by the addition of toluene (i.e., 10 mL) and decanting. This operation was repeated three times to yield 0.65 g (76% yield) of a slightly viscous orange oil. TLC and $^{13}$C-NMR confirmed the expected product. This product was designated as: [ester-(Pyrr)$_8$-ester]. The process provides a compound of the following structure.

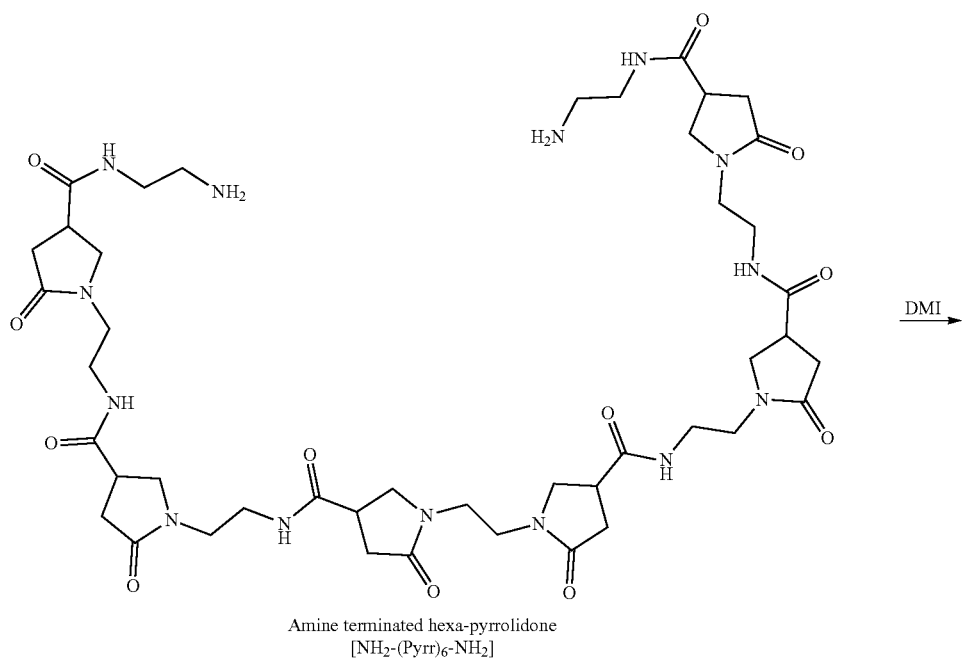

Amine terminated hexa-pyrrolidone
[NH$_2$-(Pyrr)$_6$-NH$_2$]

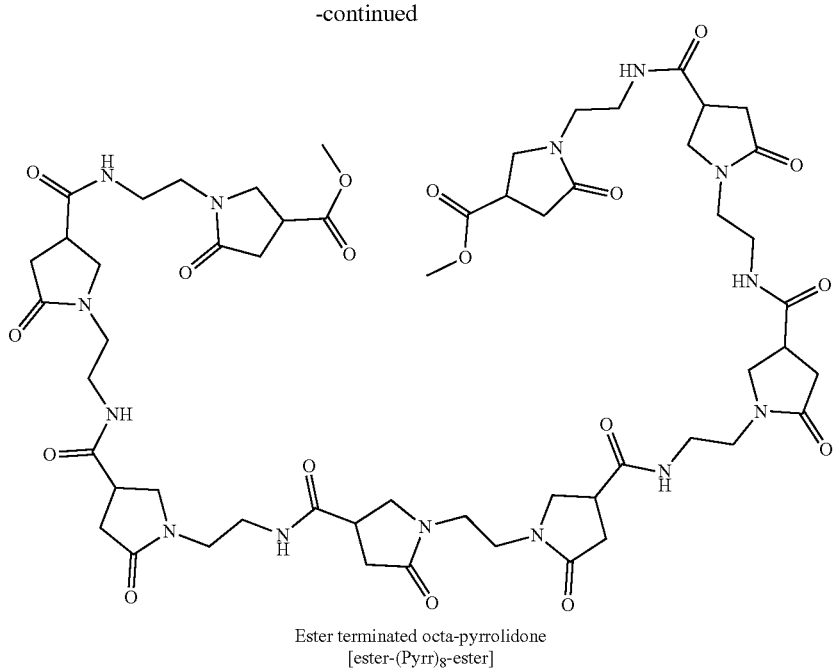

Ester terminated octa-pyrrolidone
[ester-(Pyrr)$_8$-ester]

Example 45: Preparation of 2-(1-Allyl-2-Pyrrolidon-4-yl-)-2-Oxazoline Monomer (a) Synthesis of 1-Allyl-4-Carboxylic Acid Pyrrolidone $$CH_2\!=\!CH\!-\!CH_2\!-\!NH_2 \;+\; \text{Itaconic Acid} \xrightarrow{-H_2O}$$

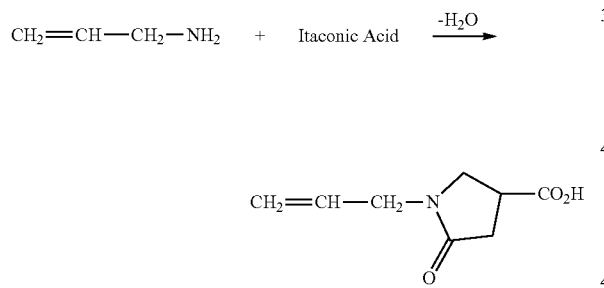

Itaconic acid (13.01 g, 0.1 mol) suspended in 15 mL of dry methanol was charged into a 100 mL RBF equipped with a magnetic stirrer. While stirring, a solution of allyl amine (5.7 g, 0.1 mol.) dissolved in 15 mL of dry MeOH was added dropwise over a period of 20 min. A mild exotherm (i.e., 39° C.) was observed. The reaction mixture was heated under reflux for 1 h, followed by the addition of 20 mL of toluene. The reaction was then equipped with a Dean-Stark apparatus and heated at reflux (i.e., ~130° C.) in an oil bath to until the theoretical amount of water had been removed (i.e., 1.8-2.0 g). The light yellow colored crude reaction mixture gave a strong blue NTIF emission upon exposure to a 395 nm LED. Analysis by FTIR at this stage showed strong bands at 1725 cm-1 (carboxylic acid) and 1636 cm-1 (pyrrolidonyl amide). This crude reaction mixture was devolatilized on a Buchi rotary evaporator (i.e., 150-160/3.5 mm) to give 18.94 g of crude product as a peach colored syrup. Upon standing/cooling, this syrup crystallized into a light yellow solid, mp 65-75° C. (Wt. 16.5 g; 97% yield). Recrystallization gave a product with mp 82° C.

(b) Synthesis of 1-Allyl-4-(2-Hydroxylethyl) Pyrrolidone

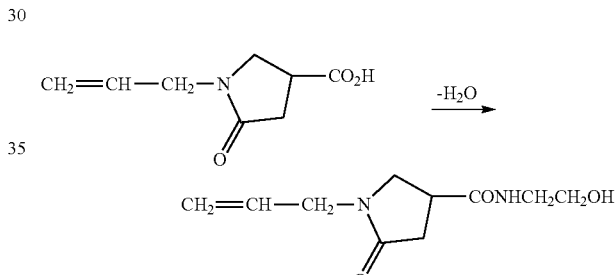

Into a 100 mL RBF equipped with a Dean-Stark apparatus was charged 1-allyl-4-carboxylic pyrrolidone, made by Part (a), (16.9 g, 0.1 mol.) suspended in 50 mL of xylene. While heating at 115° C., 2-aminoethanol (6.5 g, ~0.1+mol.) was added over a period of 2 h. This reaction mixture was heated at reflux over a period of ~12 h until 1.8 g of water had been azeotropically removed (i.e., theoretical required for complete amide formation=1.8 g). Progress of the amidation was monitored by TLC and FTIR.

(c) Cyclo-Dehydration of 1-Allyl-4-(2-Hydroxylethyl) Pyrrolidone to 1-Allyl-4-(2-Oxazoline)

After completing the amidation above, zinc acetate (1.0 g) was added as a cyclodehydration catalyst and the reaction mixture was heated under reflux with the Dean-Stark apparatus until a total of ~2.0 g of water was azeotropically removed (i.e., theoretical required=1.8 g). Completion of this cyclodehydration reaction required ~10-12 h. The xylene was distilled off at atmospheric pressure as the reaction pot reached a temperature of 155° C. Formation of the desired 2-pyrrolidonyl-2-oxazoline in this crude product was confirmed by TLC, $^{13}$C-NMR and FTIR. A portion of this crude product was vacuum distilled (i.e., 230-265/0.1 mm) to give a light yellow liquid which was used for subsequent cationic polymerization described below.

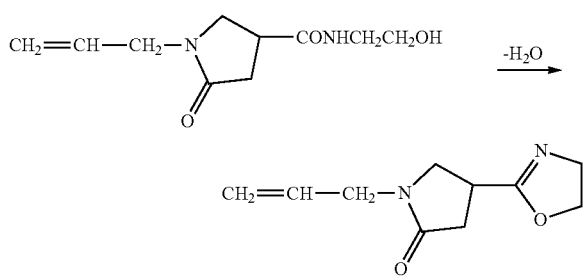

Example 46: Cationic Polymerization of 2-(1-Allyl-4-(2-Oxazolinyl) Pyrridone with Various Functionalized Cationic Initiators and Terminal Group Quenchers In addition to standard cationic initator catalysts (i.e., methyl tosylate, etc.) (Luef et al., *Adv. Polym. Sci.*, 2015, 28, (274), 183-208), a variety of functionalized cationic catalysts, (-X) (i.e., propargyl, allyl, ester, etc.) and terminal quenching reagents (Y) (i.e., thiols, piperazines, azido, hydroxyl, amines, esters, etc.) as shown below, have been described in WO 2008/013618 A1, published 31 Jan. 2008. These functionalized agents may be used to produce monofunctional poly(pyrrolidonyl-2-oxazolines) possessing either initiator or terminal groups for conjugations involving facile and selective "click chemistry". These mono-functionalized poly(pyrrolidonyl oxazolines) may be used for selectively conjugating to functionalized pyrrolidonylation structures, proteins, drugs/pharma or clinically relevant substrates for use as replacements/alternatives for PEGylation-type conjugation products.

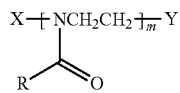

A typical reaction with experimental conditions using 2-ethyl-2-oxazoline are as shown below:

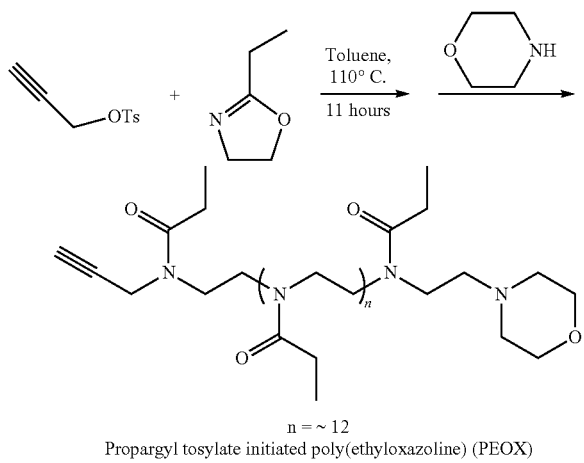

Propargyl tosylate initiated poly(ethyloxazoline) (PEOX)

Example 47: Preparation of Poly(ethyloxazoline) Initiated with Propargyl Tosylate and Terminated with Morpholine To a 250-mL RBF containing a larger stir bar was added propargyl tosylate (2.0 g, 9.52 mmol) and 100 mL of toluene. This flask was fitted with a Dean-Stark apparatus with condenser attached to a $N_2$ line and bubbler. This mixture was heated to reflux for about 30 min distilling 25 mL of toluene into the trap. The system was cooled ~90° C. and the condenser and apparatus were replaced with a septum fitted with a needle connected to a $N_2$ line. To this stirred mixture was cannula transferred over ~5 min ethyl oxazoline (12 g, 121 mmol) freshly distilled under vacuum from $CaH_2$. The septum was replaced with a condenser fitted to a $N_2$ line. This resulting mixture was heated for 11 h at 110° C. with stirring. To this mixture cooled to ~90° C. was added morpholine (2.0 g, 22 mmol, 2.3 equiv.). This mixture was heated for 12 h 110° C. under $N_2$. The resulting mixture was cooled to RT, stripped of volatiles on a rotary evaporator and evacuated with high vacuum at 40° C. to 15 g of crude material. A 800 mg portion of this material was purified using Sephadex LH-20 in MeOH taking 40 fractions of 4 mL each. Fraction 1-10 contained product as determined by TLC (MeOH) and were collected and stripped of volatiles to give 400 mg. Its spectra are as follows:

$^1$H NMR (500 MHz, CDCl3) δ 1.1-1.2 (bm, 3H), 2.2-2.6 (bm, 2H), 3.3-3.6 (bm, 4H).

$^{13}$C NMR (125 MHz, CDCl3) δ 9.38, 9.44, 25.97, 38.93, 43.56, 45.54, 54.08, 66.87, 73.46, 173.91, 174.38, 174.50.

MALDI-TOF MS: distribution from 918 to 2009 with peak at 1315 amu, DP ~12.

Utility Discussion

These new compounds are MW controlled heterocyclic/macrocyclic (i.e. pyrrolidone) type polymer compositions that exhibit IF, low toxicity and low complement activation properties that are suitable for in vivo biological injection and imaging applications. These polymeric compositions can be prepared in four different architectural forms, namely: (a) linear polymers; (b) cross-linked polymers; (c) branched polymers; and (d) dendritic polymers. This general overview can be seen in FIG. 10.

Figure 4:
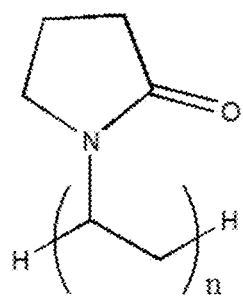
FIG. 4 shows the chemical structures of the Comparative Examples lettered in Table 2.
Figure 4:
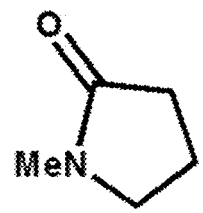
Figure 4:
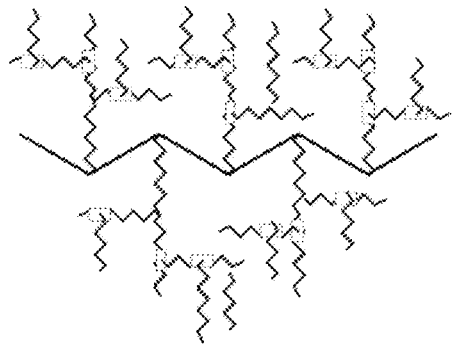
Figure 4:
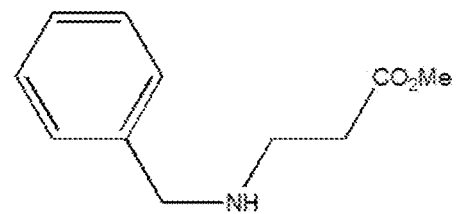

Table 2 below provides the data on the compounds of Formula (I) made by these general procedures. The chemical structures of these compounds are shown in FIG. 3A-D; Comparative example structures are shown in FIG. 4. Additionally, the fluorescence obtained for these compounds is provided.

TABLE 2

| Compound/Example | Excitation Max (nm) | Emission Max (nm) | Relative Response/g |
|---|---|---|---|
| Fluorescein-Na | 470 | 510 | 1,000,000.0 |
| 32 | 280 | 340 | 99,855.2 |
| 33 | 320 | 380 | 391.7 |
| 40 | 305 | 390 | 66.4 |
| 41 peak 1 | 340 | 390 | 62.7 |
| 2-Phenyl-2-imidazoline | 340 | 400 | 50.1 |
| 26 | 325 | 390 | 49.8 |
| 27 | 340 | 400 | 46.8 |
| 39 peak 1 | 355 | 415 | 37.8 |
| 3 | 280 | 305 | 36.1 |
| 28 peak 1 | 280 | 310 | 33.5 |
| 28 peak 2 | 270 | 560 | 31.7 |
| 42 | 335 | 405 | 30.7 |
| 62 | 325 | 410 | 26.8 |
| 43 | 355 | 440 | 22.8 |
| 7 | 340 | 390 | 22.4 |

TABLE 2-continued

| Compound/Example | Excitation Max (nm) | Emission Max (nm) | Relative Response/g |
|---|---|---|---|
| 24 | 330 | 410 | 22.1 |
| 30 | 275 | 315 | 18.9 |
| 41 peak 2 | 285 | 455 | 18.7 |
| 31 | 300 | 350 | 18.7 |
| 29 | 335 | 400 | 16.3 |
| G3 DAB Pyrrolidone carboxamidoethylamine | 245 | 410 | 16.1 |
| 11 peak 1 | 380 | 480 | 15.7 |
| G3 DAB Pyrrolidone carboxamidoethylamine pH 2 | 245 | 375 | 15.1 |
| 36 peak2 | 255 | 305 | 14.6 |
| 44 | 350 | 450 | 14.5 |
| 2 peak 1 | 330 | 410 | 14.4 |
| 11 peak 2 | 370 | 445 | 14.2 |
| 45peak 1 | 262 | 285 | 14.1 |
| 46 peak 1 | 345 | 405 | 12.5 |
| G3 DAB Pyrrolidone carboxamidoethylamine | 330 | 410 | 12.4 |
| 2-Pyrrolidone-5-carboxylic acid | 245 | 385 | 11.8 |
| 48 | 365 | 435 | 11.7 |
| 47 | 300 | 410 | 11.4 |
| 45 peak 2 | 250 or 270 | 575 | 11.2 |
| 39 peak 2 | 245 | 420 | 11.1 |
| D | 315 | 380 | 10.6 |
| G3 DAB Pyrrolidone carboxamidoethylamine pH 2 | 340 | 410 | 10.0 |
| G3 DAB Pyrrolidone carboxamidoethylamine pH 2 | 200 | 360 | 9.3 |
| 49 peak 1 | 260 | 302 | 9.0 |
| 10 | 325 | 410 | 8.6 |
| 9 | 340 | 410 | 8.4 |
| G3 DAB Pyrrolidone carboxamidoethylamine pH 10 | 200 | 380 | 8.3 |
| 14 | 345 | 430 | 7.7 |
| 37 peak 1 | 268 | 302 | 7.0 |
| Core shell tecto(dendrimer) 1 | 360 | 430 | 6.8 |
| Core shell tecto(dendrimer) 2 | 360 | 430 | 6.6 |
| 37 peak 2 | 260 | 565 | 6.5 |
| 36 peak 1 | 340 | 410 | 6.4 |
| G3 DAB Pyrrolidone carboxamidoethylamine | 245 | 380 | 6.3 |
| 50 peak 1 | 365 | 440 | 6.3 |
| 51peak 1 | 305 | 370 | 6.3 |
| 46 peak 2 | 260 | 280 | 6.2 |
| 35 | 277 | 301 | 5.8 |
| 2 peak 3 | 250 | 415 | 5.8 |
| 51 peak 2 | 300 | 350 | 5.8 |
| G3 DAB Pyrrolidone carboxamidoethylamine pH 10 | 340 | 420 | 5.7 |
| 6 | 260 | 460 | 5.4 |
| 13 peak 1 | 335 | 400 | 5.0 |
| 13 peak 2 | 295 | 310 | 4.7 |
| 11 peak 3 | 265 | 450 | 4.4 |
| 52 | 340 | 410 | 4.0 |
| (A) PVP MW 40,000 | 240 | 385 | 4.0 |
| 20 peak 2 | 270 | 440 | 3.7 |
| 18 | 340 | 425 | 3.6 |
| 53 | 340 | 430 | 3.4 |
| 54 | 365 | 440 | 3.4 |
| 55 peak 1 | 340 | 410 | 2.9 |
| 2 peak 1 | 380 | 460 | 2.8 |
| 38 | 335 | 410 | 2.7 |
| 36 peak 2 | 355 | 410 | 2.5 |
| 56 | 335 | 455 | 2.5 |
| 61 | 340 | 420 | 2.4 |
| 36 peak 1 | 365 | 445 | 2.3 |
| 16 | 365 | 440 | 2.2 |
| 34 | 360 | 440 | 2.1 |
| 57 peak 1 | 340 | 420 | 2.1 |
| 57 peak 2 | 285 | 315 | 1.9 |
| 49 Peak 2 | 365 | 450 | 1.7 |
| 56 | 315 | 380 | 1.7 |
| 25 | 350 | 440 | 1.6 |
| 54 weaker peak | 270 | 435 | 1.2 |
| 5 | 320 | 450 | 1.1 |
| 58 | 365 | 455 | 1.0 |
| 22 | 380 | 450 | 0.8 |
| 59 | 280 | 332 | 0.7 |
| 60 | 340 | 440 | 0.7 |
| 55 peak 2 | 305 | 330 | 0.7 |
| 23 | 385 | 460 | 0.3 |

When one of these compounds—is bound to a dendrimers and tested for biological purposes in various cell lines, the results are provided in Example I below.

Example I: Synthesis of PAMAM Pyrrolidone Terminated Dendrimer

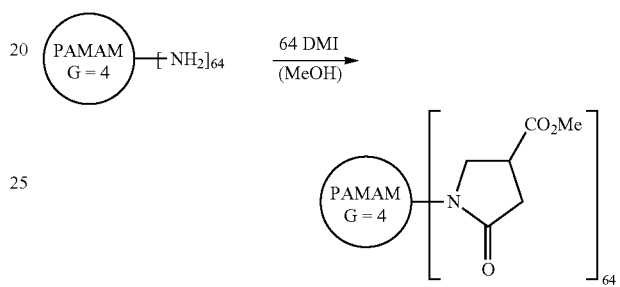

This dendrimer was tested in the following methods to show utility.
Utility in vivo
Cell Culture Chinese hamster fibroblasts (B14) and embryonic mouse hippocampal cells (mHippoE-18) were grown in DMEM medium supplemented with 2 mM glutamine and 10% (v/v) of FBS. Rat liver-derived cells (BRL-3A) were grown in HAM's F12 modified medium, supplemented with 2 mM glutamine and 10% (v/v) FBS. Cells were cultured in T-25 culture flasks in a humidified atmosphere containing 5.0% $CO_2$ at 37° C. and subcultured every 2 or 3 days. Cells were harvested and used in experiments after obtaining 80-90% confluence. The number of viable cells was determined by the trypan blue exclusion assay with the use of Countess Automated Cell Counter (Invitrogen). Cells were seeded either in flat bottom 96-well plates at a density of $1.0 \times 10^4$ cells/well in 100 μL of an appropriate medium or in flat bottom 12-well plates at a density of $2.5 \times 10^5$ cells/well in 1.0 mL of an appropriate medium. After seeding, plates were incubated for 24 h in a humidified atmosphere containing 5.0% $CO_2$ at 37° C. in order to allow cells attaching to the plates.

Uptake and Efflux Detection

In vitro uptake studies were carried out using autofluorescent G4 PAMAM-pyrrolidone dendrimers (prepared in Example I). Briefly, the dendrimer was added at a concentration of 100 μM to the 24-well plates containing cells at the density of $1.0 \times 10^5$ cells/well. In the uptake study, cells were incubated with the dendrimer for a specific time in a range from 5 min to 48 h in humidified atmosphere containing 5.0% $CO_2$ at 37° C. In the efflux study, cells were incubated with the dendrimer for 24 h. Then the dendrimer was removed, cells were washed with PBS and incubated further in medium for a defined time in a range from 5 min to 48 h in humidified atmosphere containing 5.0% $CO_2$ at 37° C. After the appropriate incubation period, cells were washed with PBS, suspended in 500 μL of medium and immediately analyzed with a Becton Dickinson LSR II flow cytometer (BD Biosciences, USA) using a violet laser—405 nm and Pacific Blue bandpass filter—450/50 nm.

Confocal Microscopy

Confocal microscopy images were obtained under 6300× magnification with Zeiss LSM 780 microscope equipped with 405 nm laser diode and InTune excitation laser system (Carl Zeiss Micro Imaging, USA). Cells were grown on 96-well glass-bottom plates and incubated with 100 μM G4-PAMAM-pyrrolidone dendrimers (prepared in Example I) for 24 h in 37° C. humidified atmosphere containing 5.0% $CO_2$. After the incubation, cells were imaged directly (unwashed dendrimer fluorescence) or after subsequent plasma membrane/nuclear staining. For the latter, cells were cooled on ice and washed once with cold PBS to inhibit endocytosis. Cell membranes were than stained by 2-min incubation with NeuroDiO carbocyanine dye diluted 200 times in PBS. Due to high lipophilicity of the dye, staining in these conditions may not be uniform. After membrane staining, cell nuclei were stained with RedDotl nuclear dye diluted 200 times in PBS for 10 min and fixed with 3.6% formaldehyde solution for 15 min in RT. Eventually, fixed and triple stained cells were imaged to visualize intrinsic fluorescence of PAMAM-pyrrolidone dendrimer in blue channel (excitation 405 nm, emission 410-470 nm), plasma membranes in green channel (excitation 490 nm, emission 510-575 nm) and nuclei in far-red channel (excitation 595 nm, emission 600-740 nm).

Results

Figure 5:
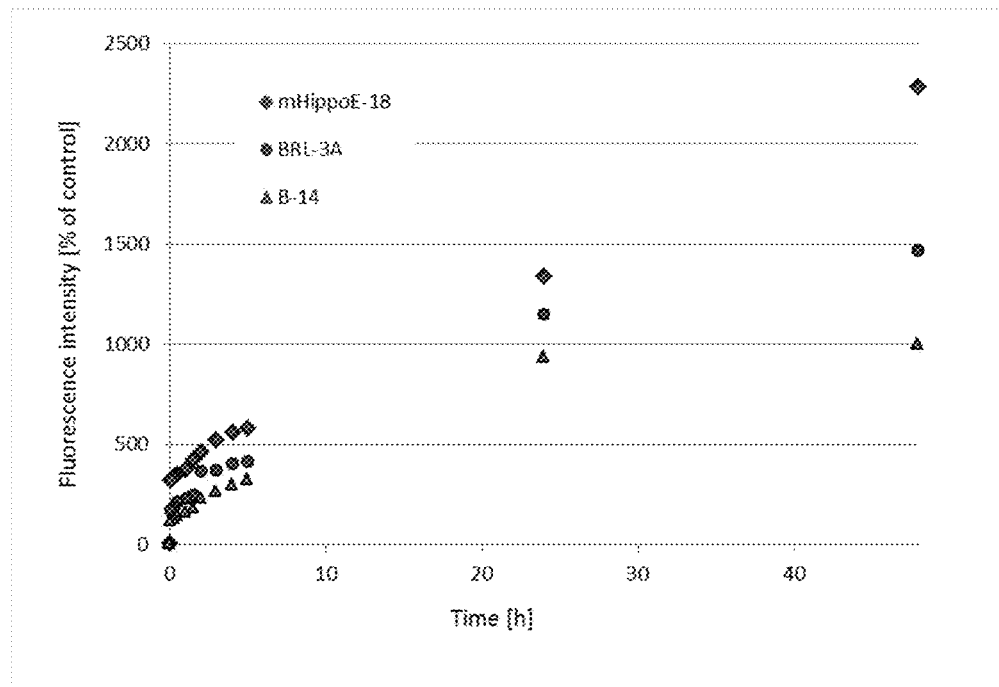
FIG. 5 graphically shows the data of cellular uptake of G4-PAMAM-pyrrolidone dendrimer at a concentration of 100 μM by mHippoE-18 (blue rhombus), BRL-3A (red circles) and B-14 (green triangles) cells after incubation for 5, 15, 30 minutes, 1, 1.5, 2, 3, 4, 5, 6, 24, and 48 hours.

To analyze cellular uptake of the dendrimer by flow cytometry, cells (B14, BRL-3A, and mHippoE-18) were incubated with the dendrimer at a concentration of 100 μM. It has been previously shown that the dendrimer at this concentration is not toxic to any tested cell lines (Janaszewska et al., Nanomedicine NBM, 2013, 9, 461-464). Incubation times varied from 5 min to 48 h. All tested cell lines accumulated PAMAM-pyrrolidone dendrimer rapidly, although its largest amount was observed in mHippoE-18 cells (FIG. 5). After 48 h the intrinsic fluorescence intensity, which is directly proportional to the dendrimer concentration, was almost two times higher for these cells than for B14 cells.

The fluorescence intensity increase that was observed upon incubation of cells with the dendrimer may occur due to two processes: an uptake of the dendrimer within the cells or binding of the dendrimer to the outer layer of cell membranes. To make sure that the dendrimer actually enters the cells and exclude the second possibility, confocal microscopy was used as a visualization technique. Again, this method was based on the intrinsic fluorescence of the dendrimer. The concentration of the dendrimer remained the same and equaled to 100 μM. Confocal images are presented in FIG. 6.

Images showing intrinsic fluorescence of accumulated PAMAM-pyrrolidone dendrimer in three tested cell lines performed after 24 h of treatment without following washout confirm internal localization of the compound (FIG. 6A). Interestingly, some differences in dendrimer localization can be observed between tested cell lines. Although all cells seem to cumulate the dendrimer in cytoplasm, in B-14 and BRL-3A cells nuclear localization can also be observed, whereas in mHippoE-18 cells the fluorescence can be detected in lysosome-like structures, as well as at the cell boundaries (plasma membrane).

In order to further confirm internalization of the dendrimer, all cells were washed once with PBS and stained to visualize plasma membrane and cell nuclei (FIG. 6B). To detect the blue fluorescence of PAMAM-pyrrolidone dendrimer, before formaldehyde fixation, plasma membranes were stained using NeuroDiO carbocyanine dye and nuclei were stained with RedDotl nuclear dye. As expected, dendrimer fluorescence was localized internally in all tested cell lines. Surprisingly, only BRL-3A cells retained staining pattern observed before dendrimer washout and cell fixation, confirming cytoplasmic and nuclear localization. In B14 cells fluorescence could only be detected in endosome-like structures, lacking nuclear accumulation, similarly to mHippoE-18 cells, where the part of dendrimer fluorescence at the plasma membrane could no longer be observed. It can also be noted that the RedDotl staining partially colocalizes with the blue fluorescence signal, probably due to non-intended binding of the dye to PAMAM-pyrrolidone dendrimer.

Figure 7:
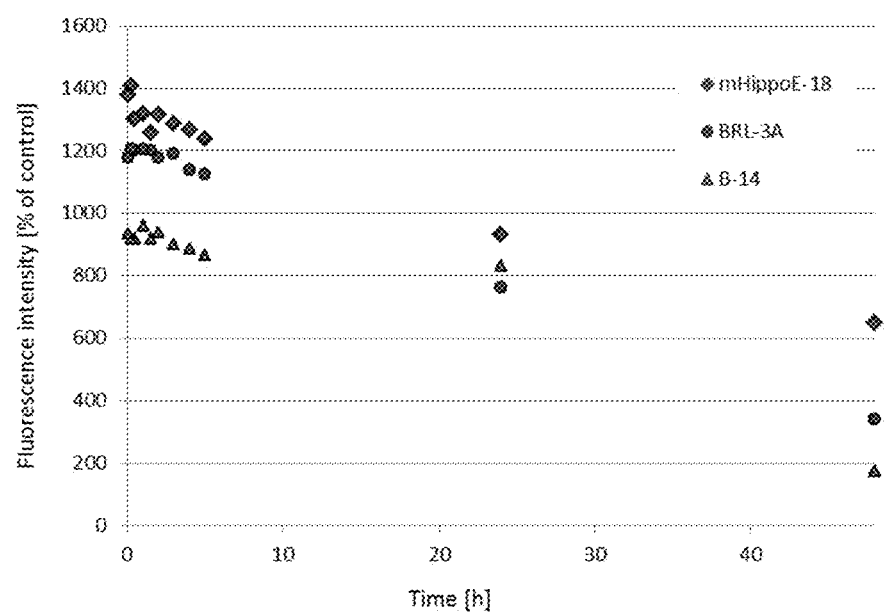
FIG. 7 graphically shows the data for cellular efflux of G4-PAMAM-pyrrolidone dendrimer in a concentration of 100 μM by mHippoE-18 (blue rhombus), BRL-3A (red circles) and B-14 (green triangles) cells after 5, 15, 30 minutes, 1, 1.5, 2, 3, 4, 5, 24, 48 hours.

Another important aspect related to dendrimer internalization in cells is knowing the opposite process—their efflux from the cells. Cellular efflux of the studied dendrimer from B14, BRL-3A and mHippoE-18 cells was analyzed analogously as the uptake by flow cytometry based on the dendrimer intrinsic fluorescence. After 24-hour incubation time the dendrimer was removed from the medium, cells were washed and further incubated in a dendrimer-free medium. As it is shown in FIG. 7, during the first 24 h the dendrimer was being released from all cells but most slowly from B-14 cells. After 24 h only approx. 15% of dendrimers escaped from the B-14 cells. The fastest leakage was observed for mHippoE-18 cells. In the case of B14 and BRL-3A cells, the amount of uptaken dendrimer was not changing during the first 3 h of the experiment. Nevertheless, after 48 h only a half of initial amount of dendrimer in mHippoE-18 cells, one third in BRL-3A cells and one fifth in B-14 cell was observed.

A modified G4 PAMAM dendrimer with 4-carbomethoxypyrrolidone surface groups referred to as a PAMAM-pyrrolidone dendrimer is characterized by a unique property. It is intrinsically fluorescent in neutral pH without any need of an initial procedure such as oxidation. Moreover, this dendrimer has been found to be very biocompatible and non-toxic, contrary to amino-terminated PAMAM dendrimers (Ciolkowski et al., Nanomedicine NBM, 2012, 8, 815-817; Janaszewska et al., Nanomedicine NBM, 2013, 9, 461-464). It even raised a question whether PAMAM-pyrrolidone dendrimer is internalized into cells. Uptake studies combined with confocal microscopy techniques gave a positive answer to this question. Intrinsically fluorescent PAMAM-pyrrolidone dendrimer has been shown to internalize and stain three different cell lines. In the case of BRL-3A cells the dendrimer not only crossed the cell membrane but it also reached the nucleus. To summarize, the PAMAM-pyrrolidone dendrimer possess three distinguishing properties: (1) strong intrinsic fluorescence, (2) low toxicity, (3) cell internalization. Their autofluorescence is strong enough to be visible when dendrimers are in cells.

Due to strong intrinsic blue fluorescence, cellular uptake behavior of PAMAM-pyrrolidone dendrimers could be directly analyzed by confocal microscopy and flow cytometry without additional fluorescence labeling, treatment of dendrimers with chemicals or adjusting pH. This first successful biological experiment opens a broad spectrum of possible PAMAM-pyrrolidone dendrimer applications as gene vectors, and drug delivery platforms that combine two functions: transporting and bioimaging at the same time.

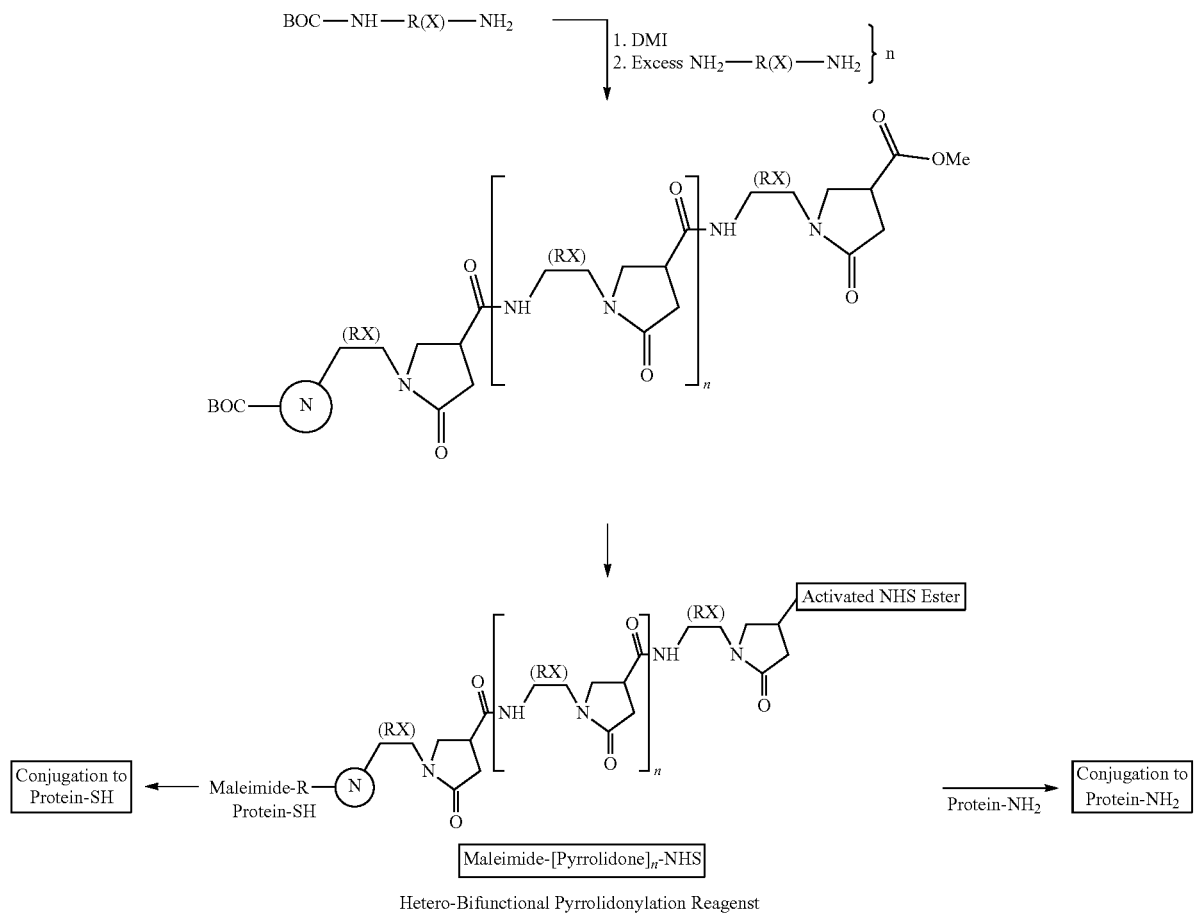

Hetero-Bifunctional Pyrrolidonylation Reagenst
Deprotection and introductions of NHS and maleimide moieties according to
G. Hermanson, *Bioconjugate Techniques* (2008).

Using routine protocols familiar to those skilled in the art as taught by G. T. Hermanson, *Bioconjugation Techniques*, Second Ed., (2008), these discrete, well defined homo- or hetero-functionalized (see Chapters 4, 5, pp 233-334) PYRROLIDONylation reagents were created to mimic traditional PEGylation reagents. They were prepared from the various new small molecule pyrrolidone derivatives, pyrrolidone containing oligomers, dendrons, dendrimers and polymers described earlier, These PYRROLIDONylation reagents may be conjugated to various proteins, polypeptides, enzymes, antibodies, drugs, polynucleotides, biological substrates, and nanoparticles, etc. as taught by G. T. Hermanson, Chapter 18, 25; in *Bioconjugation Techniques*, Second Ed., (2008), References to these protocols for several specific substrates of interest are as follows: (a) dendrons/dendrimers; Chapter 7, pp 346-394; imaging/chelating agents, Chapter 9,pp 400-496; biotin/avidin, Chapter 11, pp 507-543, Chapter 233, pp 900-921; microparticles/nanoparticles, Chapter 14,15, pp 582-645; hapten-carrier immunogens, Chapter 19, pp 745-781; antibodies, Chapter 20, pp 787-821; immunotoxins, Chapter 21, pp 827-857; liposomes, Chapter 22, pp 858-897; enzymes, Chapter 26. pp 961-968; nucleic acids/oligonucleotides,Chapter 26, pp 970-1002, to mention a few.

This invention now provides a solution to this scientific dilemma by demonstrating that certain interative processes and principles used in the divergent synthesis of dendrimers [DENDRIMERS, DENDRONS, AND DENDRITIC POLYMERS, Tomalia, D. A., Christensen, J. B. and Boas, U. (2012) Cambridge University Press, New York, N.Y.] may be applied to the synthesis of discrete, well defined poly (pyrrolidone) oligomers and polymers. FIG. 10 illustrates the three major architectural components of a dendrimer, namely (a) core, (b) interior and (c) the surface. As such, the divergent construction of a dendrimer begins with an initiator core around which concentric dendritic layers of branched monomers (i.e., branch cell monomers) are covalently attached in well-defined iterative reaction sequences to produce a sequence of dendritically branched shells referred to as generations (G). This dendritic growth of the interior and the number of surface groups presented as a function of generation is recognized to be mathematically controlled as a function of the core multiplicity ($N_c$), the branch cell multiplicity, ($N_b$) and the generation level, (G). As such, the number of surface groups presented at each generation (Z) may be predicted according to the following mathematical expression; $Z=N_c N_b^G$. For example, traditional divergent synthesis of poly(amidoamine) (PAMAM) dendrimers begins with an intiator core of know multiplicity (Nc) that may be either an amine or ester. Generally starting with an amine core (i.e., diaminobutane; (DAB); Nc=4) one adds a stoichiometric amount (i.e., 4×) of methyl acrylate (MA) by Michael addition to produce a PAMAM ester terminated intermediate (FIG. 10). This is followed by addition of an excess of ethylene diamine (EDA) which produces a mild, facile amidation of the terminal ester groups to produce the PAMAM amine terminated intermediate (FIG. 10). This reaction sequence of (a) Michaels addition followed by (b) amidation constitutes an "iterative reaction sequence" for producing discrete, well-defined dendritic macromolecules referred to as dendrons (Nc=1) or dendrimers (Nc>2).

Earlier we reported the facile reaction of PAMAM dendrimer terminal primary amine moieties to yield N-substituted-4-carbomethoxy pyrrolidones (i.e., (I). FIG. 10) [WO2004/069878, Aug. 19, 2004], wherein, a precise number of pyrrolidone rings were formed according to the number of primary amines (Z) present as a function of generation. The reaction of primary/secondary amines with the secondary 4-carbomethoxy ester moieties on the pyrrolidone ring were not expected to be and indeed were not as reactive as with the primary ester groups derived from methyl acrylates. That withstanding, we have now found appropriate conditions to perform those reactions in high yield under facile conditions.

As such, in an effort to control the molecular weights of certain poly(pyrrolidone) oligomers/polymers below certain threshold limits to assure renal kidney excretion (i.e., <20 KDa) for injectable in vivo applications or other medical uses, we have invoked the use of certain dendrimer/dendron based "iterative reaction processes/principles". These efforts have now led to the discovery of at least three novel, well-defined poly(pyrrolidone) oligomer/polymer and dendron/dendrimer compositions (see poly(pyrrolidone) composition categories; II, III and IV (FIG. 10). These compositions exhibit extraordinarily low toxicity, non-complementary activity/non-interactive, stealthy properties with proteins that are very reminiscent of poly(ethyleneglycols) (PEGs). As such, these compositions are referred to as PYRROLIDONylation reagents and are expected to provide excellent, cost effective alternatives to PEGylation reagents. Furthermore, it was discovered unexpectedly that a non-traditional, "intrinsic fluorescence" property is associated with these pyrrolidone oligomers/polymers as well as many related small molecule pyrrolidone intermediates that have served as monomeric intermediates to these polymeric pyrrolidones.

Although the invention has been described with reference to its preferred embodiments, those of ordinary skill in the art may, upon reading and understanding this disclosure, appreciate changes and modifications which may be made which do not depart from the scope and spirit of the invention as described above or claimed hereafter. Accordingly, this description is to be construed as illustrative only and is for the purpose of teaching those skilled in the art the general manner of carrying out the invention.

What is claimed is:

1. Fluorescent cyclic amide, cyclic urea, cyclic urethane and cyclic amino amide or amino urea compounds of the formula

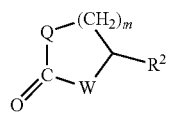

Formula (I)

wherein:

Q is the residue of a compound having at least one primary amine that provides the nitrogen atom in the ring as shown;

W is N, O, S or $(CH_2)_n$ where n is 0 or 1;

$R^2$ is —C(O)OH; —C(O)O($C_1$-$C_4$ alkyl); 2-oxazoline; —C(O)—$NHR^5$ wherein $R^5$ is H; —$C_1$-$C_4$ alkyl or an amido group that can be a moiety on a polymer; including pharmaceutically acceptable salts and esters of —$CO_2$H;

m is 1-4; and with the proviso that the compound of Formula (I) fluoresces after excitation at least 10×the value of its base compound which is $QH_2$ not having such cyclic amides, cyclic urea, cyclic urethanes or cyclic amino amide entities present.

2. The compound of claim 1 wherein $R^2$ is —C(O)OH; —C(O)O($C_1$-$C_4$ alkyl); —C(O)—$NHR^5$ wherein $R^5$ is —$C_1$-$C_4$ alkyl or an amido group that can be a moiety on a polymer.

3. The compound of claim 1 wherein its emissions are in the visible-near infrared region of 400-850 nm.

4. The compound of claim 1 wherein its excitations are in the UV visible region of 200-385 nm.

5. The compound of claim 1 wherein Q is a primary amine of a core shell tecto(dendrimer).

6. The compound of claim 1 wherein Q is a primary amine from (1) small organic molecules, (2) oligomers and polymers which are derived from any of the four major, polymer architecture types including linear, cross-linked, branched and dendritic polymer types, including both organic and inorganic compositions of silicas, inorganic oxides, metal chalcogenides, fullerenes, or (3) any of the Soft or Hard nano-elements that are nanoparticles.

7. The compound of claim 1 wherein Q is ($C_1$-$C_{20}$ alkyl) amine, ($C_1$-$C_{20}$ hydroxylalkyl) amine, ($C_1$-$C_{20}$ alkyl ether) amines, $C_6$-$C_{14}$ aryl or ($C_6$-$C_{14}$ aryl $C_1$-$C_4$ alkyl) amines; 2-oxazoline; or X—Z—N— where X is H, —OH, —$NH_2$, —SH, —$CO_2$H and Z is ($C_1$-$C_{18}$ alkyl), ($C_6$-$C_{12}$)aryl, ($C_6$-$C_{12}$)arylene, ($C_6$-$C_{12}$)alkylarylene, ($C_1$-$C_{20}$ alkyl)amine; ($C_1$-$C_{20}$ hydroxylalkyl) amine; ($C_1$-$C_{20}$ alkyl) etheramines; benzylamine; or

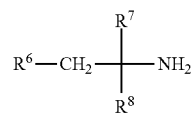

Formula (A)

where $R^6$ is —$NH_2$, or —C(O)OH, and $R^7$ and $R^8$ are independently —H or $C_1$-$C_4$ alkyl or —$CH_2$OH; a dendrimer, dendron or dendritic polymer, each having primary amines on its surface; a fatty/lipophilic entity with a primary amine, which when cyclized can form an amphiphilic surfactant that will lead to fluorescent micelles, a protein having a primary amine, or any of the amino acids.

8. The compound of claim 1 wherein W is $(CH_2)_n$ where n is 1; and m is 1.

9. The compound of claim 1 wherein Q is an amine terminated dendritic polymer or an amine terminated dendron.

10. A fluorescent compound of the formula

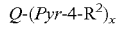

Formula (IV)

wherein:
Q is the residue of a compound having at least one primary amine that provides the nitrogen atom that becomes a part of a pyrrolidone moiety;
x is from 1 to the total number of primary nitrogens present in Q;
$R^2$ is —C(O)OH; —C(O)O($C_1$-$C_4$ alkyl); 2-oxazoline; —C(O)—$NHR^5$ wherein $R^5$ is H; $C_1$-$C_4$ alkyl or an amido group that can be a moiety on a polymer; including pharmaceutically acceptable salts and esters of —$CO_2$H; and
with the proviso that the total pyrrolidone moieties have a molecular weight of not greater than 100 KDa and the size of the compound of Formula (IV) is not greater than 15 nm.

11. The compound of claim 10 wherein $R^2$ is —C(O)OH; —C(O)O($C_1$-$C_4$ alkyl); —C(O)—$NHR^5$ wherein $R^5$ is —$C_1$-$C_4$ alkyl or an amido group that can be a moiety on a polymer.

12. The compound of claim 10 where Q is ($C_1$-$C_2$ alkyl) amine, ($C_1$-$C_{20}$ hydroxylalkyl) amine, ($C_1$-$C_{20}$ alkyl ether) amines, $C_6$-$C_{14}$ aryl or ($C_6$-$C_{14}$ aryl $C_1$-$C_4$ alkyl) amines.

13. The compound of claim 10 that is a MW controlled pyrrolidone moiety containing polymer composition of Formula (IV) that exhibits intrinsic fluorescence (IF), low toxicity and low complement activation properties that are suitable for in vivo biological injection and imaging applications.

14. The compound of claim 10 as a substitute for PEG in PEGylation.

15. A compound of Formula (III):

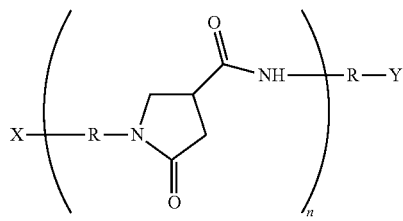

Formula (III)

wherein: R is $C_1$-$C_{18}$ alkyl, $C_6$-$C_{12}$ aryl, $C_6$-$C_{12}$ arylene, ($C_1$-$C_{12}$ alkyl) $C_6$-$C_{12}$ arylene; and X=Y is independently H, —OH, —$NH_2$, —SH, —$CO_2$H, alkyne, azido or any suitable reactive moiety, required for conjugating the pyrrolidonylation reagents to desired/targeted substrates includes peptides, proteins, antibodies, enzymes, polynucleic acids, drugs, nanoparticles, microparticles, liposomes, micelles, dendrimers, dendrons, dendrimersomes, pharmaceutics, or other biological entities or fragments thereof.

16. The compound of claim 15 wherein n is 1-150.

17. The compound of claim 16 wherein: X—R—N—is Q: wherein Q is the residue of a compound having at least one primary amine that provides the nitrogen atom in the ring.

18. The compound of claim 15 which after excitation has fluorescence.

19. The compound of claim 15 as a substitute for PEG in PEGylation.

20. Fluorescent macrocyclic amides having from 4 to 14 components of the formula

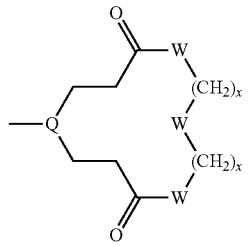

Formula (II)

wherein Q and W are defined as in Formula (I) in claim 1; and x is 2 or 3.

21. A process for preparing the compounds, of Formula (IV) as defined in claim 10 which comprises reacting Q, as defined in claim 10, with a reagent of itaconic acid (ITA), itaconic ester (ITE) or dimethyl itaconate (DMI), optionally in methanol in the desired stoichiometry between the various primary amine moieties and the reagents where the resulting compound of Formula (IV) has the total molecular weight of not greater than 100 KDa and the size of the compound of Formula (IV) is not greater than 15 nm.

* * * * *